US006902896B2

(12) United States Patent
Ranum et al.

(10) Patent No.: US 6,902,896 B2
(45) Date of Patent: Jun. 7, 2005

(54) INTRON ASSOCIATED WITH MYOTONIC DYSTROPHY TYPE 2 AND METHODS OF USE

(75) Inventors: Laura P. W. Ranum, St. Paul, MN (US); John W. Day, Minneapolis, MN (US); Christina Liquori, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 191 days.

(21) Appl. No.: 10/143,266

(22) Filed: May 10, 2002

(65) Prior Publication Data

US 2003/0108887 A1 Jun. 12, 2003

Related U.S. Application Data

(60) Provisional application No. 60/337,831, filed on Nov. 13, 2001, provisional application No. 60/302,022, filed on Jun. 29, 2001, and provisional application No. 60/290,365, filed on May 11, 2001.

(51) Int. Cl.[7] ............................ C12Q 1/68; C07H 21/04
(52) U.S. Cl. ........................ 435/6; 435/91.1; 435/91.2; 536/23.1; 536/24.3; 536/24.31; 536/24.33
(58) Field of Search .......................... 435/6, 91.1, 91.2; 536/23.1, 24.3, 24.31, 24.33, 24.32

(56) References Cited

FOREIGN PATENT DOCUMENTS

WO          01/72799 A1    10/2001

OTHER PUBLICATIONS

Sequence Information Contained in Celera Accession No. 2HTBKUAD8C, "Conting Overlapping ZNF", pp. 1–310.
Harper, "Myotonic Dystrophy," Second Edition, W.B. Sanders, London 1989. Title Page and Table of Contents.

Alwazzan et al., "Myotonic Dystrophy is associated with a reduced level of RNA from the DMWD allele adjacent to the expanded repeat," *Hum. Mol. Genet.*, 1999; 8(8):1491–7.
Aminoff et al., "Autonomic functon in myotonic dystrophy," *Archives of Neurology*, Jan. 1985; 42(1):16.
Andrews et al., "The glycoprotein Ib–IX–V complex in platelet adhesion and signaling," *Thromb Haemost*, 1999; 82(2):357–64.
Armas et al., "Primary structure and developmental expression of Bufoarenarum cellular nucleic acid–binding protein: changes in subcellular localization during early embryogenesis," *Dev. Growth Differ.*, Feb. 2001; 43(1):13–23.
Boucher et al., "A novel homeodomain–encoding gene is associated with a large CpG island interrupted by the myotonic dystrophy unstable (CTG)n repeat," *Hum. Mol. Genet.*, 1995; 4(10):1919–25.
Brook et al., "Molecular basis of myotonic dystrophy: expansion of a trinucleotide (CTG) repeat at the 3' end of a transcript encoding a protein kinase family member," *Cell*, Feb. 21, 1992; 68(4):799–808.
Buxton et al., "Detection of an unstable fragment of DNA specific to individuals with myotonic dystrophy," *Nature*, Feb. 6, 1992; 355(6360):547–8.
Davis et al., "Expansion of a CUG trinucleotide repeat in the 3' untranslated region of myotonic dystrophy protein kinase transcripts results in nuclear retention of transcripts," *Proc. Natl. Acad. Sci. USA*, Jul. 8, 1997; 94(14):7388–93.

(Continued)

*Primary Examiner*—Cynthia Wilder
(74) *Attorney, Agent, or Firm*—Mueting Raasch & Gebhardt, P.A.

(57) ABSTRACT

The present invention provides methods for identifying individuals not at risk for developing myotonic dystrophy type 2 (DM2), and individuals that have or are at risk for developing DM2. The present invention also provides isolated polynucleotides that include a repeat tract within intron 1 of the zinc finger protein 9.

33 Claims, 19 Drawing Sheets

OTHER PUBLICATIONS

Day et al., "Clinical and genetic characteristics of a five-generation family with a novel form of myotonic dystrophy (DM2)," *Neuromuscul. Disord.*, 1999; 9(1):19–27.

Flink et al., "Organization of the gene encoding cellular nucleic acid–binding protein,"*Gene*, 1995; 163(2):279–82.

Fu et al., "An unstable triplet repeat in a gene related to myotonic muscular dystrophy," *Science*, Mar. 6, 1992; 255(5049):1256–58.

Fu et al., "Decreased expression of myotonin–protein kinase messenger RNA and protein in adult form of myotonic dystrophy," *Science*, Apr. 9, 1993; 260(5105):235–8.

Groenen et al., "Expanding complexity in myotonic dystrophy," *Bioessays*, Nov. 1998; 20(11):901–12.

Harley et al., "Expansion of an unstable DNA region and phenotypic variation in myotonic dystrophy," *Nature*, Feb. 6, 1992; 355(6360):545–6.

Helderman–van den Enden, "Monozygotic twin brothers with the fragile X syndrome: different CGG repeats and different mental capacities," *J. Med. Genet.*, 1999; 36(3):253–7.

Kawaguchi et al., "CAG expansions in a novel gene for Machado–Joseph disease at chromosome 14q32.1," *Nat. Genet.*, 1994; 8(3):221–8.

Khajavi et al., "'Mitotic drive' of expanded CTG repeats in myotonic dystropy type 1 (DM1)," *Hum. Mol. Genet.*, 2001; 10(8):855–63.

Klesert et al., "Trinucleotide repeat expansion at the myotonic dystrophy locus reduces expression of DMAHP," *Nat. Genet.*, Aug. 1997; 16(4):402–6.

Klesert et al., "Mice deficient in Six5 develop cataracts: implications for myotonic dystrophy," *Nat. Genet.*, May 2000; 25(1):105–9.

Koob et al., "An untranslated CTG expansion causes a novel form of spinocerebellar ataxia (SCA8)," *Nat. Genet.*, Apr. 1999; 21(4):379–84.

Korade–Mirnics, "Myotonic dystrophy: molecular windows on a complex etiology," *Nucleic Acids Res.*, Jun. 1998; 26(6):1363–8.

Kruglyak et al., "Parametric and nonparametric linkage analysis: a unified multipoint approach," *Am. J. Hum. Genet.*, Jun. 1996; 58(6):1347–63.

Lathrop et al., "Strategies for multilocus linkage analysis in humans," *Proc. Natl. Acad. Sci. USA*, 1984; 81(11):3443–6.

Liquori et al., "Myotonic dystrophy type 2 (DM2) Caused by a CCTG Expansion in Intron 1 ofZNF9," *Science*, 2001; 293(5531):864–7.

Liquori et al., "Science—Liquori et al. 293(5531): 864 Data Supplement—Supplemental Data," [online]. Available online Aug. 3, 2001. [retrieved on Sep. 12, 2002]. Retrieved from the Internet: <http://www.sciencemag.org/cgi/content/full/293/5531/864/DC1>.

López de Munain et al., "CTG trinucleotide repeat variability in identical twins with myotonic dystrophy," *Ann. Neurol.*, Mar. 1994; 35(3):374–5.

Lu et al., "Cardiac elav–type RNA–binding protein (ETR–3) binds to RNA CUG repeats expanded in myotonic dystrophy," *Hum. Mol. Genet.*, 1999; 8(1):53–60.

Mahadevan et al., "Myotonic dystrophy mutation: an unstable CTG repeat in the 3' untranslated region of the gene," *Science*, Mar. 6, 1992; 255(5049):1253–5.

Mankodi et al., "Myotonic dystrophy in transgenic mice expressing an expanded CUG repeat," *Science*, Sep. 8, 2000; 289(5485):1769–73.

Matsuura et al., "Large expansion of the ATTCT pentanucleotide repeat in spinocerebellar ataxia type 10," *Nat. Genet.*, Oct. 2000; 26(2):191–4.

Matsuura et al., "Polymerase chain reaction amplification of expanded ATTCT repeat in spinocerebellar ataxia type 10," *Ann. Neurol.*, Feb. 2002; 51(2):271–2.

McPherson et al., "A physical map of the human genome," *Nature*, Feb. 15, 2001; 409(6822):934–41.

Miller et al., "Recruitment of human muscleblind proteins to (CUG)(n) expansions associated with myotonic dystrophy," *EMBO J.*, 2000; 19(17):4439–48.

Moutou et al., "Transition from premutation to full mutation in fragile X syndrome is likely to be prezygotic," *Hum. Mol. Genet.*, 1997; 6(7):971–9.

National Center for Biotechnology Information, National Library of Medicine, National Institutes of Health, GenBank Locus AC022944, Accession No. AC022944, "*Homo sapiens* chromosome 3 clone RP11–814L21 map 3, Sequencing in Progress, 81 unordered pieces." [online]. Bethesda, MD [retrieved on Jun. 21, 2000]. Retrieved from the Internet: <URL: www.ncbi.nlm.nih.gov/entrez/query.fcgi?cmd=Retrieve&db=nucleotide&list_uid s=7139791&dopt=GenBank>; 75 pgs.

National Center for Biotechnology Information, National Library of Medicine, National Institutes of Health, GenBank LocusAC022993, Accession No. AC022993, "*Homo sapiens* chromosome 3 clone RP11–72304 map 3, Working Draft Sequence, 14 unordered pieces." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uid s=10046450&dopt=GenBank>; 53 pgs.

National Center for Biotechnology Information, National Library of Medicine, National Institutes of Health, GenBank Locus AC023598, Accession No. AC023598, "*Homo sapiens* chromosome 3 clone RP11–221E20, Working Draft Secquence, 3 unordered pieces." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uid s=21700434&dopt=GenBank>; 56 pgs.

National Center for Biotechnology Information, National Library of Medicine, National Institutes of Health, GenBank LocusAF388525, Accession No. AF388525, "*Homo sapiens* ZNF9 gene, intron 1 and CL3N58 repeat region." [online]. Bethesda, MD [retrieved on Aug. 20, 2000]. Retrieved from the Internet: <URL: www.ncbi.nlm.nih.gov/entrez/query.fcgi?cmd=Retrieve&db=nucleotide&list_uid s=15193053&dopt=GenBank=; 2 pgs.

National Center for Biotechnology Information, National Library of Medicine, National Institutes of Health, GenBank LocusAF388526, Accession No. AF388526, "*Homo sapiens* ZNF9 gene, intron 1 and expanded CL3N58 repeat region." [online]. Bethesda, MD [retrieved on Aug. 20, 2002]. Retrieved from the Internet: <URL: www.ndbi.nlm.nih.gov/entrez/query.fcgi?cmd=Retreive&db=nucleotide&list_uid s=15193054&dopt=GenBank>; 2 pgs.

National Center for Biotechnology Information, National Library of Medicine, National Institutes of Health, GenBank LocusAF389886S1, Accession No. AF389886, "*Homo sapiens* zinc finger protein 9 (ZNF9) gene, exon 1." [online]. Bethesda, MD [retrieved on Aug. 20, 2002]. Retrieved from the Internet: <URL: www.ncbi.nlm.nih.gov/entrez/query-.fcgi?cmd=Retrieve&db=nucleotide&list_uids=15193056&dopt=GenBank=; 5 pgs.

National Center for Biotechnology Information, National Library of Medicine, National Institutes of Health, GenBank Locus AF389886S2, Accession No. AF389887, "*Homo sapiens* zinc finer protein 9 (ZNF9) gene, exons 2 through 5, and complete cds." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uid s=15193057&dopt=GenBank>; 4 pgs.

National Center for Biotechnology Information, National Library of Medicine, National Institutes of Health, GenBank Locus HUMZFPSREB, Accession No. M28372, "*Homo sapiens* sterol regulatory element–binding protein (CNBP) mRNA, complete cds." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uid s=643575&dopt=GenBank>; 2 pgs.

National Center for Biotechnology Information, National Library of Medicine, National Institutes of Health, GenBank Locus HSU19765, Accession No. U19765, "Human nucleic acid binding protein gene, complete cds." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uid s=790570&dopt=GenBank>; 4 pgs.

Orr et al., "Expansion of an unstable trinucleotide CAG repeat in spinocerebellar ataxia type 1," *Nat. Genet.*, Jul. 1993; 4(3):221–26.

Otten et al., "Triplet repeat expansion in myotonic dystrophy alters the adjacent chromatin structure," *Proc. Natl. Acad. Sci. USA*; Jun. 6, 1995; 92(12):5465–9.

Pellizzoni et al., "Cellular nucleic acid binding protein binds a conserved region of the 5' UTR or *Xenopus laevis* ribosomal protein mRNSs," *J. Mol. Biol.*, 1997, Mar. 28; 267(2):264–75.

Pellizzoni et al., "Involvement of the *Xenopus laevis* Ro60 autoantigen in the alternative interaction of La and CNBP proteins with the 5'UTR of L4 ribosomal protein mRNA," *J. Mol. Biol.*, Aug. 28, 1998; 281(4):593–608.

Philips et al., "Disruption of splicing regulated by a CUG–binding protein in myotonic dystrophy," *Science*, May 1, 1998; 280(5364):737–41.

Pulst et al., "Moderate expansion of a normally biallelic trinucleotide repeat in spinocerebellar ataxia type 2," *Nat. Genet.*, Nov. 1996; 14(3):269–76.

Rajavashisth et al, "Identification of a zinc finger protein that binds to the sterol regulatory element," *Science*, Jul. 7, 1989; 245(4918):640–43.

Ranum, "Genetic mapping of a second myotonic dystrophy locus," *Nat. Genet.*, 1998; 19(2):196–8.

Reddy et al., "Mice lacking the myotonic dystrophy protein kinase develop a late onset progressive myopathy," *Nat. Genet.*, Jul. 1996; 13(3):325–35.

Ren et al., "Hydrolysis of GTP on rab 11 is required for the direct delivery of transferrin from the pericentriolar recycling compartment to the cell surface but not from sorting endosomes," *Proc. Natl. Acad. Sci. USA*, May 1998; 95(11):6187–92.

Ricker et al., "Proximal myotonic myotonic myopathy: a new dominant disorder with myotonia, muscle weakness, and cataracts," *Neurology*, 1994; 44(8):1448–52.

Ricker et al., "Linkage of proximal myotonic myopathy to chromosome 3q," *Neurology*, Jan. 1, 1999; 52(1):170–1.

Sambrook et al., "Molecular Cloning: A Laboratory Manual," Cold Spring Harbor Laboratory, New York; 1989; title page, publication page, table of contents; 30 pgs.

Sarkar et al., "Heterozygous loss of Six5 in mice in sufficient to cause ocular cataracts," *Nat. Genet.*, May 2000; 25(1):110–4.

Schneider et al., "Proximal myotonic myopathy: evidence for anticipation in families with linkage to chromosome 3q," *Neurology*, 2000; 55(3):383–8.

Spielman et al., "Transmission test for linkage disequilibrium: the insulin gene region and insulin–dependent diabetes mellitus (IDDM)," *Am. J. Hum. Genet.*, Mar. 1993; 52(3):506–16.

Takahashi et al., "The CUG–binding protein binds specifically to UG dinucleotide repeats in a yeast three–hybrid system," *Biochem. Biophys. Res. Commun.*, 2000, Oct. 22; 277(2):518–23.

Taneja et al, "Foci of trinucleotide repeat transcripts in nuclei of myotonic dystrophy cells and tissues," *J. Cell Biol.*, Mar. 1995; 128(6):995–1002.

Tapscott, "Deconstructing myotonic dystrophy," *Science*, Sep. 8, 2000; 289(5485):1701–2.

Tapscott, "Reconstructing Myotonic Dystrophy," *Science*, 2001; 293:816–7.

Thornton et al., "Myotonic dystrophy with no trinucleotide repeat expansion," *Ann. Neurol.*, Mar. 1994; 35(3):269–72.

Thornton et al., "Expansion of the myotonic dystrophy CTG repeat reduces expression of the flanking DMAHP gene," *Nat. Genet.*, Aug. 1997; 16(4):407–9.

Timchenko et al., "Identification of a $(CUG)_{11}$ triplet repeat RNA–binding protein and its expression in myotonic dystrophy," *Nucleic Acids Res.*, Nov. 1, 1996; 24(22):4407–14.

Ullrich et al., "Rab11 regulates recycling through the pericentriolar recycling endosome," *J. Cell Biol.*, Nov. 1996; 135(4):913–24.

Venter et al., "The sequence of the human genome," *Science*, Feb. 16, 2001; 291(5507):1304–51.

Warner et al., "A general method for the detection of large CAG repeat expansions by fluorescent PCR," *J. Med. Genet.*, Dec. 1996; 33(12):1022–6.

Wong et al., "Somatic heterogeneity of the CTG repeat in myotonic dystrophy is age and size dependent," *Am. J. Hum. Genet.*, Jan. 1995; 56(1):114–22.

"Zinc Finger Protein 9; ZNF9," Online Mendelian Inheritance in Man–John Hopkins University. [retreived on Apr. 30, 2002]. Retrieved from Internet: <URL: http://www.ncbi.nlm.nih.gov/entrez/dispomim.cgi?id=116955>.

"ZNF9: zinc finger protein 9 (a cellular retroviral nucleic acid binding protein)" [online]. *Homo sapiens* Office Gene Symbol and Name (HGNC), [retrieved on Apr. 30, 2002]. Retrieved from the Internet: <URL: www.ncbi.nlm.nih.gov/LocusLink/LocRpt.cgi?1=7555>.

Zhuchenko et al., "Autosomal dominant cerebellar ataxia (SCA6) associated with small polyglutamine expansions in the $\alpha_{1A}$–voltage–dependent calcium channel," *Nat. Genet.*, Jan. 1997; 15(1):62–9.

E

```
              Exon 1:  4337-4415
Intron 1 Gap (size unknown):  14469-14473
    CL3N58 repeat region:  17702-17857
              Exon 2:  18662-18799
              Exon 3:  18896-18987
              Exon 4:  19156-19356
              Exon 5:  19865-20845

1  actaatgaaa tgttcattaa atgatttgtc agtgtttcaa agtttcttta
  51  tcatcagtta gcattcccta caccatcact ttagggagtc aatagaattt
 101  tataggagta ggcttcagta agtactggga ggccagtagc actgttcaag
 151  cacatgggct gtctgtgttt gaagcctgac ctgtcatttg ttcactttct
 201  gacttgagca gattacttaa actctctcga cctgtttctt catggggata
 251  atacaagtac ttctaggggg tttgtgaaaa ctcataaaga ggttaaaaac
 301  attgcctggc atacagtaag cacccaataa gaataagaaa taatatttgt
 351  atagtaatta tgccagaaac tgttataaga gctgtatata tattaacaat
 401  tagctattac tagtattact aattcctagt tcaggattta gcttagtaaa
 451  ctttctgctt cagaagcaaa tacgagaggt gaaaacatca atttattctc
 501  ctcagtctta gttacatact ttccaagtca agtcacagag cacaatttcc
 551  ttgctggcag ggacaagaca tgggtttaca tgatatcacc tatcccctca
 601  atttaacagc atgtactatg cagttgggca tttaagcaga aattaagagt
 651  tggcaggtat tgctcaactg gtacccattt taggaataat gctgaatcat
 701  agcattttat ctggtcttct ctcaggatac ttaatgctaa ttttttgtat
 751  ttttagtaga gacgggattt caccttgtta gccaggatgg tctcgatctc
 801  ctgacctcat gacccatctg cctcggcccc caaagtgct gggattatag
 851  gcgtgatcca ccgtgcccgg acttttttt ttttttttt tttgagacag
 901  agtctcctc tgttgtgcag gctggagtgc agtggcccaa tctcttgctc
 951  ccaggtgcaa gcgattctcc tgcctcagct tccaagtag ctgggattac
1001  aggtgcccac caccactc ggctaatttt tgtgttatta gtagagacaa
1051  gttttcacta tgttgcccag gctgtctca aactcctgac ctcaggtgat
1101  ccacctacct cggcctccca agtgctggga agttgttttt ttttctttt
1151  cttttttga gactgagtct tgctccgtca cccaggctgg agtgcagtgg
1201  cgtgatctcg gctcactgca agctctgcct ctcaggttca acgattctc
1251  ctgcctcaac ctctcgagta gcttggacta taggtcccg ccaccacgac
1301  cagctaattt tttgtatttt tagtagacag gatttcaccg tgttagccag
1351  gatggtcttg atcagctgac ctcgtgatcc gcccgcctcg gcctcccaaa
1401  gtgctggatt acaggcgtga gccaccgaac cagccgaca cttaatactt
1451  tcttatggcc cttgttatcc tgcaagttct tcaagggcaa actctgtgtc
1501  ttaagtagtc acctttgtaa cccttgcaat gctgagcatg agactgaaca
1551  ctggaggaga ggaggggaat aaaacatctc cagggaagag gaatgtaatg
1601  ggagcctctt caagtccac tggcagctta tcttttgagt gagcttttc
1651  ctattttcaa acatttctag taaaataggc ataccaaagg gtatatccag
1701  gcaatacaag ccattgtagt taaattccac catacacctt ttctggcgcc
1751  tcacgatcag cctggctcta ttaataatag tcgttacagg aagctgcatg
1801  ccaggtagaa agagccatta gctgttacca ctccactgcc aagaagtaaa
1851  gacattgttt ccatttcttc tacttaagtc ttttaaaacc tatagaacat
```

Fig. 7a

```
1901  tatgtccagt atctctatct cacactcact ttcattttct atagctgttg
1951  aaatttttgt tttaatatta ggaatattcc attcctgggt ctataatgaa
2001  tagcaaacat tttatacagt actatggttg gaatggtaaa caaaaataag
2051  tcagaaaata ttaattttg gccatatggt aatttaact tgtcctcttg
2101  gtgtggtgtg gacgcaccca ggttggactt catacatagc ctcttgcatt
2151  atattgactc attgtcagag ctcacgaagt cactacctaa gtgtctgatt
2201  gctacactat acattacttc aagatactat gaaggttaat cagattacaa
2251  aggggaaatc ataaagctga gtaagcttct tggtaataaa actatataaa
2301  tacaaaatac tgttttttat tggcagataa tatatcgtgt tttagcacaa
2351  cacataagct gctaggcatt tattcaatct gattgggaat gggttaaatt
2401  tggttaaaaa attttacctt aggttgcttt aattaaaaaa atgtttaagg
2451  ctgagtgcag tgctcacac ctgtaatcct agcactttgg gggcactggg
2501  tgcagtggct cacacctgta atcctagcac tttggcctag caccgcttga
2551  ggccaggagt tcaagcccag cctggccaac atgatgaaac cccatctcta
2601  ctaaaaatac aaaaattagc caggcgtggt ggtgggcgcc tgcagtccca
2651  gctactcagg aggctgaggc agaattggtc aaacatggga agcggaggtt
2701  gcagtgagct gagacagcac tccagcttgg gcaacagagg gagaccctgt
2751  ctcaaaaat agtaataaat aaatttaaaa agttcggcca ggcgcggtgg
2801  ctcatgcctg taatcccagt gctttgggag gacgatcacc actttgggtg
2851  ggcggatcac ctgaggtcgg gagtttgaga ccagcctgac caacatggag
2901  aaaccccgcc tatactaaaa atacaaaatt agccgggcgt ggtggcgcat
2951  gcctataatc ccagctactg gggaggctga ggcaggagaa tcacttgaat
3001  ccaggaggcg gaggttgcag tgagctgaga tcgtgccatt gcactccagc
3051  ctgggcaacg gagtgagact ccgttctcaa aaaaaaaaa aagtttaaaa
3101  tatcattggt ctttaaagtt atacattcat tctttgataa ttgctatgtt
3151  gaacgcaacc tcctaactgc tttacaatga ttaagcacta atgatttgaa
3201  cccaggttta aagtctgact ctcaacacat gtgctctgcc ttctcacgaa
3251  catgatttca aaaatcatag ccccgggatt tgggattggt ggcttatgcc
3301  tgtaaaccca gcgacagagc aagaccctac tcttaaaaaa aaaaaaaatt
3351  aaagaaaaaa agaaaaataa atcatagtgt tgaactggca ggtttcactg
3401  agacgaaact tgggactctt ccttttttt tgtttcgaat aaagccattc
3451  tagaatgaga caaaattcta aatatttta tagttaacag tttaaattgg
3501  gtttaatctt gacaagacta tctagggcta tatacacaaa tctcttttgg
3551  agaaaatacc acaactaaac tgaagtctat tcctgaatat gacagaccag
3601  gtcaaatggt tatccttgcc ctcccggggg atgtcactca taaacgtgcc
3651  aaaagtcaca gtctaggccc cattaccta catgctcatg accttcccag
3701  ggaggcccct cgccttacc aggcactttc atcttgggaa gacacatcag
3751  tcctggcgga gaaagcagca aggcctttcc ccggctcaca aaaattaata
3801  caaatctcag aggctgcatc ccacagccgt gaccaccgtg acttggcatc
3851  ccctttctg caaacttaaa tgttatctag aaatcgggcc tggctctgaa
3901  agccaagggc ctggcaggag cccgagaaag gggagaaact ttctgcggcc
3951  ccaagctaat ggcagtcact gcaccgagac ccgtcccctg catccctt
4001  gctccagctg gccaagacag accaccaagg tcagccagat tccacccag
4051  tctggccggg cccggaccca gctggaatg aaccgagaag caccgggacc
4101  cggatcccgg cgtgaaaggc cgcgcgcggg gcacggcggg aaaagacgct
4151  gcgcgcagaa acacccgccc cgcgccgcgc tctagtgggc ggccctgccg
```

Fig. 7b

```
4201   cgggcggctc  tgattggact  gccgaacccc  gcgcgctgat  tggccgcgtg
4251   ggcgaggcgg  aggagagccg  tgcgcagcgg  cgtatgtggg  gccgtgtgca
4301   gacccgcgtg  tggcgcaggc  aaggaccctc  aaaataaaca  gcctctacct
4351   tgcgagccgt  cttccccagg  cctgcgtccg  agtctccgcc  gctgcgggcc
4401   cgctccgacg  cggaaggtga  gggctggggg  aggggcccgg  cgctgacgga
4451   gccgcagtgc  gggtcgggtc  tgtggcggac  agagagggta  gggagcggcg
4501   aggtggcgat  ggcggccgca  ctttggcctg  cgcctctgct  gcgtcaggcg
4551   ggaagctcgg  ctgctgccgc  cgcctcggac  ccgggtttct  ggcgcaccgc
4601   tgtcggacga  cacttctgtc  ctttcttcgt  cctggaaagc  tgggtcgccg
4651   agcatgcggg  tctttcggcg  ccacggccgc  acccaggcc   gcaggcttag
4701   ggcagaggag  gcccgcccgt  gcgccttgg   ggccgaggcc  ctgacgcttc
4751   gagggtcgcg  gaatgaggga  ccgagggtgg  atttggcggg  aactcactgg
4801   aaggagtccg  tgtggtgggg  aaaggctccc  ggctgcggat  gaaggggga
4851   tggggtgggt  atagtcgtgc  aggccatgtg  ctggggtcgt  gcgcctggcg
4901   ggccatgtgc  caagggtttt  ggggcctta   gaaaagggtt  cttaggccgg
4951   gcgcggtggc  tcacgcctgt  aatcccagca  ctttgagagt  cccaggcggg
5001   cggatcacga  ggtcaggagt  tcgagaccag  cctgaccaat  atggtgaaag
5051   ttggtctgta  ctaaaaataa  aaaattagcc  gggcatggtg  gcgggcgcat
5101   gtagtcccag  cagctcggga  ggctggacag  gagaatcgcg  tgaaccccgg
5151   aggccgaggt  tgtggtgagc  cgagatcgcg  ccactacact  ccagcatggg
5201   caacagagag  agactccgtc  ttaaaaaaac  aaacaaacaa  acaaacaaac
5251   aacaacaaag  ggttcctgaa  gaagcctttg  tgtttggagt  ggcgagactg
5301   ctggaagact  tgggagcttt  tagagttat   actccctatc  cttgatagtt
5351   ttccgattct  tgaattttta  tcgtcattta  aatactaagt  tgcttgtgtt
5401   acattaccat  tccaaaaggg  gctgatgggg  ctcacattcc  aagagttaac
5451   actatttaag  ttgctgggat  cctttaaaag  cgccattacc  agaaaaaaca
5501   cgaatttgtc  aaacctccaa  aaccacagca  gcgggcggta  gtctgcatca
5551   tttcttggat  taatgaaaca  gatgtaatta  caaacgagac  acgaaattca
5601   actagctccc  ctccatctag  attttttccat  atcgtgagaa  cctgttttag
5651   aatggcataa  tggtccacat  ttgggtttag  gtgttgattt  tattatgggt
5701   aaggcttgtg  cttgttccca  catgttaacc  atatggcctc  agccacaggg
5751   cacttccaaa  ggaagtgact  gtttctggtc  ttggggtct   tgtaaaaaga
5801   gaacattgct  cagtaatcgt  ctgtgatttt  agctagtgtg  tttcaggcat
5851   tattcagaag  gactcaggtg  agataagcca  aaactgaatt  tgttttttgt
5901   ctttctcaaa  gtgaaggagg  tctaatgaat  atccccatct  tgcttttaaa
5951   ttacattttt  aaaagtagat  ttttcccct   ttcctattgt  ttgacccaat
6001   tttggagtga  aacgtaacca  gttactattt  ccattcgaat  ttaaattagc
6051   aattttatgt  tatttgtttg  ttcaagcagt  ataactggag  tgtagagctt
6101   tgagggtttc  aaaaagataa  gagatatagt  acttatctcc  tgggcttccc
6151   cctccccct   cctaaatagt  tttaaatgct  tctaatgagt  tactctggtt
6201   aaggataatc  aaacacctgt  aaactgccag  gatcctaggt  acatgctgtt
6251   tttagtttgt  tgagcctgat  tcttgtctac  aagagttctt  tgtgtattgg
6301   aatataaaag  gaataattta  ttcattccc   aaggcagaa   ttaaagactt
6351   aagttttcc   gatttcatct  cttgataagt  ttttctttaa  aaaataaca
6401   gtttgtgttt  ttctgaggaa  ccaaaggtcc  tcttttttt   catattggta
6451   acaggagagg  taatgtattt  cagatggtgc  agtctgtaaa  atattttgaa
```

Fig. 7c

| | | | | |
|---|---|---|---|---|
| 6501 | ccaaatcagt | ggaagaccag | gggttttttct | tttttttttt | ctgagacgga |
| 6551 | gtctcactct | gtcgcccaag | ctggagtgca | gtggcgcgat | ctcggctcac |
| 6601 | tgcgacctcc | gcctcccgga | ttaagcgatt | ctcctgcctc | agcctccgaa |
| 6651 | gtagctggga | ttacaggcgc | ccgccgccac | acccagctag | tttttgtatt |
| 6701 | ttagtacaga | cggggtttca | ccatgttggc | caggctggtc | tcgaactcct |
| 6751 | gaccttgtga | tccgactccc | tcggcctctc | aaagtgctag | gaaaacaggc |
| 6801 | aggagccacc | gcgcctggcc | aggttttttct | taaactggca | tttgaacatc |
| 6851 | tggaacaggc | agggagatgt | ctttttttaaa | gtataaatgt | gttttgttac |
| 6901 | atgatttatg | acaattctac | ttgtcttttt | tttttttttt | ttttttgag |
| 6951 | acagagtctt | tctctgtcgg | ccaggctgga | atgcagtggc | acagtctcgg |
| 7001 | ctcacagcag | cctccatctc | ccgggctcaa | gcaattctcc | tgcctcagcc |
| 7051 | tcccaagtag | ctgggattac | agggcgtgtg | ccaccacgcc | cggctaattt |
| 7101 | ttgtattttt | tgtaaagacg | gggtttcacc | atgttggcca | ggctggtctt |
| 7151 | gatctcctga | cctcaggtaa | ttcaccgcc | tcggcctccc | aaagtgctgg |
| 7201 | gattacaggc | ctgagccacc | gtgccttgcc | aacaattcta | cttgtctttt |
| 7251 | aaagttcaat | aaaaatatgt | ggcacgtata | tgggatagta | ccaaactggt |
| 7301 | gcctaaaagc | agtgaaacca | ccattggact | aattggaatg | atttgtctat |
| 7351 | tggctgaaga | tttgaccaca | gagagattct | gctttttttt | ccttgcaggg |
| 7401 | atgaaaaatt | aaaaaaaaaa | aaaagattg | gttccttttt | ctcttcctag |
| 7451 | cctcctgaca | gtaagtagag | agccagaaga | atgatgccaa | ggcatcctgg |
| 7501 | cctgctatgt | ggagaacgct | cttccttac | tgtctcactt | aatagaactc |
| 7551 | ctgttctggc | agtgtcagat | gctgcagcag | caagggaatg | ccattgagtg |
| 7601 | attgcagtaa | gctatgcagc | attttcatgt | ttaaaactac | tgagataata |
| 7651 | aagtgagaac | ttgaggccac | caaatttaa | gttgtaatta | gaaggatttt |
| 7701 | gttaattagg | aatatgagag | tgctacagtg | atcacctgga | atggctccat |
| 7751 | aaatacaaat | gaggtgttaa | ctagtgaagc | aagttgccag | tgtttgtgtg |
| 7801 | tttggtgaga | ctcctaagtt | ctgccatgaa | gttaaagaaa | atattttta |
| 7851 | agattcaaga | aagctgtgtg | aatgaattca | aaattattat | gactgtagat |
| 7901 | ctttttaaaaa | gctatcagta | ttagttttac | tttgattttt | atctaaagag |
| 7951 | aaatacagaa | tgaatactta | cagcattaca | attcaaatgt | gcgtggcttt |
| 8001 | tttttttctt | agttactaga | tatatagtag | taataccttt | atgtaatatt |
| 8051 | ttgaagtaga | gattgaattg | gtataattcc | ctaccttaaa | aatattacac |
| 8101 | aatagcattt | ttgtcatata | ttacgatagc | attttgtgt | actttaccac |
| 8151 | ttaactttttt | ttttcctttt | cttttttttt | tggagacaaa | gtcttgctct |
| 8201 | gtcgcccagg | cgggagtgca | atggcaggat | ctcagctcac | tgcaacctct |
| 8251 | gcctcctggg | tttaagccat | tctcctgcct | cagcctcctg | agtagctggg |
| 8301 | actataggcg | tgtgccacca | cgcccggcta | attttgttt | ttttagtttt |
| 8351 | ttttggagac | ggagtctcgc | tttgtcaccc | acactggagt | gcaaatggca |
| 8401 | tgatctcggc | tcactgcagc | ctccacctcc | tgggttcaag | cgattctctt |
| 8451 | gcctcatgca | ccaccacgcc | cagttaattt | ttgtatattt | agtagagatg |
| 8501 | gggtgtcact | atgttggcca | ggctgccgac | tcaagtgat | cttccctcct |
| 8551 | cagcctccca | aagtgctggg | attacaggca | tgagccactg | ccctggcca |
| 8601 | gtgtcagatg | tttagtttgt | cattaaaatg | gagcaagaat | acataactcg |
| 8651 | tgaggttgta | agattataga | tatgtttact | aatgactgac | tcatagatat |
| 8701 | ccagctgtta | aaactcttca | agaagtaatc | agggcaggcg | gaaatggatg |
| 8751 | taattaacca | aggtcaagca | gtaagttcag | gaaccaggat | aaaaatacag |

Fig. 7d

```
 8801  aattgctccc gagtaagtac tctgttttcc attattctgg ctggaatgca
 8851  ggtaatacag aaagtatatt gcttcctttc attgcttttt ttttcttctt
 8901  ttttcctttt gaggtggagt ttcgctcttg ttgcccaggc tggagtgcga
 8951  tggcatgatc tcggctcacc gcaacctctg cctcctggt  tcaagcaatt
 9001  cttgtgcgtc agcctcctga gtagctggga ttacaggcat gcaccaccat
 9051  gtccagctaa ttttgtatt  tttagtagag acagggtttc accatgttgg
 9101  ctagctggtc tcgaactcct gacctcaggt gatgcatctg cctcggcctc
 9151  ccaaaatgct gggattagag gtgtgggcca cccgcccgg  cccagacctt
 9201  atcttgacta tcttagtcat ttcttctctt gcctgacatg ccctgtgctc
 9251  ctaccaccct ttaaagtggt ttgtgtcata aacatttgat acacaaaaat
 9301  ggaaacttag gacaaatatc ttgatgtctg gtggttgaaa atgtgaactg
 9351  atttggaaat caccggtgtt tctcctctta atctcttctc cattccattc
 9401  aggaaataga ctgtaaggtg ggaaacaagt ataagcagtt agcctcactc
 9451  taaacctgct atgtaataga cattggactg agttctgtct actctctgta
 9501  agcaatccaa ggtaattggc gaaagtggaa ggaatatgta ctcagaagac
 9551  caaaactttg gttttaaat  tgaatatcta ttaagcacaa ggtaacaatt
 9601  cttaccacac acatcagttt tattatttcc cttttacaaa taagacacag
 9651  atgggtagtc agatgtcttt gaggtaacac agcaagtagt taaactgggt
 9701  taagtgatta cccaggttg  agtatggttc caaaatctct tacagtgtca
 9751  ggcaggctac atcagtgcag tatacgtaca tcaggtttca cgaaaaattt
 9801  tttccagaga aaacacaaac ccaaggaacc ttcagtaagt ggtgccttat
 9851  attagtggtt tttagcaaaa ggaagaaact taagtgtttt cctgctgcct
 9901  gacaaaagtg aaaaacagta ttttggtttt tattgaagtt agcatgtatg
 9951  tttgtagctt gcataaaata gtactgaaat ccaattgatt atgaattctt
10001  ggactaacag aacctggatg acaaattaga ggttctggcc tggttgctgg
10051  cttttttagt tgtcttgggt gtaaatttct cagccacacg tggggattgt
10101  gttagataat ctgaaatcta attttcatgg ttttatgatt cagcagcttt
10151  cttcctttga tatttctag  tatttgcttt attatagatt ggaatcctca
10201  aaataacatt gacaagtaga agatacttct gttagtggat ttaaaaaaaa
10251  attacattgg gaatgtcctt tgagtggttg gccctaatcc ctgtcagaag
10301  ctgaaagttg tggatcctaa attcatctgg gcagaatctc acctatgatt
10351  tcagaaagct gagagtttca gagagtgact gtagtcagtc cttagtgagt
10401  acaaaattga gaatacatca ttactttaaa ttaatggtgc agtaactctt
10451  gtgactgata gcaataattt aggtgctttg ttgttagtac ttgattagat
10501  tggattgggt cagttagttt caccaaattg ctaaagacac ctgtcccct
10551  agaattaaaa tactgagtta cataatggct actaaaagga taactatatg
10601  gggtgttcga tgattcaaag gtgaattact tggtctctac cttcaaggaa
10651  tatgatacaa ggcaatatgg tactgccatt agacagatat taacaaagtg
10701  tcttgggact taatagggag ggtagttcca ggctgggaga tgtagtcaga
10751  ttcttttata gagttggcat ttgagttggc ccgtgaaggt tggaaaaagt
10801  tgtgacaggt ggaaaaggag cagggagac  caggacagtg cagtgaaatt
10851  ccagccagga gcagtcatag gcaatgagac agactcatgg agccatgatt
10901  ctcagctgtc ttaccttacc ttagttttcc taaggaatat catggaattc
10951  tgtaaagacc tttaaactaa ataatgttca tatgagatga gtgctaggat
11001  ggggacctgc tgcctaatat aagtagtgtg agtctaaaac attgtggaaa
11051  gtggttagtt taataatgtt attaaagaga caagtctatc acaagggacc
```

Fig. 7e

```
11101  agttaccagt gaaactgtag accacctgat tcactgcgat agggttagcc
11151  aaagggagga gagggcagat tgcatacata gtacctaagg ccactcaaag
11201  acctctttta aaatcacgtg tcatgttgat gacatttgga ggctattaat
11251  gttttcttc ccttttaaga cttagtgttt tctttattag cattaattta
11301  ctctagtaaa caaaattatg tgtgactaaa aatggcaaaa caggctgggc
11351  gcagtggctc acgcctgtaa tcctaacact tgggaggcc aaggcgggtg
11401  gatcactagg tcaggagatc gagaccatcc tggccaacat ggtgaaaccc
11451  cgtctctact aaaatacaaa aaattacctg ggcgtggtgg tgcacgcctg
11501  tagtcccagc tatgtgggag gctgaggcag gggaatcgct tgaacccagg
11551  aggtgaaggt tgcagtgagc caagattggg ccaccgcact ccagcctggg
11601  acagagcgag actccatctc aaaacaaaa aaagatcca aattagaaga
11651  acatggtggc atgcgcctgt agtcccagct acttgggagg ctgaggcagg
11701  agaattactt gaacccggga ggcagaggtt gcagtgagcc gagattgcac
11751  aactacactc cagcctgcgc aacagagcaa gactccatct caaaaaaaaa
11801  aaagaaaga aagaaagaaa gaaactggag ggaacaatgc cctaatgtat
11851  taacaatcat cacatatgag gtgtgaaaat gtgagtggtt ttttttctgat
11901  tttctgtatt ttataacttt tttttgtttg agatggagtc ctgctctgct
11951  gcccaggctg gagcgcagtg ggacgatctc ggctcactgc aacctctgcc
12001  tcccaggttc aagtgattct cctgcctcag cctcctgagt agctgggatt
12051  acaggtgcct gccatatgcc cagctaattt ttttgtatt tttagtagag
12101  acagggtttc accatgttgg ccaggctggt ctcgaactcc tgaccttgtg
12151  attctcccgc ctcaggctcc caaagtgctg ggattacagg catgagccac
12201  tgcgcctggc tataactcct ctgtagtaaa aaatatattc cttcataatt
12251  aatggcacaa tatttaaact ctgaattatt tttaagggat ggtagtggcc
12301  tatgcaaaac tagctgtgga ataatgaatt ttaaaataag cagcatttaa
12351  taaaaataga actatatttt ttttaaaata gaaaagccaa ctagaaggag
12401  atataacaaa atgctaataa tggtgaaaat actggcatca ttcttctctg
12451  cctctcatac tttttcctat gaagtgttga ctaccttttct aaaacacaaa
12501  atcaaaaccg actaaaactc cagactaaca gtttcaaatt atattcagga
12551  ggtttggctg aaagaaggag gaaaggtggg tgtgccctat ttggattcac
12601  acaaaagtag ctccactttt ctccttttt tttttgaga tggagtttcg
12651  ctcttgctgt ccaggctgga gtgcaatggc acgatctcgg ctcaccgcaa
12701  cctccacccc tcagattcaa gcaattctcc tgtctcagtc tcctgagtag
12751  ctgggagtac aggcatgcac caccatgccc agctaatttt gtatgtttag
12801  tggagacggg gtttctccat gttggtcaag ctggtctcta actccctacc
12851  tcaggtgatc cgcccacctc agcctcccaa agtgctggga ttacaggcat
12901  gagccacagt gctgggcctc acttttctcc attttacat ttagggtttg
12951  gcccaagatt gtatttgttc tttggttatc atttgttcaa ctaataagta
13001  actgaaacat gacctgattc aatgaacttc agagcctgcc ccaatcgttc
13051  tgggaaactt caaatatggga aactccttgt ccagactgac agattagcac
13101  ctgccaaagg cagaatcctg caccagccaa tcctgggcac acttccagc
13151  cccaattgta tggcatgggc ctatgattct atcccagttc ttaagaattc
13201  tcagttaaaa tctgggaaca ataattccta cactataagg ctgttatgca
13251  actaagaaaa aaagtaaga gcagttagca tatagcatat ctactcttat
13301  gattattacc aatgaaaggc taaaactgtc acaaacttac ttacgttctt
13351  tttcaaacag ctctctaaca ccaggcaaat cttttgctgc tccaaagtac
```

Fig. 7f

```
13401  ttgtaacctc ggtttcctgg gacttctttt ccttcatgat ccagcatttt
13451  agggccaact ttcttattgg gaagaaaaaa agagaaaatg gatctgttag
13501  ttagttagtt agttattatt tatttattta tttgaggcgg agtctcgctc
13551  tgttgcccat ttatttattt gaggtggagt ctcgctctgt tgcccaggct
13601  ggagtgcagt agcacaatct cactgcaacc tccacctcct gggttcaagt
13651  gattctcctg cctcagcctc ctgagtagct gggattacag gtgcgtgcca
13701  ccacgcctgg ctaatttttg tattttagt agagacgggg tttcaccatg
13751  ttggtcagga tggtcttgaa ctcctgacct catgatccac ccacctcgac
13801  ctcccaaagt gctgggatta caggcgtgag ccaccgcgcc cggcattgtg
13851  gttttttttt ttaatgctgt tgttttttgt ttgtgtgttt gttttcttt
13901  tataataacc ctcaggccat tctatcatag gtctgctgaa gtttgctggg
13951  ggtctggtcc agatcccagt tgccttgttt ttttcccata cctggactta
14001  tcaccagtga agcctttaaa acagcaaaga tagtagcaag ctccttcctg
14051  tggaagttcc atcccggggc ggttctgacc tgttgccaac ccacatgcat
14101  caggaggttg ctggagaccc ccattgggag ggcttaccca gtcaggagga
14151  acagaatcag tgacttaccc aaagaagcag tctgactgct ttttggtaga
14201  gcagttgtgc tgcactctgg gagacccttc cttgtccaga cagcctgtat
14251  tctccacagt ctgcatgctg gagcagctga atcaacagga ccacagagat
14301  ggtggcagcc cttcccccag gaactccatc ccagggagag atcagagttt
14351  tatctgtaga accctggctg gagtggctga agcccctgca aggagatcct
14401  gcccagtgag gaggaatgga tcgggatccc acgaacgggc tgatgaacta
14451  ctgtccatcg atagggcgnn nnnatagatt tcatgatgaa gttgacgcta
14501  gtggtaacaa gttatataga acatgatcgt cctcatatgg cggagtttag
14551  tgagcattgt gttccttttg tgagagtaaa gctttttatt aatgatagag
14601  tgttattttg gtgaggtttt ttagggtgtg gcgagtgtgc gtatagccat
14651  gtcttgaaaa tgggggatgg gattagtatg atcagaaggg agttggggag
14701  gaatcactgg tttgtaaatt gagggggaag ggcctatcta atgcaggaaa
14751  caaggtggcc atgcgggagc tgatcagcag gccaaaattg tggggtgaat
14801  ggagttaatt catagcaggg tttaaagagc ttatgtgggg acagatgaag
14851  atttatcatg gtctagaatc atttcggagc tttgtttgcg tgtcaggccc
14901  cgtgatatgt gcaagagcgc catcagtacg cgtcatggga gcatactgtt
14951  ttcgggatgg gtttcgagcg aagatgtgag cagatactgc tgtcaatggt
15001  gaagccttga ttagaggcac catatgcagt tcttcatgat gctttacatc
15051  cataaaagcc tcggcagcgc ccagcaagag aattcagtgg tgctattcct
15101  tttgaggtgg ggagtggagt atctctcgat cagcgcgtgt ttaccatgcc
15151  ccagtcttag ttatcttcat gttcaaggtt ccggggcaa agtgattctc
15201  ctacctcatc ctctagagta gttatgacta cagagcatgt tatcaccacg
15251  accgggtaat gaaagtatta tagtagattg ggggtttaca ccatgttgga
15301  caggatggta ttaatttcct gacctcatga tccgcctgcc tcccaaagtg
15351  ctgagattac aggcgtgagc caccacgcct gccctaattt tgtgttttta
15401  gtagagatgg agtttcactg tgttggtcag gctgatgtcc aactcctgac
15451  ctcaggtgat cctcctgcct ggcgtccca aagtgctggg attacaggtg
15501  tgagccactg tgcccatcct tgttttgtat tttctaaaag agatgtatct
15551  tgtttaaata ttaaattata agatattcag gccttgcaaa ttgtctggat
15601  tacactgtaa aagtaatcat ttatgtgcaa ataattcctt gagatcaata
15651  gttaaatgag ctcaagctga tctgactaaa ttggagaaga tacaaaatga
```

Fig. 7g

```
15701  agatggggag gaagtggtgc cataagcagc cttttttctt tgaccatttt
15751  atatgccttt tttttttttt ttttgagatg gagtttcact cttgtaaccc
15801  acgttggagt gcaattgctt ggcttgcaac aacctccacc tcccgggttc
15851  aagagattat cctgcctccg cctcctgagt agctgggatt ataggcatga
15901  gccaccaagc ctggctaatt ttgcattttt agtagagacg gggtttctcc
15951  ttcttggtga ggctggtctc gaactcccaa cctcaggtga accatcctcg
16001  tcggcctccc aaagtgctgg gattacaggt gtgagccacc gtgcctgcc
16051  cgccattcgt tttttttttt tttttttttt ttttaattct gactcttctg
16101  tggtggaaac cagcaaatac ttcacataat ttaggatgct aatactagta
16151  cagttaaaag aatgattaca aagcagatac tatttcaaat tctgtaaaaa
16201  tctgttttta atatccttca ctggctgttt gttctgacta gaaatgtttt
16251  gtatatctga aagcaccagt aactcatagc catataattt ttttggtaat
16301  atgttcatag gcaagtggca agagttagta gaaagatttc tctaagaatt
16351  tatcctaaat cagattacac agagttgggg taagtgagta ttgtgttatt
16401  ttcttttgta tatttgacaa tgggaacttt ttgaaactca acttcagtgt
16451  aattttaagt cactaaattt gtccacaagt taatgattaa acagttactg
16501  aaagtggaga accttgccat ttttcggact gcgttttggg tctttggcac
16551  tgtggttagg ttagctaatt cgattatcca ctcaagtttt actcagttgg
16601  aaatatgttt ttctagatga tggtgcctgt gcttaggttt gagaggatat
16651  ttaaaatacg actttgtgtg ccattgtttg acagtggaat taagggtaaa
16701  aatatttaga tatggaagtg tgaaaatgta gttgcattgt tttcattatg
16751  ttctattcca tttcattcta ttttaagaat agcctcaatt tattttttaga
16801  ttgttacata agtacaaaat ccatttgctt tagtgggagt tttattttta
16851  ttttaaaatg ataaccaatt aaaggagttt attatgaaat tctaagtagc
16901  attgtttaaa atgtaaaatt acattacaga aacatttgga aaggggagaa
16951  taaagaaaaa caaaacacaa atgttgccag tgctgtaggt gctattatta
17001  gcgctttggt gtaactcatg gtcgttttcc tactattttt attatacagt
17051  catctcttgg tatctgtgaa gtggttccac aaactccctc aaataccaaa
17101  atcctcctat gctcaagttc ccaatataaa atagtgtagt acttgcatta
17151  caacctttgc acatcttccc atatacttta aaatcatctt tagattactt
17201  ataatccta acacaatgta aatgctgaat aagtagttgt taacattgta
17251  ttgtttaggg aataatggca agaaaagtct gcatgttcaa tacagatgca
17301  actttccac tgaatatttt tattccaagg ttggttgaag ccatggatgc
17351  agaacccatg gatatagagg gcctactgta cttgtaccat ctagagataa
17401  gatttgtatc ttgcatttgt tttaacatat ctgttctaag gaatatctca
17451  gtcaccaggc aagtgctgca gtataactag gtactacgtc aggtgctaag
17501  gttaagagag tattttcctt cactgactcc tcactccgag aatccatttt
17551  acagcttcat tggtttgggt tattccaatt ttttgatgtg agtaaataaa
17601  tgacttctat ttgcccaaaa taaagcttat ataggcctta taaccatgca
17651  aatgtgtcca ttaagttgga cttggaatga gtgaatgagt attactgcca
17701  gtgtgtgtgt gtgtgtgtgt gtgtgtgtgt gtgtgtgtct gtctgtctgt
17751  ctgtctgtct gtctgtctgt ctgtctgcct gcctgcctgc ctgcctgcct
17801  gcctgcctgg ctgcctgtct gcctgtctgc ctgcctgcct gcctgcctgc
17851  ctgcctgtct gtctcacttt gtccctaggc tggagtgca gtggtatgat
17901  ctcggctcac tgcaacctcc acccccgggt tcaagcgat tcttctgcct
17951  cagcctcctg agtagctggg attacaggcg catgccgcca tgcccggctg
```

Fig. 7h

```
18001  ttttttgtat ttttagtaga gacggggttt cgccatgttg gccagactgg
18051  tctcaaactc ctgacctcag atggtccacc cgcttcagcc tcccaaagtg
18101  ctaggattac aggcatgagc caccgtgccc agccactacc aattatttct
18151  cttaatggat tttcattgac cctaaccctg taaattccat cacttttatc
18201  aaggtgtata ttataataag tctataatac ccaatcatgt agttgtgtga
18251  ttattttatt tttttgagac agagtctcaa tgttgcccag gctggagtac
18301  agtggcacca tctcagctca ctgtaagctc cgcctcctgg gttcacacca
18351  ttctcctgcc tcagcctccc aagtagctgg gattacaggc gcctgccact
18401  tcaccggct aatttttgt attttcgta gagacggggt ttcaccatgt
18451  tagccaagat ggtctcgatc tcatgatcca cccacctcgg cctcccaaag
18501  tgatgggatt actggcgtga gccaccatgc ccagctattt ttttaaccaa
18551  tatattagct agcttttttc cccagaataa ttttccaaaa atacatttaa
18601  tagagaataa aagttaaaag aactttcagt ggtttaatgc tgttactttt
18651  aatatttcaa agatctgact gcagccatga gcagcaatga gtgcttcaag
18701  tgtggacgat ctggccactg ggcccgggaa tgtcctactg gtggaggccg
18751  tggtcgtgga atgagaagcc gtggcagagg tggttttacc tcggatagag
18801  gtatttgtc gaatagaaaa atttgaagta cttcagtatt tgttagtatc
18851  aagactggtc tgactagccg aattctttgt ttttgctcaa aacaggtttc
18901  cagtttgttt cctcgtctct tccagacatt tgttatcgct gtggtgagtc
18951  tggtcatctt gccaaggatt gtgatcttca ggaggatggt aagtatttaa
19001  cacttccttt tcatacccct ctagagcttg gagaggtgag cacatgcaac
19051  tgtgtatagc atttccacct ttgaggtttt gtattgtata atttaaaacg
19101  taacactttg taaaggtttt atagtcttgg cctgtttctt ttccttattg
19151  ttgaagcctg ctataactgc ggtagaggtg ccacattgc caaggactgc
19201  aaggagccca agagagagcg agagcaatgc tgctacaact gtggcaaacc
19251  aggccatctg gctcgtgact gcgaccatgc agatgagcag aaatgctatt
19301  cttgtggaga attcggacac attcaaaaag actgcaccaa agtgaagtgc
19351  tataggtaag gtgtcagaat gttgttagaa gaaaactcat tgcagagatt
19401  cttccagaga tgaattagct ataaatggaa gggccttagt aaattcagtg
19451  aaacttagct gtgaccagat aagaccaatt ttcagcatat gtaactggca
19501  gtctatctgt atataattct gtattctgcc ctgatatcct gtggcttatg
19551  gtacctgggc agttttcaca actggacttt tttaatatat aaaagtaaga
19601  gtgttataat ttgaaacttc cagagacttc atagaaagct ctgtaatata
19651  cataaatctt ttatcatgta accagaaatc tttgcctgtt tgtgacatgt
19701  aagtgtataa tttgataaat gttgttgtgt acatatctgt gaaaccttag
19751  gggttaattg catgaaaaca aagatcaggc gttttgttct gcatggtgac
19801  tgttgctttg gtagacagtt ttttctgag gccattgtg aaaacttta
19851  atttcttttt taggtgtggt gaaactggtc atgtagccat caactgcagc
19901  aagacaagtg aagtcaactg ttaccgctgt ggcgagtcag gcaccttgc
19951  acgggaatgc acaattgagg ctacagccta attattttcc tttgtcgccc
20001  ctccttttc tgattgatgg ttgtattatt ttctctgaat cctcttcact
20051  ggccaaggt tggcagatag aggcaactcc caggccagtg agctttactt
20101  gccgtgtaaa aggaggaaag gggtggaaaa aaaccgactt tctgcattta
20151  actacaaaaa aagtttatgt ttagtttggt agaggtgtta tgtataatgc
20201  tttgttaaag aaccccctt ccgtgccact ggtgaatagg gattgatgaa
20251  tgggaagagt tgagtcagac cagtaagccc gtcctgggtt ccttgaacat
```

Fig. 7i

```
20301  gttcccatgt aggaggtaaa accaattctg gaagtgtcta tgaacttcca
20351  taaataactt taattttagt ataatgatgg tcttggattg tctgacctca
20401  gtagctatta aataacatca agtaacatct gtatcaggcc ctacatagaa
20451  catacagttg agtgggagta aacaaaaaga taaacatgcg tgttaatggc
20501  tgttcgagag aaatcggaat aaaagcctaa acaggaacaa cttcatcaca
20551  gtgttgatgt tggacacata gatggtgatg gcaaaggttt agaacacatt
20601  attttcaaag actaaatcta aacccagag taaacatcaa tgctcagagt
20651  tagcataatt tggagctatt caggaattgc agagaaatgc attttcacag
20701  aaatcaagat gttattttg tatactatat cacttagaca actgtgtttc
20751  atttgctgta atcagttttt aaaagtcaga tggaagagc aactgaagtc
20801  ctagaaaata gaaatgtaat tttaaactat tccaataaag ctggaggagg
20851  aagggagtt tgactaaagt tcttttgtt tgtttcaaat tttcattaat
20901  gtatatagtg caaaatacca tattaaagag gggaatgtgg aggactgaaa
20951  gctgacagtt tggactttc tttttgtact taagtcatgt cttcaataat
21001  gaaaattgct gttaaagga tgtatgggat ttagatactt ttgcaaagct
21051  atagaaaatt cactttgtaa tctgttataa taatgcccttt gagttctgtg
21101  ttcagtctga acaggttttt tggtggtggt ggttttgttt tgttttggag
21151  acggagtctc actcttgtcg cccaggctgg agtgcaggct tggctcactg
21201  caacctccac ctcccgggtt caagcaattc tcctgcctca gcctcctgag
21251  tagctgggat tacaggcacc cgccaccacc cccgctaat tttttgtatt
21301  tttatttta ttttattttt ttattttttt ttgagacaga gtgtcgctct
21351  gttgcccagg ctggagtgta gtggtgcgat ctcggctcac tgcaagctcc
21401  gcctcctggg ttcgcgccat tctcctgcct cagcctcctg agtagctggg
21451  gctacaggta cccgccaccg cgcccagcta atttttttt tttgtatttt
21501  tagtaaagac ggggtttcac ggtgttagcc aggatggtct caatctcctg
21551  acctcgtgat ccgcccgcct tggcctccca aagtgctggg atcacaggcg
21601  tgagccaccg cgcccggcct attttttgta tttttagtag agactgggtt
21651  tcatcatgtt ggtcgggctg gtctccaact cctgacctca ggtgatccac
21701  ctgccccgcc ccccaaagtg ctagtgttac aggtgcgagc caccgtgtcc
21751  ggccgattct gaacagtttt aataccattg ctattttgt gttttcctg
21801  ggcctttttt cttttttttt ttttttttg agacagtctc gctctgttgc
21851  ccaggctaga gtgcaatggt gcaatctcag ctcactggaa ccttcacccc
21901  ccacccccac ccctgttca agtaattctc ctgcctcagc ctcccaaata
21951  gctgggatta caggtgtccg ccaccacacc cagctaattt tgttatttt
22001  tagtagagat ggggtttcac tgtgttggtc aggctggtct ccaactgttg
22051  ccctcaggtg agccactgtg ccccacctttt tcctgggttt cataaggatc
22101  tgaagtggtg gattccttgt ttttgctagt atctcattta gagttgagat
22151  ggaccttaaa actcatctgt tttaactcac ttttaatag atgagttaaa
22201  cttaatttac ttaaggatgt acagttagag cctggaactt caaccattat
22251  tcactcccca tgcctgtttt cccccacttt cgaaattaaa tgcggttagc
22301  atcatatagt tcattttccc cctccatgct gctgtgtgat cttgactttt
22351  gggtatgagt ttttcatcct tcatgcaggg ttctgtcagt tcatggtata
```

Fig. 7j

A
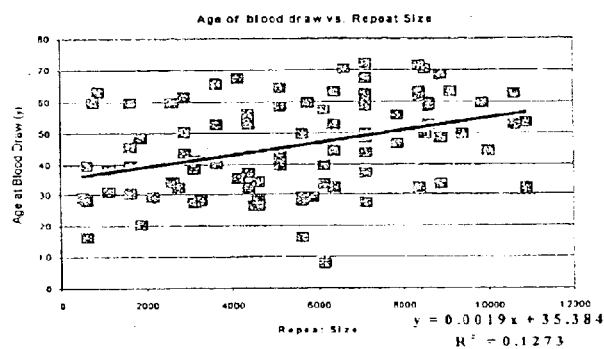
B
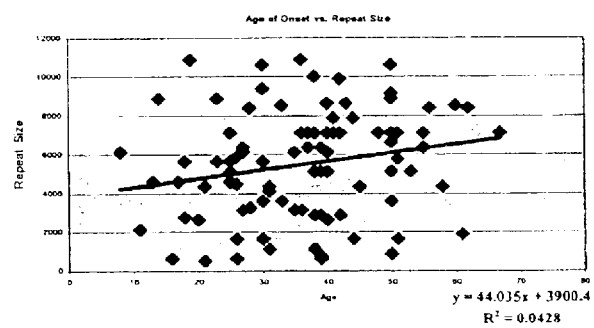
C
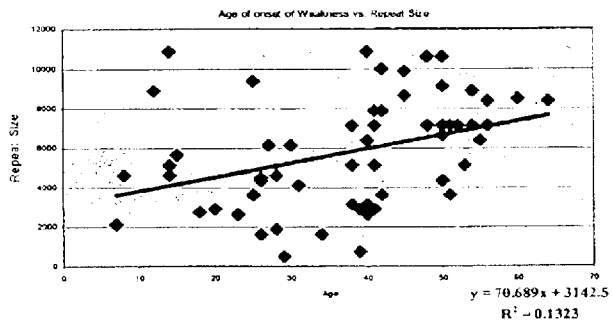
D
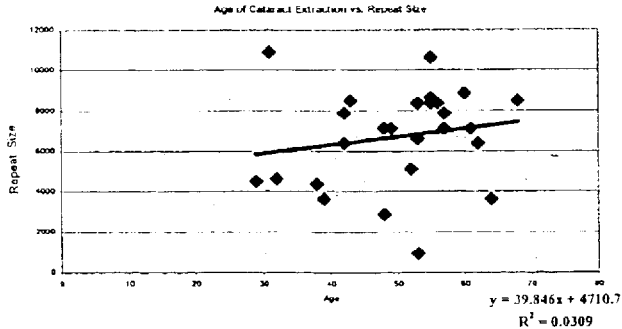
Fig. 8

INTRON ASSOCIATED WITH MYOTONIC DYSTROPHY TYPE 2 AND METHODS OF USE

CONTINUING APPLICATION DATA

This application claims the benefit of U.S. Provisional Application Ser. No. 60/290,365, filed May 11, 2001, U.S. Provisional Application Ser. No. 60/302,022, filed Jun. 29, 2001, and U.S. Provisional Application Ser. No. 60/337,831, filed Nov. 13, 2001, which are incorporated by reference herein.

GOVERNMENT FUNDING

The present invention was made with government support under Grant Number NS35870, awarded by the National Institutes of Health. The Government has certain rights in this invention.

BACKGROUND

DM is a dominantly-inherited, multisystemic disease with a consistent constellation of seemingly unrelated and rare clinical features including: myotonia, muscular dystrophy, cardiac conduction defects, posterior iridescent cataracts, and endocrine disorders (Harper, *Myotonic Dystrophy*, W. B. Saunders, London, ed. 2, 1989)). DM was first described nearly 100 years ago, but the existence of more than one genetic cause was only recognized after genetic testing became available for myotonic dystrophy type 1 (DM1) (Thornton et al., *Ann. Neurology*, 35, 269 (1994), Ricker et al., *Neurology*, 44, 1448 (1994)).

DM1 is caused by an expanded CTG repeat on chromosome 19 that is both in the 3' untranslated region of the dystrophia myotonica-protein kinase (DMPK) gene, and in the promoter region of the immediately adjacent homeodomain gene SIX5 (Groenen and Wieringa, *Bioessays*, 20, 901 (1998), Tapscott, *Science*, 289, 1701 (2000)). How the CTG expansion in a noncoding region of a gene causes the complex DM phenotype remains unclear. Suggested mechanisms include: (i) haploinsufficiency of the DMPK protein; (ii) altered expression of neighboring genes, including SIX5; and (iii) pathogenic effects of the CUG expansion in RNA which accumulates as nuclear foci and disrupts cellular function. Several mouse models have developed different aspects of DM1: a model expressing mRNA with CUG repeats manifests myotonia and the myopathic features of DM1; a DMPK knockout has cardiac abnormalities; and SIX5 knockouts have cataracts. Taken together, these data have been interpreted to suggest that each theory may contribute to DM1 pathogenesis and that DM1 may be a regional gene disorder.

To better define the pathophysiological cause of DM, we have studied families with many of the clinical features of DM but without the DM1 CTG expansion. After genetic testing became available for DM1, families with DM2 and Proximal Myotonic Myopathy (PROMM) were identified and linkage analysis excluded involvement of the DM1 locus, as well as excluding the muscle chloride and sodium channel genes. Proximal Myotonic Dystrophy (PDM) and Myotonic Dystrophy type 2 (DM2) were subsequently described, broadening the recognized phenotype of non-DM 1 forms of dominantly inherited multisystemic myotonic disorders. In 1998 the DM2 locus was mapped to 3q21, and it was demonstrated that the genetic cause of PROMM map to the same locus in many families.

Defining a second human mutation that causes the multisystemic effects of DM, and identifying what is common to these diseases at the molecular level, provides an independent means of determining the pathogenic pathway of DM and allow methods for diagnosing this disease to be developed.

SUMMARY OF THE INVENTION

The present invention represents an advance in the art of detecting whether a human individual is at risk for myotonic dystrophy type 2 (DM2). The inventors have discovered that DM2 is caused by a CCTG expansion in intron 1 of the nucleotides encoding zinc finger protein 9 (ZNF9). This expansion is located in a region of the genome for which the nucleotide sequence was not completely ordered prior to the present invention. The correct sequence of this region has been determined and is disclosed herein. Accordingly, the present invention provides isolated polynucleotides. The polynucleotides include a nucleotide sequence of about nucleotides 1–14468 of SEQ ID NO:1, about nucleotides 14474–22400 of SEQ ID NO:1, about nucleotides 17501–17701 of SEQ ID NO:1, about nucleotides 17501–17701 of SEQ ID NO:1 and a repeat tract, about nucleotides 17858–18058 of SEQ ID NO:1, a repeat tract and about nucleotides 17858–18058 of SEQ ID NO:1, or the complements thereof. The present invention also provides isolated polynucleotides that include at least about 15 consecutive nucleotides from nucleotides 16701–17701 of SEQ ID NO:1, at least about 15 consecutive nucleotides from nucleotides 17858–18862 of SEQ ID NO:1, or the complements thereof.

The present invention provides a method for detecting a polynucleotide that includes a repeat tract within an intron 1 of a zinc finger protein 9 (ZNF9) genomic sequence. The method includes amplifying nucleotides of an intron 1 region of a ZNF9 genomic sequence to form amplified polynucleotides, wherein the amplified polynucleotides includes repeat tracts, and detecting the amplified polynucleotides. Alternatively, the method includes digesting genomic DNA with a restriction endonuclease to obtain polynucleotides, probing the polynucleotides under hybridizing conditions with a detectably labeled probe which hybridizes to a polynucleotide containing a repeat tract within an intron 1 of a ZNF9 genomic sequence, and detecting the probe which has hybridized to the polynucleotides.

The present invention further provides a method for identifying an individual not at risk for developing myotonic dystrophy type 2 (DM2). The method includes analyzing intron 1 regions of ZNF9 genomic sequences of an individual for two not at risk alleles that include repeat tracts of no greater than 176 nucleotides. For instance, the method may include amplifying nucleotides of intron 1 regions of ZNF9 genomic sequences of an individual to form amplified polynucleotides, wherein the amplified polynucleotides include repeat tracts, comparing the size of the amplified polynucleotides, and analyzing the amplified polynucleotides for two not at risk alleles. The act of amplifying may include performing a polymerase chain reaction (PCR) with a primer pair that includes a first primer and a second primer, wherein the first primer and the second primer flank the repeat tracts located within the intron 1 regions. The first primer includes at least about 15 nucleotides selected from nucleotides 14469–17701 of SEQ ID NO:1, and the second primer includes at least about 15 nucleotides selected from nucleotides 17858–18661 of SEQ ID NO: 1. Alternatively, the method may include amplifying nucleotides of intron 1 regions within ZNF9 genomic sequences of an individual to form amplified polynucleotides, wherein the amplified polynucleotides include repeat tracts, and analyzing the repeat tracts of the amplified polynucleotides for two not at risk alleles including repeat tracts of no greater than 176 nucleotides.

Also provided by the present invention is a method for identifying an individual that has DM2 or is at risk for developing DM2. The method includes analyzing an intron 1 region of a ZNF9 genomic sequence of an individual for one at risk allele including a repeat tract including at least about 75 CCTG repeats. In another aspect, the method includes digesting genomic DNA of an individual with a restriction endonuclease to obtain polynucleotides, probing the polynucleotides under hybridizing conditions with a detectably labeled probe that hybridizes to a polynucleotide containing a repeat tract within an intron 1 of a ZNF9 genomic sequence, detecting the probe that has hybridized to the polynucleotide, and analyzing the intron 1 region of the hybridized polynucleotide for one at risk allele including a repeat tract including at least about 75 CCTG repeats. In yet another aspect, the method includes amplifying nucleotides of an intron 1 region of a ZNF9 genomic sequence of an individual to form amplified polynucleotides, wherein the amplified polynucleotides include a repeat tract, and analyzing the repeat tracts of the amplified polynucleotides for one at risk allele including a repeat tract including at least about 75 CCTG repeats.

The present invention also provides kits. In one aspect of the invention, the kit is for identifying whether an individual is not at risk for developing DM2. The kit includes a first primer having at least about 15 consecutive nucleotides selected from nucleotides 14469–17701 of SEQ ID NO:1, and the second primer having at least about 15 consecutive nucleotides selected from nucleotides 17858–18661 of SEQ ID NO:1. An individual who is not at risk has two not at risk alleles of ZNF9 genomic sequences including repeat tracts of no greater than 176 nucleotides.

In another aspect, the kit is for identifying whether an individual is at risk for developing DM2. The kit includes a probe having at least about 200 nucleotides, wherein the probe hybridizes to SEQ ID NO:1 or the complement thereof. An individual who is at risk has one at risk allele of a ZNF9 genomic sequence including a repeat tract including at least about 75 CCTG repeats. Alternatively, the kit includes a first primer having at least about 15 nucleotides selected from nucleotides 14469–17701 of SEQ ID NO:1 or nucleotides 17858–18661 of SEQ ID NO:1, and a second primer having a nucleotide sequence selected from the group consisting of $(CCTG)_n$ and $(CAGG)_n$, where n is at least 4. An individual who is at risk has one at risk allele of a ZNF9 genomic sequence including a repeat tract including at least about 75 CCTG repeats.

In yet another aspect, the kit is for identifying whether an individual has DM2. The kit includes a probe having at least about 200 nucleotides, wherein the probe hybridizes to SEQ ID NO:1 or the complement thereof. An individual who is at risk has one at risk allele of a ZNF9 genomic sequence including a repeat tract including at least about 75 CCTG repeats, and displays a symptom of DM2. Alternatively, the kit includes a first primer including at least about 15 nucleotides selected from nucleotides 14469–17701 of SEQ ID NO: 1 or nucleotides 17858–18661 of SEQ ID NO: 1, and a second primer including a nucleotide sequence selected from the group consisting of $(CCTG)_n$ and $(CAGG)_n$, where n is at least 4. An individual who is at risk has one at risk allele of a ZNF9 genomic sequence including a repeat tract including at least about 75 CCTG repeats.

Unless otherwise specified, "a," "an," "the," and "at least one" are used interchangeably and mean one or more than one.

FIG. 7. Nucleotide sequence of a human zinc finger protein 9 (ZNF9) genomic sequence (SEQ ID NO:1). N, nucleotide A, C, T, or G.

FIG. 8. Correlation of Repeat Length with Clinical Severity.

Figure 9:
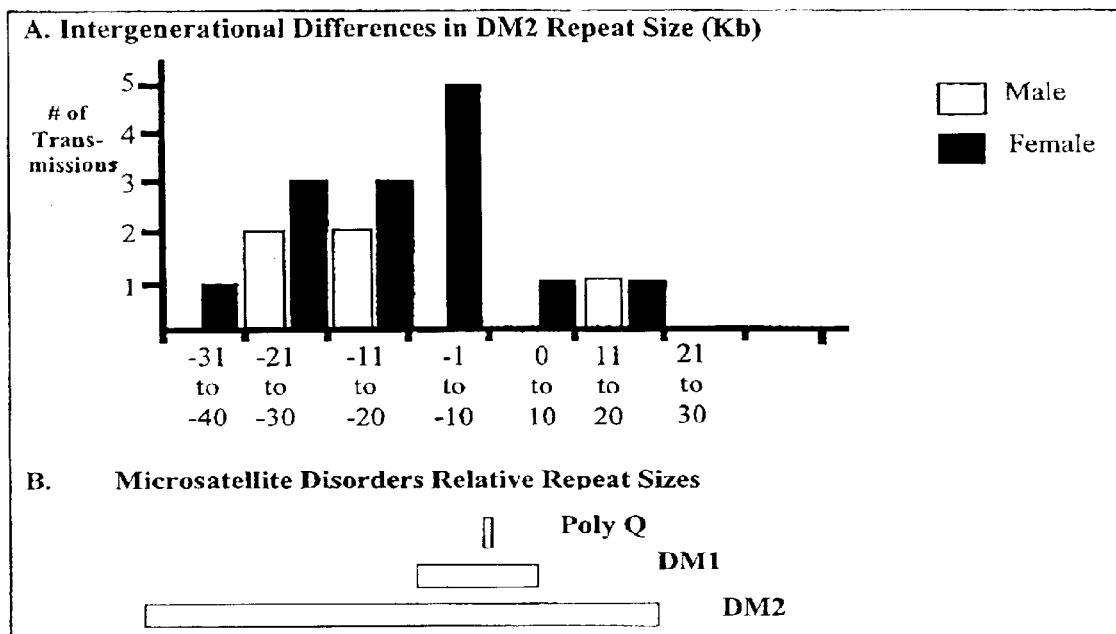

FIG. 9. Intergenerational changes in repeat length.

DETAILED DESCRIPTION OF PREFERRED EMBODIMENTS OF THE INVENTION

Compositions

The present invention provides isolated polynucleotides that include a portion of an intron 1 region of a zinc finger protein 9 (ZNF9) genomic sequence. As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including, for instance, genomic sequences, and other sequences such as regulatory sequences and/or introns. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities. As used herein, a "genomic sequence" includes a polynucleotide that encodes an unprocessed preRNA (i.e., an RNA molecule that includes both exons and introns), and the preRNA. When placed under the control of appropriate regulatory sequences, a genomic sequence produces an mRNA. The boundaries of a genomic sequence are generally determined by a transcription initiation site at its 5' end and a transcription terminator at its 3' end. A genomic sequence typically includes introns and exons. A regulatory sequence is a polynucleotide that regulates expression of a genomic sequence to which it is operably linked. A non-limiting example of a regulatory sequence includes promoters. "Operably linked" refers to a juxtaposition wherein the components so described are in a relationship permitting them to function in their intended manner. A regulatory sequence is "operably linked" to a genomic sequence when it is joined in such a way that expression of the genomic sequence is achieved under conditions compatible with the regulatory sequence.

Figure 4:
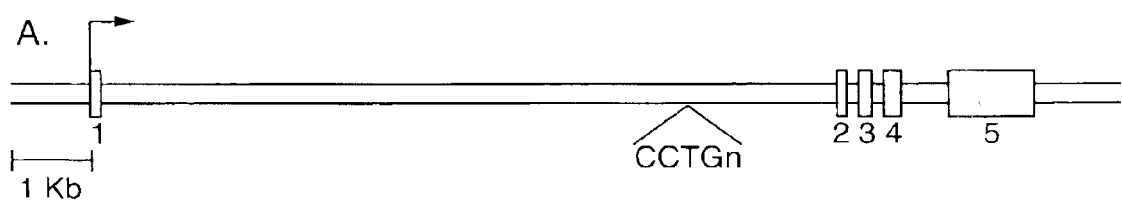
FIG. 4. Genomic organization of the ZNF9 gene. The position of the DM2 expansion in intron 1 is shown. The gene spans 16.5 kb of genomic sequence with an mRNA of 1.5 kb.

The ZNF9 genomic sequence maps to chromosome 3, position 3q21, in the human genome. The sequence tagged sites (STS) associated with the ZNF9 genomic sequence include N22238 and stG51107. The polypeptide encoded by the ZNF9 genomic sequence contains 7 zinc finger domains and functions as an RNA-binding polypeptide by binding the sterol regulatory element (see Rajavashisth et al. *Science*, 245, 640–643). As used herein, a "polypeptide" refers to a polymer of amino acids linked by peptide bonds and does not refer to a specific length of a polymer of amino acids. The ZNF9 genomic sequence contains 5 exons and 4 introns (see FIG. 4).

The sequence of a ZNF9 genomic sequence obtained from one individual is disclosed in FIG. 7. In this sequence, exon 1 corresponds to nucleotides 4337–4415, exon 2 corresponds to nucleotides 18662–18799, exon 3 corresponds to nucleotides 78896–18987, exon 4 corresponds to nucleotides 19156–19356, and exon 5 corresponds to nucleotides 19865–20845. Intron 1, which corresponds to nucleotides 4416–18661, includes a gap of unknown size. This gap is depicted in SEQ ID NO:1 between nucleotides 14469–14473. An intron 1 of a ZNF9 genomic sequence includes a TG/TCTG/CCTG repeat tract, which is also referred to herein as a "repeat tract." The characteristics of repeat tracts are described in greater detail below. In SEQ ID NO:1, the repeat tract corresponds to nucleotides 17702–17858. In the ZNF9 genomic sequence, the transcription initiation site is nucleotide 4337, the first nucleotide of exon 1, and the transcription termination site is nucleotide 20845.

An intron 1 of a ZNF9 genomic sequence typically includes at least about 14247 nucleotides. The sequences of an intron 1 immediately adjacent to exon 1 (i.e., the 5' end of intron 1) are preferably nucleotides 4416–4426 of SEQ ID NO:1, more preferably nucleotides 4416–4466 of SEQ ID NO:1, most preferably nucleotides 4416–4516 of SEQ ID NO:1. The sequences of an intron 1 immediately adjacent to exon 2 (i.e., the 3' end of intron 1) are preferably nucleotides 18641–18661 of SEQ ID NO:1, more preferably nucleotides 18611–18661 of SEQ ID NO: 1, most preferably nucleotides 18561–18661 of SEQ ID NO: 1. Intron 1 of a ZNF9 genomic sequence also includes several nucleotide sequences that are highly conserved by intron 1 regions present in different alleles of ZNF9, and preferably are not present elsewhere in the human genome. For instance, an intron 1 of a ZNF9 genomic sequence contains one, preferably two, more preferably 3, most preferably, 4 of the following: GCCGCAGTGCGGGTCGGGTCTGTGGCGGAC (SEQ ID NO:39), the nucleotide sequence generated by using the primers GAGAACCTTGCCATTTTTCG (SEQ ID NO:22) and CACCTACAGCACTGGCAACA (SEQ ID NO:23) to amplify an intron 1 of ZNF9, preferably SEQ ID NO:1, GCCTAGGGGACAAAGTGAGA (SEQ ID NO:10), GGCCTTATAACCATGCAAATG (SEQ ID NO:11), or the complements thereof.

Examples of the polynucleotides of the present invention include polynucleotides located upstream (i.e., 5') or downstream (i.e., 3') of the repeat tract. Polynucleotides of the present invention located upstream of the repeat tract preferably include, in increasing order of preference, about nucleotides 17501–17701 of SEQ ID NO:1, about nucleotides 17101–17701 of SEQ ID NO:1, about nucleotides 16701–17701 of SEQ ID NO:1, most preferably, about nucleotides 15701–17701 of SEQ ID NO:1, or the complements thereof. Polynucleotides of the present invention located downstream of the repeat tract preferably include, in increasing order of preference, about nucleotides 17858–18058 of SEQ ID NO:1, about nucleotides 17858–18458 of SEQ ID NO:1, about nucleotides 17858–18858 of SEQ ID NO:1, most preferably, about nucleotides 17858–19858 of SEQ ID NO:1, or the complements thereof.

Optionally and preferably, the polynucleotides of the invention that include a portion of SEQ ID NO:1 further include a repeat tract, or the complements thereof. More preferably, the polynucleotides of the invention include the repeat tract and polynucleotides located upstream and downstream of the repeat tract. The upstream nucleotide of such polynucleotides can begin at, in increasing order of preference, about nucleotide 17501, about nucleotide 17101, about nucleotide 16701, most preferably, about nucleotide 15701 of SEQ ID NO:1. The downstream nucleotide of such polynucleotides can end at, in increasing order of preference, about nucleotide 18058, about nucleotide 18458, about nucleotide 18858, most preferably, about nucleotide 19858 of SEQ ID NO:1.

The present invention also includes shorter polynucleotides, also referred to herein as primers and probes. A polynucleotide of this aspect of the invention has a nucleotide sequence that is complementary to a nucleotide sequence of a ZNF9 genomic sequence, or the complement thereof. Preferably, such a polynucleotide includes a nucleotide sequence of the intron 1 that flanks the repeat tract, exon 2, or the complements thereof, and optionally, further includes nucleotides of the repeat tract and the complements thereof. In some embodiments, a polynucleotide of this aspect of the invention includes consecutive nucleotides selected from about nucleotides 15701–16700 of SEQ ID NO:1, about nucleotides 16701–17100 of SEQ ID NO:1, about nucleotides 17101–17500 of SEQ ID NO:1, about nucleotides 17501–17701 of SEQ ID NO:1, about nucleotides 17858–18058 of SEQ ID NO:1, about nucleotides 18059–18458 of SEQ ID NO:1, about nucleotides 18459–18858 of SEQ ID NO:1, about nucleotides 18859–19858 of SEQ ID NO:1, SEQ ID NO:2, SEQ ID NO:3, SEQ ID NO:4, SEQ ID NO:5, or the complements thereof. A polynucleotide of this aspect of the invention includes, in increasing order of preference, at least about 15 consecutive nucleotides, at least about 20 consecutive nucleotides, at least about 25 consecutive nucleotides, at least about 200 nucleotides, at least about 350 nucleotides, most preferably, at least about 500 nucleotides.

Methods

The identification of a genomic sequence that is associated with a disease allows for improved diagnosis of the disease. The present invention discloses that an expansion in the intron 1 of a ZNF9 genomic sequence is associated with the disease myotonic dystrophy type 2 (DM2). The expansion occurs in a TG/TCTG/CCTG repeat tract, also referred to herein as a "repeat tract." A repeat tract begins with at least about 14 consecutive TG nucleotides (i.e., the TG dinucleotide repeated 14 times), followed by at least about 3 consecutive TCTG nucleotides, followed by at least about 4 consecutive CCTG nucleotides. A "normal" repeat tract, also referred to herein as a "not at risk" repeat tract, includes no greater than about 176 nucleotides, more preferably no greater than 164, most preferably, no greater than 154 nucleotides, where the total number of nucleotides is determined by counting from the first nucleotide of the first TG to the last nucleotide of the last CCTG. When greater than 4 consecutive CCTG nucleotides are present in a repeat tract, preferably a normal repeat tract, intervening GCTG and/or TCTG nucleotides may also be present. Examples of normal repeat tracts are depicted at SEQ ID NO:2, SEQ ID NO:3, and SEQ ID NO:4 (see FIG. 2B) and at nucleotides 17702–17857 of SEQ ID NO:1. A ZNF9 genomic sequence containing a normal repeat tract is referred to herein as a "normal allele." As used herein, an "allele" of ZNF9 refers to one of several alternative forms of the nucleotide sequence that occupies the location of the ZNF9 genomic sequence on chromosome 3, position 3q21. An individual with two "normal" or "not at risk" alleles of ZNF9 will not display symptoms of DM2 during his or her lifetime, and is considered to be "not at risk."

An "at risk" repeat tract of a ZNF9 genomic sequence also includes consecutive TG nucleotides, preferably about 16, followed by consecutive TCTG nucleotides, preferably about 9, followed by consecutive CCTG nucleotides. The number of consecutive CCTG nucleotides, also referred to herein as "a CCTG repeat," is at least about 75 (i.e., the four nucleotides CCTG repeated at least about 75 times), more preferably at least about 100, most preferably, at least about 500. Typically, a CCTG repeat of an at risk allele is uninterrupted in that there are no other nucleotides present in the CCTG repeat. An example of an at risk repeat tract is depicted at SEQ ID NO:5 (see FIG. 2B). As used herein, "at risk" describes an individual having an allele of the ZNF9 genomic sequence that is associated with DM2. Herein, this includes an individual who may be manifesting at least one symptom of DM2, as well as an individual who may develop at least one symptom of DM2 in the future. An allele of the ZNF9 genomic sequence that is associated with DM2 is referred to herein as an "at risk allele." This mutation is dominant, thus an individual with an at risk allele of ZNF9 may display at least one symptom of DM2 during his or her lifetime. Typically, individuals have either two normal alleles or one normal allele and one at risk allele.

The present invention includes methods for detecting a polynucleotide including a repeat tract within an intron 1 of a ZNF9 genomic sequence, methods for identifying an individual not at risk for developing DM2, and methods for identifying an individual that has or is at risk for developing DM2. The methods of the present invention can involve known methods for detecting a specific polynucleotide, including detection of DNA or RNA, preferably, DNA. For instance, polymerase chain reaction (PCR) techniques can be used with primers that amplify all or a portion of a repeat tract. Alternatively, Southern blotting hybridization techniques using labeled probes can be used. The source of polynucleotides is a biological sample that includes genomic DNA and/or unprocessed RNA, preferably genomic DNA. As used herein, a "biological sample" refers to a sample of material (solid or fluid) obtained from an individual, including but not limited to, for example, blood, plasma, serum, or tissue. An individual can be a rat, mouse, human, chimpanzee, or gorilla, preferably human. Typically, the number of nucleotides in a repeat tract, including the number of CCTG repeats in a repeat tract, can be inferred by the approximate molecular weight of the detected polynucleotide containing the repeat tract. Other techniques, including nucleic acid sequencing, can also be used for determining the number of nucleotides in a repeat tract.

The present invention provides methods for detecting a polynucleotide including at least a portion of a repeat tract within an intron 1 of a ZNF9 genomic sequence. Preferably, the polynucleotide includes an entire repeat tract within an intron 1 of a ZNF9 genomic sequence. In one aspect, the method includes amplifying nucleotides within an intron 1 region of a ZNF9 genomic sequence of an individual to form amplified polynucleotides that include a repeat tract, and detecting the amplified polynucleotides. Preferably, nucleotides are amplified by PCR. In PCR, a molar excess of a primer pair is added to a biological sample that includes polynucleotides, preferably genomic DNA. The primers are extended to form complementary primer extension products which act as template for synthesizing the desired amplified polynucleotides. As used herein, the term "primer pair" means two oligonucleotides designed to flank a region of a polynucleotide to be amplified. One primer is complementary to nucleotides present on the sense strand at one end of a polynucleotide to be amplified and another primer is complementary to nucleotides present on the antisense strand at the other end of the polynucleotide to be amplified. The polynucleotide to be amplified can be referred to as the template polynucleotide. The nucleotides of a polynucleotide to which a primer is complementary is referred to as a target sequence. A primer can have at least about 15 nucleotides, preferably, at least about 20 nucleotides, most preferably, at least about 25 nucleotides. Typically, a primer has at least about 95% sequence identity, preferably at least about 97% sequence identity, most preferably, about 100% sequence identity with the target sequence to which the primer hybridizes. The conditions for amplifying a polynucleotide by PCR vary depending on the nucleotide sequence of primers used, and methods for determining such conditions are routine in the art.

The methods that include amplifying nucleotides within an intron 1 region of a ZNF9 genomic sequence may be used to identify an individual not at risk for developing DM2. In this aspect, the primer pair includes primers that flank a repeat tract. The first primer includes at least about 15 consecutive nucleotides selected from about nucleotides 17501–17701 of SEQ ID NO:1, about nucleotides 17101–17701 of SEQ ID NO:1, about nucleotides 16701–17701 of SEQ ID NO:1, most preferably, about nucleotides 15701–17701 of SEQ ID NO:1. The second primer includes at least about 15 consecutive nucleotides selected from the complement of about nucleotides 17858–18058 of SEQ ID NO:1, about nucleotides 17858–18458 of SEQ ID NO:1, about nucleotides 17858–18858 of SEQ ID NO:1, most preferably, about nucleotides 17858–19858 of SEQ ID NO:1. In a preferred embodiment of this aspect of the invention, one primer includes the nucleotide sequence GGCCTTATAACCATG-CAAATG (SEQ ID NO:11) and the second primer includes the nucleotide sequence GCCTAGGGGACAAAGTGAGA (SEQ ID NO:10).

After amplification, the sizes of the amplified polynucleotides may be determined, for instance by gel electrophoresis, and compared. The amplified polynucleotides can be visualized by staining (e.g., with ethidium bromide) or labeling with a suitable label known to those skilled in the art, including radioactive and nonradioactive labels. Typical radioactive labels include $^{33}$P. Nonradioactive labels include, for example, ligands such as biotin or digoxigenin as well as enzymes such as phosphatase or peroxidases, or the various chemiluminescers such as luciferin, or fluorescent compounds like fluorescein and its derivatives.

Due to the size of the expansion of CCTG repeats in an at risk allele, this method of amplifying nucleotides within an intron 1 region of a ZNF9 genomic sequence typically does not result in detectable amplified polynucleotides from an at risk allele. Thus, when the comparison of the sizes of the amplified polynucleotides indicates the presence of two polynucleotides, both copies of the individual's repeat tracts were amplified and the individual is considered to be not at risk (see, for instance, FIG. 6B, lane 1). When only one amplified polynucleotide is present after amplification as described above, it is not possible to conclude that the individual is not at risk (see, for instance, FIG. 6B, lanes 2 and 3).

Instead of comparing the sizes of the amplified polynucleotides after amplification, the size of the repeat tracts of the amplified polynucleotides may be determined by, for instance, inferring the size of the repeat tract based on the observed molecular weight of the amplified polynucleotides, or by determining the nucleotide sequence of the repeat tract. The presence of repeat tracts having no greater than 176 nucleotides, and no repeat tract having at least about 75 CCTG repeats, indicates the individual is not at risk. The presence of a repeat tract having at least about 75 CCTG repeats indicates the individual is at risk.

Alternatively, the methods that include amplifying nucleotides within an intron 1 region of a ZNF9 genomic sequence may be used to identify an individual that has or is at risk for developing DM2. In this aspect, the primer pair includes a first primer having a target sequence that does not include the repeat tract. The first primer includes at least about 15 consecutive nucleotides located either upstream or downstream of a repeat tract. When selected from nucleotides upstream of a repeat tract, the nucleotides are, in increasing order of preference, about nucleotides 17501–17701 of SEQ ID NO:1, about nucleotides 17101–17701 of SEQ ID NO:1, about nucleotides 16701–17701 of SEQ ID NO:1, most preferably, about nucleotides 15701–17701 of SEQ ID NO:1. When selected from nucleotides downstream of a repeat tract, the nucleotides are, in increasing order of preference, the complement of about nucleotides 17858–18058 of SEQ ID NO:1, about nucleotides 17858–18458 of SEQ ID NO:1, about nucleotides 17858–18858 of SEQ ID NO:1, most preferably, about nucleotides 17858–19858 of SEQ ID NO:1. The second primer of the primer pair includes either $(CCTG)_n$ or $(CAGG)_n$, where n is at least 4, preferably, at least 5. The second primer binds randomly at multiple sites within a repeat tract, which results in amplified polynucleotides that vary in size but are larger than the amplified polynucleotides that contain a normal allele. Thus, after determining the sizes of the amplified polynucleotides, the presence of one amplified polynucleotide and a population of amplified polynucleotides having a range of sizes that are greater than the one amplified polynucleotide indicates the individual has an at risk allele, and is considered to be at risk (see FIG. 6D and Example 2).

Optionally and preferably, the second primer of this aspect of the invention is modified to increase the efficiency of the amplification. The modification includes adding an additional nucleotide sequence present at the 5' end of the second primer. Such a nucleotide sequence is referred to herein as a "hanging tail" sequence. A hanging tail sequence includes at least about 20 nucleotides, more preferably at least about 22 nucleotides, and negligible complementarity to any nucleotide sequences in the human genome. Whether a hanging tail has negligible complementarity to any nucleotide sequences in the human genome can be determined by hybridizing the hanging tail sequence with the human genome under the hybridization conditions described herein. A hanging tail has negligible complementarity to any nucleotide sequences in the human genome when it does not hybridize to the human genome. When the second primer of this aspect of the invention is modified in this way, the amplification also includes a third primer having a nucleotide sequence such that it is complementary to the hanging tail nucleotide sequence when incorporated into an amplified polynucleotide. In a preferred embodiment of this aspect of the invention, the first primer is CL3N58-D R (5'-GGCCTTATAACCATGCAAATG (SEQ ID NO:11)), the second primer is JJP4CAGG (5'-TACGCATCCGAGTTTGAGACGCAGGCAG-GCAGGCAGGCAGG (SEQ ID NO:36)), and the third primer is JJP3(5'-TACGCATCCGAGTTTGAGACG (SEQ ID NO:37)).

In another aspect of the methods for detecting a polynucleotide including a repeat tract within an intron 1 of a ZNF9 genomic sequence, polynucleotide probes are used that hybridize to a polynucleotide. As used herein, "hybridizes," "hybridizing," and "hybridization" means that a probe forms a noncovalent interaction with a target polynucleotide under standard conditions. Standard hybridizing conditions are those conditions that allow a probe to hybridize to a target polynucleotide. Such conditions are readily determined for a probe and the target polynucleotide using techniques well known to the art, for example see Sambrook et al. *Molecular Cloning: A Laboratory Manual*; Cold Spring Harbor Laboratory: New York (1989). Preferred probes useful in the present invention hybridize to a target polynucleotide by using prehybridization in a hybridization buffer, preferably RAPID-HYB buffer (Amersham, Piscataway, N.J.), at 60° for 1 hour, and hybridization overnight at 60° C. Preferably, at least 4×10 counts per minute (cpm) total of the labeled probe is used in the hybridization. When the probe used is at least about 200 nucleotides, the wash conditions used are: 2 washes for 5 minutes each at room temperature in a solution containing 2× SSC (one liter of 20× SSC contains 175.3 grams NaCl and 88.2 grams sodium citrate, pH 7.0) and 0.05% sodium dodecyl sulfate (SDS), followed by 2 to 3 washes for 30 minutes each at 52° in a solution containing 0.15× SSC and 0.1% SDS. Other hybridization conditions for use when the probe is at least about 200 nucleotides use the same prehybridization and hybridization conditions as described above, but the wash conditions used are: 2 washes for 5 minutes each at room temperature in a solution containing 2× SSC and 0.05% SDS, followed by 1 wash for 15 minutes at 50° C. in a solution containing 0.15× SSC and 0.1% SDS, followed by 1 wash for 10 minutes at 50° C. in a solution containing 0.15× SSC and 0.1% SDS. When the probe used is about 20 to about 22 nucleotides, the same prehybridization and hybridization conditions described above are used, but the wash conditions used are: two 15 minute washes at 45° C. in 2× SSC and 0.1% SDS. The nucleotide sequence of a target DNA molecule is generally a sequence complementary to the probe. The hybridizing probe may contain 1 to 10 nonhybridizing nucleotides, preferably no greater than 5, more preferably no greater than 2 nonhybridizing nucleotides, that do not interfere with forming the noncovalent interaction. The nonhybridizing nucleotides of a probe may be located at an end or within the hybridizing probe. Thus, a probe does not have to be complementary to all the nucleotides of the target DNA sequence as long as there is hybridization under standard hybridization conditions. In increasing order of preference, a probe has at least about 20 nucleotides, at least about 200 nucleotides, at least about 350 nucleotides, most preferably at least about 500 nucleotides. Preferred polynucleotides useful in this aspect of the invention include TTGGACTTGGAATGAGT-GAATG (SEQ ID NO:38), and nucleotides 16507–16992 of SEQ ID NO:1.

In one embodiment of this aspect of the invention, the methods include identifying an individual that has or is at risk for developing DM2. The method includes digesting genomic DNA of an individual with a restriction endonuclease to obtain polynucleotides, and probing the polynucleotides under hybridizing conditions with a detectably labeled probe. The digestion of genomic DNA with endonucleases is routine in the art, and numerous endonucleases are known. Preferred restriction endonuclease enzymes include EcoRI and BsoBI. Typically, the polynucleotides resulting from digestion are fractionated, for instance by gel electrophoresis, denatured to yield single stranded polynucleotides, and then exposed to the probe under hybridizing conditions. The probe that has hybridized to the polynucleotide is then detected, and the size of the hybridized polynucleotide may then be determined. The repeat tract may then be characterized, preferably by determining the number of CCTG repeats in the repeat tract. Typically, the number of nucleotides in a repeat tract, including the number of CCTG repeats in a repeat tract, can be inferred by the approximate molecular weight of the detected polynucleotide containing the repeat tract. The presence of one repeat tract having at least about 75 CCTG repeats indicates the individual is at risk.

In another embodiment of this aspect of the invention, polynucleotides may be used for in situ hybridization of tissue samples, preferably muscle tissue or fibroblasts, more preferably muscle tissue. Preferably, the muscle tissue is skeletal muscle. This method routine and known in the art (see, for instance, Taneja et al., *J. Cell. Biol.*, 128, 995–1002 (2002)). Preferred polynucleotides useful in this aspect of the invention include $(CAGG)_n$, where n is at least 4, preferably, at least 5. Preferably, such a polynucleotide includes a fluorescent label. The cells of an individual having an at risk allele will include numerous nuclei containing the fluorescent labeled polynucleotide, while the cells of an individual not having an at risk allele will not include nuclei containing the fluorescent labeled polynucleotide.

The present invention also provides a kit for identifying whether an individual as at risk or not at risk for developing DM2. The kit includes the primers and/or probes discussed above in a suitable packaging material in an amount sufficient for at least one assay. Optionally, other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polynucleotides can be used for identifying whether an individual as at risk or not at risk for developing DM2. In addition, the packaging material contains instructions indicating how the materials within the kit are employed. As used herein, the term "package" refers to a solid matrix or material such as glass, plastic, paper, foil, and the like, capable of holding within fixed limits the primers and/or probes. Thus, for example, a package can be a glass vial used to contain milligram quantities of a primer pair. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

Identification of the Molecular Basis for Myotonic Dystrophy Type 2

The myotonic dystrophy type 2 locus (also referred to as proximal myotonic myopathy (PROMM) locus) was previously mapped to chromosome 3q21 (Ranum et al., *Nature Genet.*, 19, 196 (1998), Day et al., *Neuromuscul. Disord.*, 9, 19 (1999)). Positional cloning was used to identify the DM2 mutation. We identified, obtained informed consent, performed neurological exams, and collected blood samples from DM2/PROMM family members. Genomic DNA was isolated from blood using the Puregene kit #D-5000 (Gentra Systems., Minneapolis, Minn.). Linkage analysis was performed using the LINKAGE package of computer programs (version 5.1) (Lathrop et al., *Proc. Natl. Acad. Sci. U.S.A.* 81, 3443 (1984)).

The DM2 region was narrowed to a 2 centiMorgan (cM) interval by analyzing 10 recombinant chromosomes (Ranum et al., *Nature Genet.*, 19, 196 (1998)). Sequence data from this region, which is partially covered by 14 BACs, was used to develop 80 short tandem repeat (STR) markers. The sequence data was from McPherson et al., (*Nature* 409, 934 (2001)), and BACs spanning the DM2 region were identified and ordered by sequence tagged site (STS) content mapping. Additional polymorphic STR markers were developed using di-, tri-, and tetranucleotide repeat sequences that mapped to the region (McPherson et al., *Nature* 409, 934–41 (2001)). PCR primers for the following markers were as follows:

```
                                          (SEQ ID NO:6)
CL3N49 (CL3N49 F 5'-GTGTGTGTGCATTTGTGTGC, (SEQ ID NO:7)
CL3N49 R 5'-GAGGTTGCAGTGAGCTGAATC);

(SEQ ID NO:8)
CL3N88 (CL3N88 F 5'-AGCTGACCCTTGTCTTCCAG, (SEQ ID NO:9)
CL3N88 R 5'-CAAACAAACCCAGTCCTCGT);

(SEQ ID NO:10)
CL3N58 (CL3N58-D F 5'-GCCTAGGGGACAAAGTGAGA, (SEQ ID NO:11)
CL3N58-D R 5'-GGCCTTATAACCATGCAAATG);

(SEQ ID NO:12)
CL3N59 (CL3N59 F 5'-GCTGGCACCTTTTACAGGAA, (SEQ ID NO:13)
CL3N59 R 5'-ATTTGCCACATCTTCCCATC);

(SEQ ID NO:14)
CL3N83 (CL3N83 F 5'-GTGTGTAAGGGGGAGACTGG, (SEQ ID NO:15)
CL3N83 R 5'-AAGCCCAAGTGGCATTCTTA);

(SEQ ID NO:16)
CL3N84 (CL3N84 F 5'-TCATTCCCAGACGTCCTTTC,

-continued
                                          (SEQ ID NO:17)
CL3N84 R 5'-AATCGCTTGAACCTGGAAGA);

(SEQ ID NO:18)
CL3N99 (CL3N99 F 5'-CTGCCGGTGGGTTTTAAGT, (SEQ ID NO:19)
CL3N99 R 5'-TGCAAGACGGTTTGAAGAGA);

(SEQ ID NO:20)
CL3N9 (CL3N9 F 5'-AGACACTCAACCGCTGACCT-, (SEQ ID NO:21)
CL3N9 R 5'-GATCTGGAAGTGGAGCCAAC).
```

Linkage disequilibrium analysis was performed on 64 parent-offspring trios in which affected individuals had the clinical features of DM, which include myotonia, muscular dystrophy, cardiac conduction defects, posterior iridescent cataracts, and endocrine disorders (Harper, Myotonic Dystrophy, ed. 2, Saunders, London, (1989).), but not the DM1 mutation. Transmission disequilibrium testing (TDT) (Spielman et al., *Am. J. Hum. Genet.*, 52, 506 (1993)), which was performed using the GENEHUNTER program (version 1.0) (Kruglyak et al., *Am. J. Hum. Genet.*, 58, 1347 (1996)), and analysis of conserved ancestral haplotypes narrowed the DM2 locus to ~320 kilobases (kb) (FIG. 1A). Genbank accession numbers for the three BACs spanning the region of linkage disequilibrium were as follows: RP11-814L21 (AC022944); RP11-723o4 (AC022993); and RP11-221e20 (AC023598).

Expanded CL3N58 Allele Found in DM2 Patients

Figure 1:
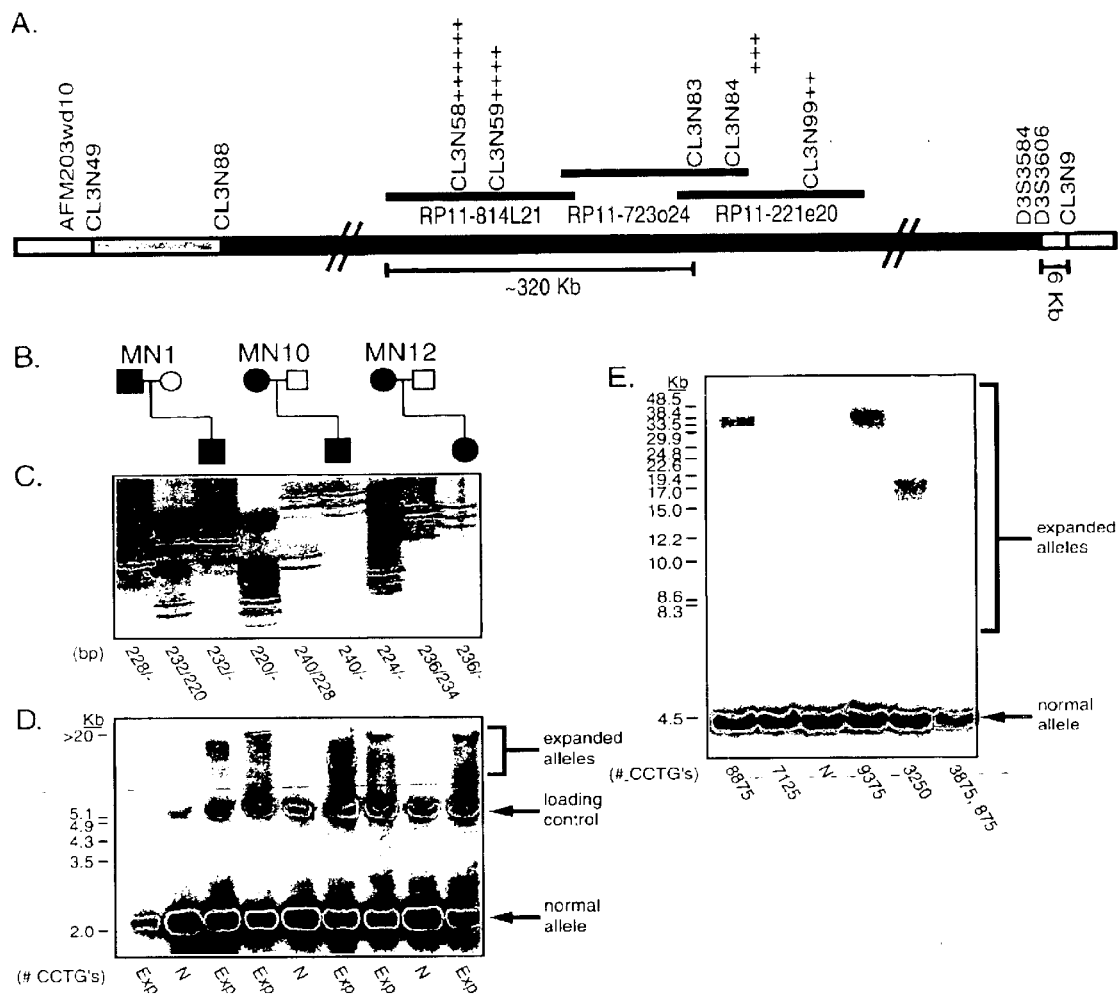
FIG. 1. Expanded CL3N58 allele found in DM2 patients. (A) DM2 critical region. Black represents the minimal DM2 critical region, white represents DM2 excluded regions, and grey represents regions in which recombination has occurred. Markers defining recombination events and establishing linkage disequilibrium are shown, along with previously published markers. The relative significance of the p-values are indicated by plusses above the marker names, with '++'$\leq$0.01, '+++'$\leq$0.001 '++++'$\leq$0.0001, and '++++++'$\leq$0.000001. Three BACs (orientation unknown) within the region of linkage disequilibrium are shown. Not drawn to scale. (B) Pedigrees of three different DM2-linked families, each represented by a nuclear family. (C) PCR analysis of CL3N58 marker. The genotype of each individual is shown, with the size of each allele given in basepairs below each lane. Unamplified alleles are represented by "–". (D) Southern-blot analysis of expansion mutations. Individuals with an expanded CCTG tract are represented by "EXP" and individuals with 2 normal alleles are represented by "N". The blot was also hybridized with an SCA8 loading control, showing that all but the first lane was evenly loaded. (E) High resolution sizing of expansions. Lane 3 contains DNA from a control sample. The number of CCTG's of each individual's expanded allele is shown, with "N" representing a normal length CCTG tract.

One of the markers in linkage disequilibrium with DM2, CL3N58 ($p \leq 0.000001$), showed an aberrant segregation pattern. All affected individuals appeared to be homozygous by PCR, and affected children appeared not to inherit an allele from their affected parent (FIGS. 1, B and C). The PCR to amplify the DM2 repeat region from genomic DNA used primers CL3N58-D F (5'-GCCTAGGGGACAAAGTGAGA (SEQ ID NO:10)) and CL3N58-D R (5'-GGCCTTATAACCATGCAAATG (SEQ ID NO:11)) in a PCR reaction containing 200 $\mu$M dNTPs, 10 mM tris-HCl (pH 9.0), 50 mM KCl, 0.1% Triton X-100, 0.01% (w/v) gelatin, 1 mM $MgCl_2$, 0.4 $\mu$M each primer, and 0.1 U Taq. The reaction was cycled 30 times, where each cycle was 94° C. for 45 seconds, 57° C. for 45 seconds, and 72° C. for 1 minute.

Southern analysis was performed to investigate the possibility that the aberrant segregation pattern was caused by a repeat expansion or other rearrangement. BsoBI-digested genomic DNA (5 $\mu$g) was separated on an 0.8% agarose gel run for 4 hours at 110V, transferred to Hybond N+ membrane (Amersham, Piscataway, N.J.), and hybridized with a 485 base pair ZNF9 probe generated by PCR using the primers probeA F (5'-GAGAACCTTGCCATTTTTCG (SEQ ID NO:22) and probeA R (5'-CACCTACAGCACTGGCAACA (SEQ ID NO:23)) and random-prime-labeled (GibcoBRL, Carlsbad, Calif.) with $^{32}$P-$\alpha$-deoxyadensoine triphosphate (NEN, Boston, Mass.). To avoid partial digestions with BsoBI, we used 120 U of enzyme in a digestion volume of 120 $\mu$l. Membranes were prehybridized using RAPID-HYB buffer (Amersham, Piscataway, N.J.) at 60° for 1 hour. Hybridization was done using at least $4 \times 10^7$ counts per minute (cpm) total of the labeled probe, and incubation was overnight at 60°. The wash conditions were as follows: 2 washes for 5 minutes each at room temperature in a solution containing 2× SSC (one liter of 20× SSC contains 175.3 grams NaCl and 88.2 grams sodium citrate, pH 7.0) and 0.05% sodium dodecyl sulfate (SDS), followed by 2 to 3 washes for 30 minutes each at 52° in a solution containing 0.15× SSC and 0.1% SDS.

In addition to the expected normal allele, a variably sized expanded allele, too large to amplify by PCR, was detected by the Southern analysis and was found only in affected individuals (FIGS. 1, B and D). Modified electrophoresis conditions enabled us to resolve a range of expansions between 10 and 48 kb (FIG. 1E). For more accurate sizing of the high molecular weight expansions, EcoRI-digested genomic DNA (5 μg) was separated on a 0.4% agarose gel run 24 hours at 35 V along with high molecular weight DNA markers (GibcoBRL). BsoBI digests were more useful as a screening tool to identify individuals with DM2 expansions, as the bands were stronger and more discrete. EcoRI digests worked better for accurate sizing of large alleles, but the bands were often present as smears and were sometimes less distinct. The wash conditions were as follows: 2 washes for 5 minutes each at room temperature in a solution containing 2× SSC and 0.05% SDS, followed by 1 wash for 15 minutes at 50° in a solution containing 0.15× SSC and 0.1% SDS, followed by 1 wash for 10 minutes at 50° C. in a solution containing 0.15× SSC and 0.1% SDS.

To determine if this expansion was involved in the DM2 disease process, PCR and Southern analysis were performed on: (i) 51 affected individuals in six families whose disease was consistent with linkage to the DM2 locus; (ii) one affected individual from each of 20 additional families with ancestrally conserved DM2 haplotypes; and (iii) a panel of control genomic samples representing 1360 chromosomes. By PCR all 51 affected individuals in the six DM2 families appeared to be homozygous, with only one band detectable by PCR, but had and expanded allele on subsequent Southern analysis. The maximum lod scores at Θ=0.00 between the disease locus and the CL3N58 expansion for the six families were: MN1=6.9, MN6=1.5, MN10=8.2, MN12=2.8, F134=10.4, and F047=1.8. The maximum LOD scores for these families provide strong evidence that the disease and the expansion mutation are linked, and thus that the expansion mutation is responsible for DM2. Expanded alleles detected by Southern analysis were also found in affected representatives of all 20 additional families with ancestrally conserved DM2 haplotypes. PCR and Southern analysis identified no control samples with an expansion. Unrelated control DNA samples included the grandparents from the panel of 40 Centre d'Etude du Polymorphisme Humain (CEPH) families, spouses of patients diagnosed with muscular dystrophy or ataxia, and ataxia patients (n=1360 chromosomes).

Analysis of DM2-Affected and Normal Alleles

Figure 2:
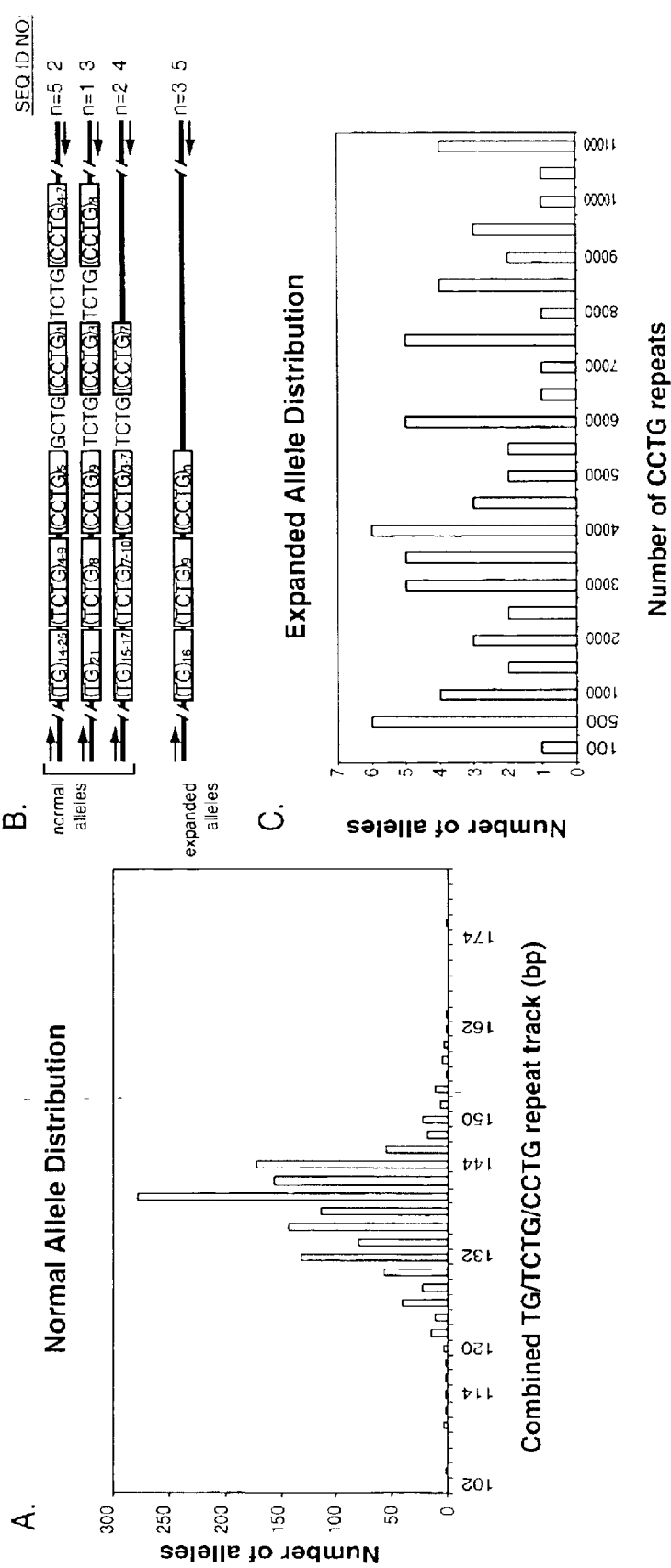
FIG. 2. Analysis of DM2 affected and normal alleles. (A) Distribution of CL3N58 alleles among controls (n=1360). Alleles represent the total basepair size of the combined TG, TCTG, and CCTG repeat tracts. (B) Schematic diagram of DM2 expansion region, showing sequence configurations of normal and expanded repeat tracts. (C) Distribution of expanded alleles among 51 affected members of six DM2 families. All expanded allele sizes were included for individuals with multiple bands and, in contrast to (B), are given in CCTG repeat units.

Sequence of the CL3N58 marker contained the complex repeat motif $(TG)_n(TCTG)_n(CCTG)_n$. In our control group, the size of the $(TG)_n(TCTG)_n(CCTG)_n$ repeat tract ranged from 104–176 bp (Heterozygousity=0.89) (FIG. 2A). Eight normal alleles were amplified from genomic DNA as described above, cloned with the TOPO cloning kit (Invitrogen, Carlsbad, Calif.) and sequenced. All of these normal alleles had CCTG repeat tracts that were interrupted by both GCTG and TCTG motifs or by one or two TCTG motifs (FIG. 2B). The repeat tract in the largest normal allele (combined TG/TCTG/CCTG repeats of 176 bp) was sequenced and shown to contain 26 CCTG repeats with two interruptions. Smaller expanded alleles were amplified from genomic DNA using primers CL3N58-B F (5'-TGAGCCGGAATCATACCAGT (SEQ ID NO:24)) and CL3N58-D R in a PCR reaction (200 μM dNTPs, 50 mM Tris-HCl (pH 9.1), 14 mM (NH4)SO4, 2 mM MgCl2, 0.4 μM each primer, 0.1% Tween-20, 10% dimethyl sulfoxide, 0.75 U ProofSprinter enzyme (Hybaid-AGS, Ashford, Middlesex, UK)) cycled 35 times (94° C. for 30 s, 51° C. for 30 s, 72° C. for 1 min). These expansions were also cloned with the TOPO cloning kit and sequenced, demonstrating that the CCTG portion of the repeat tract is expanded. In contrast to alleles from the control samples, the CCTG repeat tracts on expanded alleles were uninterrupted. Expansion sizes for very large alleles were estimated by Southern analysis assuming that, consistent with the sequenced expansions, lengthening of the CCTG repeat tract accounts for the increase in molecular weight. The range of expanded allele sizes is extremely broad, from 75 to ~11,000 CCTG repeats with a mean of ~5000 (FIG. 2C). Shorter expansions were found in individuals with multiple allele sizes in blood.

Instability of the DM2 Expansion

Figure 3:
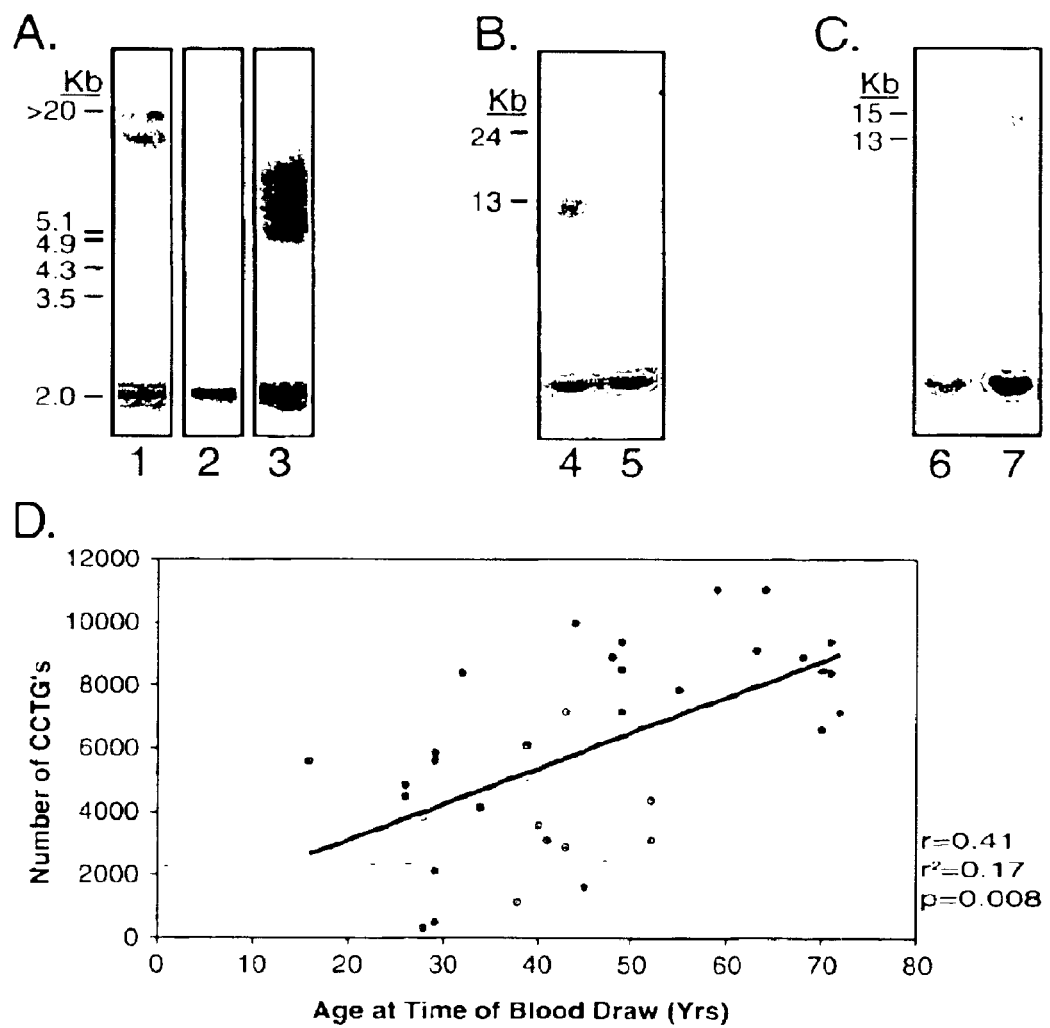
FIG. 3. Instability of the DM2 expansion. (A) Somatic heterogeneity in blood. Southern blots of BsoBI-digested genomic DNA from blood revealed multiple expanded alleles in some affected individuals, some discrete in size (lanes 1 &2), others broad (lane 3). (B) Southern blots of EcoRI-digested genomic DNA from blood of monozygotic twins (lanes 4 and 5). (C) Expanded alleles increase in length over time. Southern blot of EcoRI-digested genomic DNA samples from blood taken from a single patient at 28 (lane 6) and 31 (lane 7) yrs of age, respectively. (D) Correlation between the size of the expanded allele in individuals with a single allele and age at the time blood sample was taken.

In approximately 25% of affected individuals two to four bands were observed in DNA isolated from blood, representing expanded alleles of various sizes (FIG. 3A, Table 1). Some bands were discrete in size, some appeared as unresolved compression bands at the top of the gel, and others showed a broad variation of molecular weight. An additional example of somatic instability included a pair of genetically confirmed (p≦0.0011) monozygotic twins (13 y/o) that had dramatically different expanded alleles (13 kb and 24 kb) (FIG. 3B). Bayesian statistics were used on 6 STR markers from different chromosomes (D3S3684, SCA1 (CAG-a & CAG-b, Orr et al., *Nature Genet.*, 4, 211–226 (1993)), SCA2 (SCA2-A & SCA2-B, Pulst et al., *Nature Genet.* 14, 269–276 (1996)), SCA3 (MJD52 & MJD25, Kawaguchi et al., *Nature Genet.* 8, 221–228 (1994)), SCA6 (S-5-F1 & S-5-R1, Zhuchenko et al., *Nature Genet.*, 15, 62–69 (1997)), SCA8 (SCA8 F3 & SCA8 R2, Koob et al., *Nature Genet.*, 21, 379–84 (1999))), sex, and disease status to confirm that the twins described in FIG. 3B were monozygotic (p>0.001). DNA from both parents and the twins were used to establish haplotypes. Further examples of somatic instability included the observation that the expansion size in lymphocyte DNA from an affected individual increased in size by approximately 2 kb during the 3-year interval between blood donations (FIG. 3C), and the age of affected individuals at the time they donated a blood sample directly correlated (r=0.41, r²=0.17, p=0.008) with the size of the expansion (FIG. 3D). Expansion sizes in the blood of affected children are usually shorter than in their parents: the time-dependent somatic variation of repeat size complicates the interpretation of this difference (Table 1). No significant correlation between age of onset and expansion size was observed.

TABLE 1

Parent-offspring transmissions of the expanded allele in blood. Allele sizes are given in Kb. Multiple expansion sizes indicative of somatic instability are found in some individuals.

| Male Transmissions | | Female Transmissions | |
|---|---|---|---|
| Parental Alleles | Offspring Alleles | Parental Alleles | Offspring Alleles |
| 27, 20, 16 | 9 | 40 | 24 |
| 36 | 20 | 40 | 13 |
| 36 | 23 | 49 | 19 |
| 49 | 27 | 19 | 10, 6 |
| 29 | 27, 20, 6 | 40 | 11 |
| 48, 25 | 20, 5 | 40 | 16 |
| 17, 5 | 18, 9 | 42 | 20, 8 |
| 48, 25 | 38 | 20, 8 | 7 |
| 33, 12 | 49, 17, 12 | 38 | 33 |

Assembly of the ZNF9 Genomic Sequence

The DM2 expansion (CL3N58) was located in a region of the genome for which the available sequence was not completely ordered. To determine the location of the DM2 expansion, portions of the BAC RP11-814L21 were sequenced to assemble unfinished sequence contigs. Unordered sequence contigs from BAC RP11-814L21 (AC022944) were connected by sequencing from the ends of the known sequence contigs using the following primers: 77 3' (5'-CCTGACCTTGTGATCCGACT (SEQ ID NO:25)), 66 3' (5'-TGCTTTATTATAGATTGGAATCCTCA (SEQ ID NO:26)), 66B 3' (5'-AAGACACCTGTCCCCCTAGAA (SEQ ID NO:27)), 39-5' (5'-GGGTGACAGAGCAAGACTCC (SEQ ID NO:28)), 52 3' (5'-TTTTAAACAATGCTACTTAGAATTTCA (SEQ ID NO:29)), 52 5' (5'-GCCGAATTCTTTGTTTTTGC (SEQ ID NO:30)), 59 5' (5'-TTGCTGCAGTTGATGGCTAC (SEQ ID NO:31)), 59B 3' (5'-TGAATTTACTAAGGCCCTTCCA (SEQ ID NO:32)), and 59C 3' (5'-GTGCTCACCTCTCCAAGCTC (SEQ ID NO:33)). These connections were also verified by overlap with sequence from Celera (x2HTBKUAD8C) (Venter et al., Science 291, 1304–51 (2001)).

Our sequencing data and sequence from the Human Genome Project (McPherson et al., Nature 409, 934 (2001)) indicate that the expansion is located in intron 1 of the zinc finger protein 9 (ZNF9) gene (FIG. 4A), also referred to as the cellular nucleic acid-binding protein gene. GenBank accession numbers are as follows: genomic sequence of the DM2 region (AF389886, AF389887); CL3N58 sequence (AF388525); expanded CL3N58 sequence (AF388526); ZNF9 mRNA (M28372); original ZNF9 genomic sequence (U19765). The Celera accession number for the contig overlapping ZNF9 is x2HTBKUAD8C.

ZNF9 contains seven zinc finger domains and is thought to be an RNA-binding protein (Rajavashisth et al., Science 245, 640 (1989), Pellizzoni et al., J. Mol. Biol., 267, 264 (1997)). Although the originally reported genomic sequence for ZNF9 (Pellizzoni et al., J. Mol. Biol., 281, 593 (1998)) did not contain the CL3N58 marker, we have generated additional sequence, used sequence from Celera (Flink et al., Gene 163, 279 (1995)), and performed Southern and RT-PCR analysis to confirm the location of the expansion. To confirm the genomic organization of the ZNF9 gene, NsiI-digested genomic DNA (5 µg) was hybridized with an exon 5 probe generated by PCR using the primers ZNF9-E5 F (5'-GTAGCCATCAACTGCAGCAA (SEQ ID NO:34)) and ZNF9-E5 R (5'-TAATACGACTCACTATAGGGAG-GACGGGCTTACTGGTCTGACTC (SEQ ID NO:35), T7 RNA polymerase promotor sequence is in italics).

Figure 5:
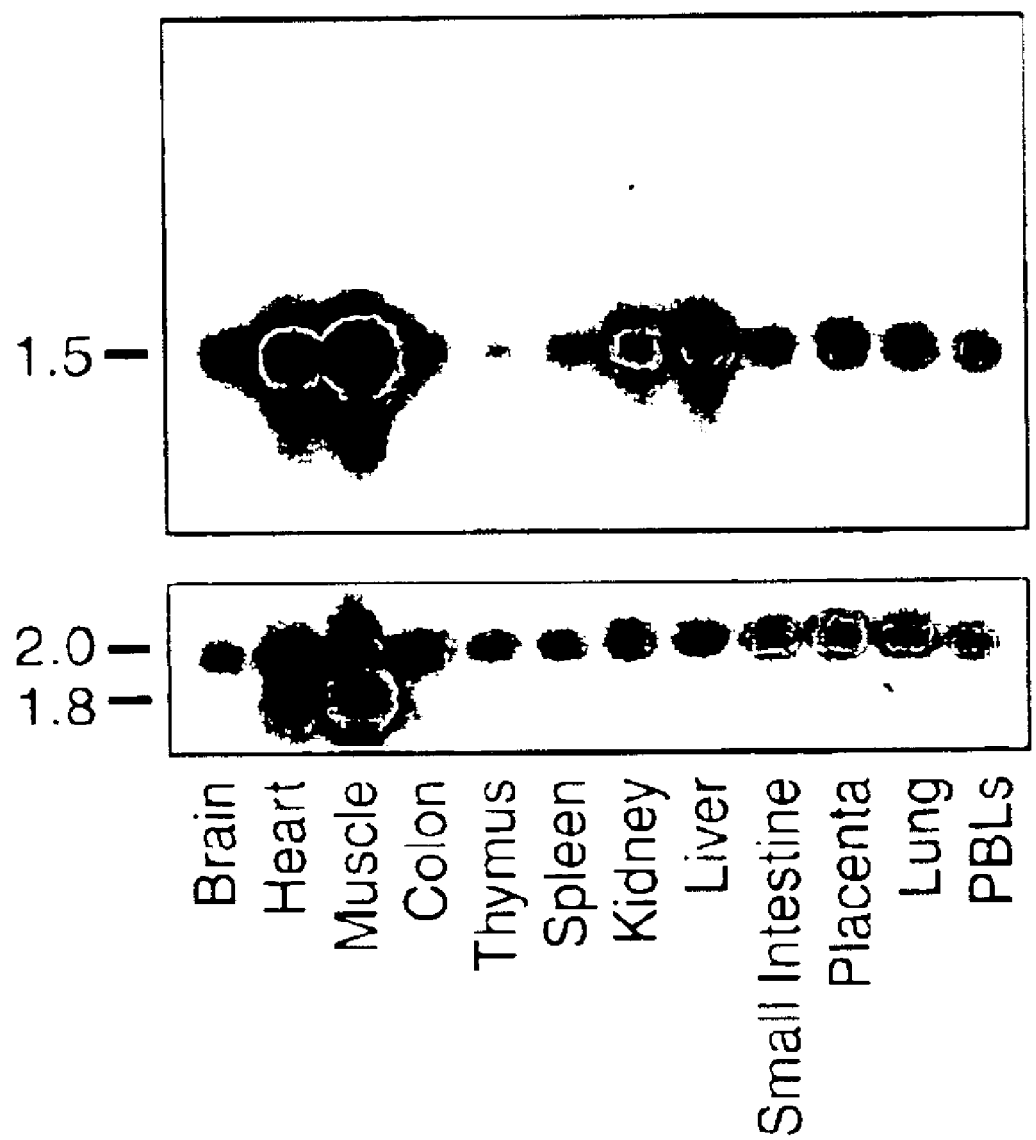
FIG. 5. Northern analysis of ZNF9 RNA expression. Upper panel, human multiple-tissue northern blot hybridized a riboprobe that included exon 5 of ZNF9; lower panel, actin used as a loading control; 1.5, 2.0, 1.8, size in kilobases.

The expression of ZNF9 RNA was evaluated in different tissues by Northern analysis. A human multiple-tissue Northern blot (Clontech, Palo Alto, Calif.) containing tissues from brain, heart, muscle, colon, thymus, spleen, kidney, liver, small intestine, placenta, lung, and peripheral blood lymphocytes (PBLs) was hybridized at 68° C. in UltraHyb hybridization buffer (Ambion, Austin, Tex.) with a 423 bp riboprobe that included exon 5 of ZNF9 (FIG. 5, upper panel). The PCR product was generated from genomic DNA with the primers ZNF9-E5 F and ZNF9-E5 R as described above and used for in vitro transcription using the Maxiscript kit (Ambion) and incorporating $^{32}$P-(alpha)-deoxycytosine triphosphate (ICN, Costa Mesa, Calif.) into the riboprobe. ZNF9 transcripts were found to be broadly expressed, and most abundant in heart and skeletal muscle, two tissues prominently affected in DM2.

In situ hybridization has been used to detect nuclear foci containing the CUG expansion in DM1 cells (Taneja et al., J. Cell Biol., 128, 995 (1995)). Because DM2 is also caused by an expansion motif, we performed fluorescent in situ hybridization to determine if similar repeat-containing nuclear foci are found in DM2. Briefly, for in situ hybridization of muscle sections (Reddy et al., Nature Genet., 13, 325 (1996)), we used 0.2 ng/µl 2'-O-methyl RNA oligonucleotides 5' labeled with Cy3 (IDT, Coralville, Iowa). The $(CAGG)_n$, $(CCUG)_n$, and $(CAG)_n$ oligonucleotides were all 20 bases in length. Fluorescence was visualized using a Zeiss Axioplan2 microscope equipped with a Spot CCD camera (Diagnostic Instruments, Sterling Heights, Mich.). Appropriate exposure times were computed using the DM2/CAGG slide, and the other probes were photographed using this exposure setting.

Fluorescently labeled antisense oligonucleotide probes to the CCUG repeat were hybridized to control, DM2, and DM1 muscle biopsy tissue. The DM2 muscle biopsy was from an affected member of the 3q-linked MN1 family (LOD=6.9), who had a CCTG expansion detected by Southern analysis. Similarly, DM1 tissue was taken from a genetically confirmed DM1 patient. Numerous intense CCUG-containing nuclear foci were observed in DM2 but not control muscle. In DM2 muscle, 1–5 foci were seen per nucleus, with no foci detected in the cytoplasm. In general, more foci were seen per nucleus in DM2 than were seen using antisense probes to the CUG expansions in DM1 muscle. The sense CCUG probes showed no nuclear foci, indicating that the probe hybridized to RNA not DNA. Our results show that the CCTG expansion is expressed but we do not yet know if the RNA foci contain the entire unprocessed ZNF9 transcript. The antisense CCUG probe showed no nuclear foci in DM1 muscle. Although the antisense probe to the CUG repeat also hybridized to foci in DM2 muscle, we believe this signal was caused by non-specific cross-hybridization to the extremely large CCUG repeat tract (11,000 repeats).

Discussion

These results demonstrate that DM2 is caused by an untranslated CCTG expansion. DM2 shows remarkable clinical similarity to DM1, although the disease course of DM2 is usually more benign. Clinical and molecular parallels between these diseases indicate that the CUG and CCUG expansions expressed at the RNA level can themselves be pathogenic and cause the multisystemic features common to DM1 and DM2. Given the similarity of the DM1 and DM2 repeat motifs and the fact that the expansions accumulate as RNA foci, RNA-binding proteins that bind to the DM 1 CUG expansion may also bind to the DM2 CCUG expansion causing similar global disruptions in RNA splicing and cellular metabolism (Timchenko et al., Nucleic Acids Res., 24, 4407 (1996), Lu et al., Hum. Mol. Genet., 8, 53 (1999), Miller et al., EMBO J., 19, 4439 (2000)). One of these proteins has been shown to have a preferential affinity for UG dinucleotides (Takahashi et al., Biochem. Biophys. Res. Commun., 277, 518 (2000)), which are found in both DM1 and DM2 expansions. If these same RNA-binding proteins are involved in DM2 pathogenesis, then one could speculate the longer CCUG repeat tracts cause the milder DM2 phenotype because the affinity of these proteins for the CCUG repeat tract is not as strong. Alternatively, a different set of RNA-binding proteins may bind to the CCUG expansion.

DM2 is the fourth example of a dominant disease that is caused by a microsatellite expansion located in a transcribed but untranslated portion of its respective genes. On the molecular level, the CCTG DM2 expansion has parallels to the untranslated CTG expansions involved in both DM1 (Groenen et al., Bioessays 20, 901 (1998), Tapscott, Science 289, 1701 (2000)) and SCA8 (Koob et al., *Nature Genet.,* 21, 379 (1999)) as well as the ATTCT expansion in SCA10 (Matsuura et al., *Nature Genet.,* 26, 191(2000)). The DM2 tetranucleotide and the SCA10 pentanucleotide expansions are generally longer than the expansions associated with the triplet repeat diseases, with the largest DM2 and SCA10 repeats estimated to be ≧11,000 and 4,500 repeats, respectively.

Repeat instability in DM2 is complicated by the compound repeat motif $(TG)_n(TCTG)_n(CCTG)_n$ and time-dependent somatic instability of the expansion. Although similar somatic instability is seen in DM1 and FMR1 (Wong et al., *Am. J. Hum. Genet.* 56, 114 (1995), Moutou et al., *Hum. Mol. Genet.* 6, 971 (1997), Helderman-van den Enden et al., *J. Med. Genet.* 36, 253 (1999), Lopez de Munain et al., *Ann. Neurol.* 35, 374 (1994)), the size differences for DM2 can be much larger, up to 9000 repeats in the blood of one affected individual. Clinical anticipation has been reported in DM2/PROMM families (Schneider et al., *Neurol.,* 55, 383 (2000)).

Example 2

Repeat Assay

In most cases the expanded alleles are too large to amplify by PCR (FIG. 5A, and Example 1 above). All affected individuals appear to be homozygous by PCR (FIG. 5A, lanes 2 and 3), and affected children often do not appear to inherit an allele from their affected parent. Because some normals can be true homozygotes that can not be distinguished from the DM2 hemizygotes, in some cases CL3N58 PCR is not a definitive test for the DM2 expansion. Southern-blot analysis can used to detect the presence of the expanded allele in affected individuals, as well as confirm the lack of any expansion in any unaffected homozygotes. However, in some cases it can be difficult to visualize the expansion with Southern-blot analysis. Note that there is not the 1:1 correlation in intensity between normal and expanded alleles (FIG. 5B, lanes 1–4), as is seen in other expansion diseases such as SCA8 (FIG. 5B, lane 8). Sometimes the expanded allele(s) can appear so much fainter than the normal allele as to be indistinguishable from background (FIG. 5B, lanes 6 and 7).

To detect the presence of DM2 expansions from individuals for whom Southern blot analysis either appears to be negative or is inconclusive, an additional assay, referred to as the Repeat assay or repeat assay (RA), was developed by modifying a version of PCR developed by Warner et al. (*J. Med. Genet.,* 33, 1022-1-26 (1996)) and Matsuura and Ashizawa (*Ann. Neurol.,* 51, 271–272 (2002)) for the detection of DM1 and SCA10 repeat expansions. This assay can reliably identify the presence or absence of DM2 expansions, although the size of any detected expansion cannot be determined.

The DM2 repeat region (TG/TCTG/CCTG) was amplified from genomic DNA using the primers CL3N58-D R (5'-GGCCTTATAACCATGCAAATG (SEQ ID NO:11), JJP4CAGG (5'-TACGCATCCGAGTTTGAGACGCAGGCAG-GCAGGCAGGCAGG (SEQ ID NO:36)), and JJP3(5'-TACGCATCCGAGTTTGAGACG (SEQ ID NO:37)). CL3N58-D R binds to a unique sequence upstream of the TG/TCTG/CCTG repeat tract. JJP4CAGG consists of the repeat sequence with 5' hanging tail sequence that has negligible complementarity to any known human sequence. The repeat portion of JJP4CAGG will bind randomly at multiple sites within an expanded CCTG tract, giving rise to PCR products of varying sizes, visualized as a smear. JJP3 was complementary to the hanging tail sequence in JJP4CAGG when incorporated into a PCR product, and was used to increase the robustness of the PCR reaction. Optimal amplification was found using PCR reactions of 25 µl volumes with the following buffer components: (200 µM dNTPs, 50 mM Tris pH 9.1, 14 mM $(NH_4)SO_4$, 2 mM $MgCl_2$, 0.4 µM each primer, 0.1% Tween-20, 10% DMSO, 0.75 U ProofSprinter enzyme (Hybaid-AGS)). The PCR conditions consisted of an initial denaturing at 95° C. for 15 minutes, 35 PCR cycles (94° C. for 30 seconds, 51° C. for 30 seconds, 72° C. for 2 minutes), and an additional extension at 72° C. for 10 minutes. Five microliters of 6× loading dye was added to the PCR product and 25 µl were loaded onto an 1% agarose gel with 1 ul of ethidium bromide solution (10 ug/ul) per 100 mls and run for 45 min to 1 hr at 150 V. The gels were transferred to Hybond N+ membrane (Amersham, Piscataway, N.J.) and hybridized with an internal primer CL3N58E-R (5'-TTGGACTTGGAATGAGTGAATG (SEQ ID NO:38)) probe end-labeled with $^{33}P$-γ-dATP using Rapid-Hyb buffer (Amersham, Piscataway, N.J.) according to the manufacturer's instructions. After hybridization the membrane was washed at 45° C. in 2× SSC and 0. 1% SDS and exposed to X-ray film.

Example 3

DM2 in 133 Families: Clinical Features Common to DM1 Demonstrate Pathogenic Effects of CUG/ CCUG RNA Expansions are Multisystemic Methods Family Identification and Clinical Studies Subjects with the clinical diagnosis of DM2 or PROMM, and without a DM1 expansion were enrolled in the research, as were all available family members at risk for the disorder, and spouses with an affected or at risk child. Findings are reported for subjects with CCTG DM2 expansions.

Studies were performed over a 10-year period of time, with additional testing included as understanding of the disease evolved. Subjects were interviewed and examined in both clinical and community settings. Electrophysiological assessment was done with portable electromyographic equipment, including Nicollet and Dantec/Medtronik electromyographic equipment. Ophthalmologic examinations in the field were performed with direct ophthalmoscopy; some individuals additionally underwent slit lamp examinations in ophthalmology clinics. Muscle biopsies were quick-frozen, sectioned and stained with hematoxylin and eosin for most results reported, identifying fiber types by ATPase staining at different pH values. Clinical results are reported as percentages of individuals tested for each specific feature.

Genetic Methods

CL3N58 PCR amplification across the DM2 CCTG repeat, and Southern analysis, was done as described Example 1. The Repeat assay was performed as described in Example 2.

Results

Patient Population

We have studied 352 subjects genetically diagnosed as having DM2 from 133 German and Minnesota families. Most families could trace an affected ancestor to Germany or Poland and all were of European descent. 332 males and 420 females at risk for the disease participated in the study, of those 147 males and 208 females were positive for the DM2 expansion. The age of the participants ranged from 8 to 85 with a mean age of 47 years.

Clinical Features of DM2 Patients

Muscle Symptoms and Signs. Similar to DM1, myotonia and muscle weakness are the most common symptoms reported in DM2 subjects of all ages (Table 2). Similarly, the characteristic pattern of muscle weakness in DM1 affecting neck flexion, thumb or finger flexion, and elbow extension is also present in DM2. Facial and ankle dorsiflexor weakness, features of DM1, were present to a lesser degree in DM2 subjects. Subjects with DM2 or PROMM frequently developed symptomatic weakness after age 50 years, when they began to complain of difficulty standing up from a squatting position. Although hip-flexion weakness is the reason most DM2/PROMM subjects seek medical attention, in DM1 it often develops after patient have sought medical assistance for other problems. Muscle pain, which is common in DM2, is also common, although less recognized in DM1. Among DM2 patients between 21–34 years of age, only 36% complained of weakness, but on examination weakness was demonstrable in 59%.

TABLE 2

CLINICAL FEATURES OF DM2 AND DM1

Skeletal Muscle Features

| | | 21–34y (n = 45) | 35–50y (n = 77) | >50y (n = 100) | DM1 |
|---|---|---|---|---|---|
| History of Muscle Pain | | 43% | 61% | 63% | +/++ |
| Myotonia | By History | 39 | 39 | 34 | +++ |
| | On Physical Exam | 80 | 84 | 71 | +++ |
| | On EMG (210) | 87 | 94 | 92 | +++ |
| Weakness | By History | 36 | 69 | 84 | +++ |
| | Any Weakness on Exam | 59 | 85 | 99 | |
| | Facial | 18 | 9 | 13 | ++ |
| | Neck Flexion | 47 | 75 | 95 | +++ |
| | Elbow Extension | 8 | 16 | 52 | ++ |
| | Thumb/Finger Flex | 39 | 63 | 49 | +++ |
| | Hip Flexion | 36 | 58 | 88 | + |
| | Ankle Dorsiflexion | 9 | 14 | 19 | ++ |
| | Deep Knee Bend | 26 | 48 | 77 | + |
| High CK | | 88 | 91 | 93 | ++ |

Multisystemic Features

| | | | | | |
|---|---|---|---|---|---|
| Cardiac | Arrhythmia/Palp | 7% | 27% | 27% | + |
| | Cardiomyopathy | 0 | 0 | 7 | +/– |
| Cataracts | By history or exam | 36 | 59 | 78 | ++ |
| | Hx Extraction | 13 | 18 | 55 | |
| Diabetes | By history | 4 | 17 | 36 | + |

Additional Laboratory Findings

| | | DM2 Mean Age (Age Range) | % Affected | DM1 |
|---|---|---|---|---|
| Serology | High GGT (152) | 46y (13–78y) | 64% | + |
| | Low IgG (20) | 46 (28–64) | 65 | ++ |
| | Low IgM (20) | 46 (28–64) | 11 | + |
| | Low Testosterone (22) | 45 (27–64) | 29 | ++ |
| | High FSH (26) | 42 (16–64) | 65 | ++ |
| | Insulin Insensitivity (16) | 47 (28–75) | 75 | ++ |
| EKG | AV Block (44) | 47 (16–73) | 11 | ++ |
| | IV Block (44) | 47 (16–73) | 11 | + |
| Muscle Biopsy | Internal nuclei (42) | 50 (16–64) | 95 | ++ |
| | Nuclear Bag fibers (36) | 50 (16–64) | 89 | ++ |
| | Abnl fiber typing (31) | 50 (16–64) | 16 | +/– |
| | Necrotic fibers (38) | 50 (16–64) | 47 | + |
| | Fibrosis (38) | 50 (16–64) | 71 | + |

DM1 features are reported as being almost universally present (+++), common and almost universally present late in the course of the disease (++), well recognized and common late in the course of the disease (+), and recognized but not common (+/–).

Muscle Biopsies. Muscle biopsies from 42 DM2 patients were indistinguishable from DM1 biopsies on routine studies, with a high percentage of fibers having centrally located nuclei that sometimes occur in chains, angulated atrophic fibers sometimes occurring in groups, severely atrophic ("nuclear bag") fibers, hypertrophic fibers, occasional necrotic fibers, fibrosis and adipose deposition. There was no consistent abnormality of fiber type distribution, with 2 biopsies having mild type 1 predominance and 2 having mild type 2 predominance. Atrophic angulated fibers of both fiber types, as determined by ATPase staining, were evident in most biopsies.

Cataracts. The posterior subcapsular iridescent cataracts are identical in DM1 and DM2 patients. Cataracts needed to be extracted in 75 individuals at ages ranging from 28–74 years. Among 10 genetically positive subjects under 21 years, cataracts were present in two, indicating that this is a prominent and early feature of the disease. In DM1, cataracts evident by ophthalmoscopy typically develop in the $3^{rd}$-$5^{th}$ decades of life, with small percentages occurring in the $2^{nd}$ decade of life.

Cardiac Features. In DM2 patients, cardiac complaints include frequent palpitations, intermittent tachycardia and episodic syncope. These symptoms, which are present in both DM1 and DM2, increase in frequency with age (Table 2). Cardiac conduction abnormalities, either atrioventricular or intraventricular blocks, were seen in 20% (9/44) of DM2 patients. Conduction abnormalities are more frequent in DM1, but patients with either disease can develop unexpected fatal arrhythmias. Cardiomyopathy, a debilitating and life-threatening condition found in 7% of DM2 patients over 50 years, is rarely reported in DM1.

Systemic Changes. A striking feature of myotonic dystrophy is the idiosyncratic involvement of nearly all organ systems. Many of the features that include the broad clinical presentation of DM 1 are mirrored in DM2. Laboratory results from 150 patients showed elevated serum CK (typically less than 5× the upper limits of normal) and GGT. Additional serological testing on 20 patients showed low IgG and IgM, but normal IgA. As in DM1, evidence of primary male hypogonadism was present in the majority of males, with elevated FSH, low or low-normal testosterone levels, and several men having documented oligospermia. Blood glucose levels showed diabetes in 23% (n=79). Formal glucose tolerance testing showed insulin insensitivity (elevated basal insulin levels or prolonged insulin elevation, n=16). Age-independent hyperhydrosis reported by 20–30% of DM2 patients is also present in DM1, and early-onset male frontal balding is common in both disorders.

Age of onset. Initial DM2 symptoms were reported to have occurred from ages 8–67, with a mean age of onset of 48 y. Individuals less than 21 years of age were not routinely enrolled in the study, but analysis of reports from 12 such genetically affected individuals showed reports of muscle pain, myotonia, and hyperhydrosis, but not weakness, cardiac symptoms, diabetes or visual impairment from cataracts. A severe congenital form of DM2 has not been observed.

Genetic and Molecular Features

Figure 6:
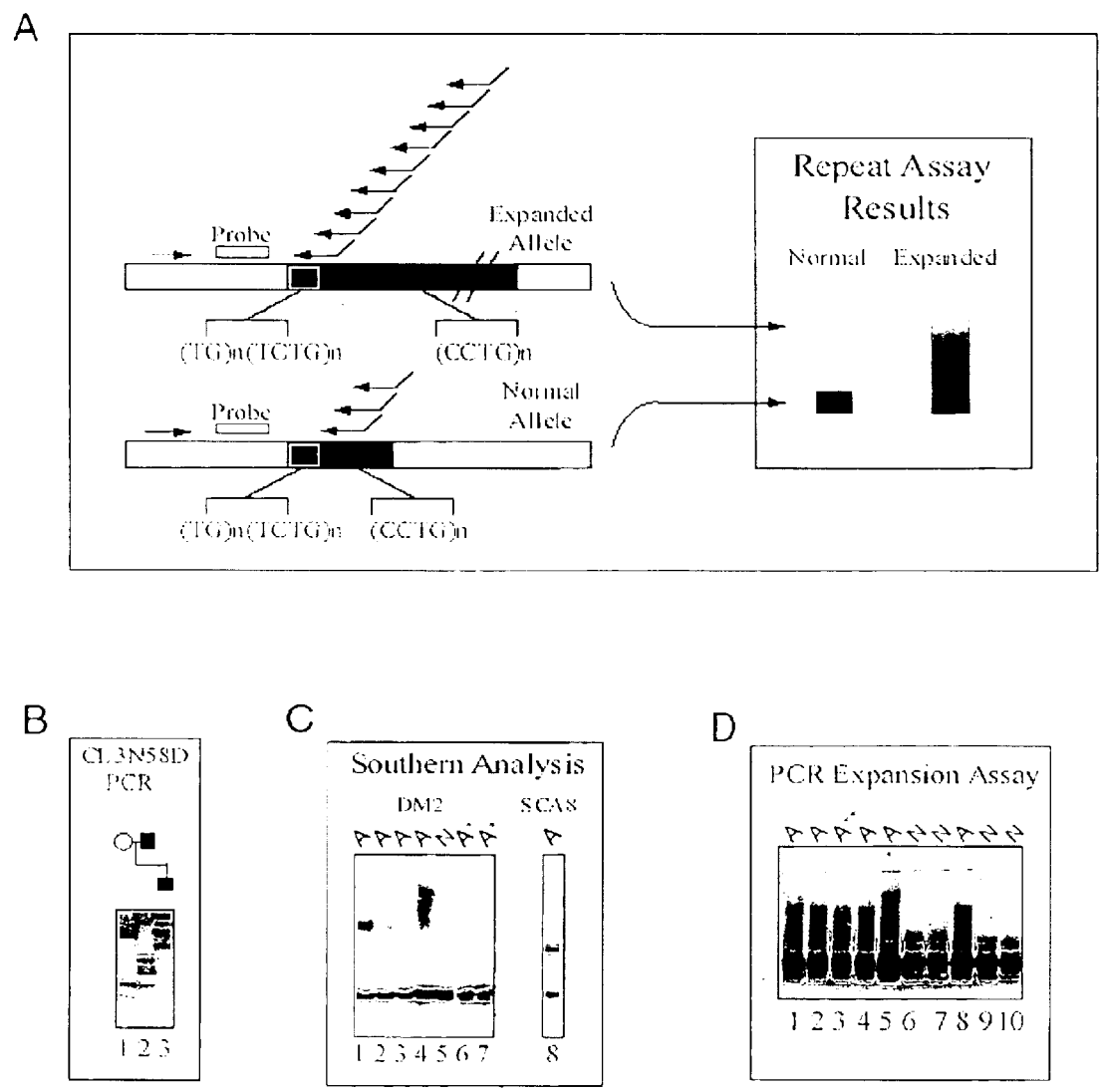
FIG. 6. (A) Schematic diagram of repeat assay PCR reaction products. (B) PCR analysis of CL3N58 marker. Lane 1, from the unaffected mother, shows two alleles. Lanes 2 and 3, from the affected father and affected son, respectively, show only one allele. There is no shared allele in lanes 2 and 3, as would be expected in normal Mendelian inheritance of PCR alleles. (C) Southern-blot analysis of expansion mutations. Lanes 1–4 show affected individuals with detectable expanded bands. Lane 5 shows an unaffected individual with only the normal-sized band. Lanes 6 and 7 show affected individuals with no detec" expansion. Lane 8 shows an affected SCA8 individual with an expanded band. (D) Repeat assay of DM2 mutations. Lanes 1–5 and 8 show affected individuals who are expansion-positive, indicated by smears above the normal allele, by the Repeat assay. Lanes 1, 2, 4, 5, and 8 show affected individuals who had expansions by Southern-blot analysis, while lane 3 shows an affected individual who had no detectable expansion by Southern-blot analysis. Lanes 6, 7, 9, and 10 show unaffected individuals who are expansion-negative, indicated by the lack of smears above the normal allele, by the Repeat assay. (E) Abbreviated pedigree of a DM2 family. Filled-in symbols represent affected individuals. Below each symbol: age of blood draw, CL3N58 PCR allele sizes (where "B" signifies evident existence of a non-amplifying blank allele), and either the size of the expansion detected by Southern ("N kb") or the result of the Repeat assay, given as Exp(+) or Exp(−), where Exp refers to expansion, for those with no expansion on southern analysis.
Figure 6:
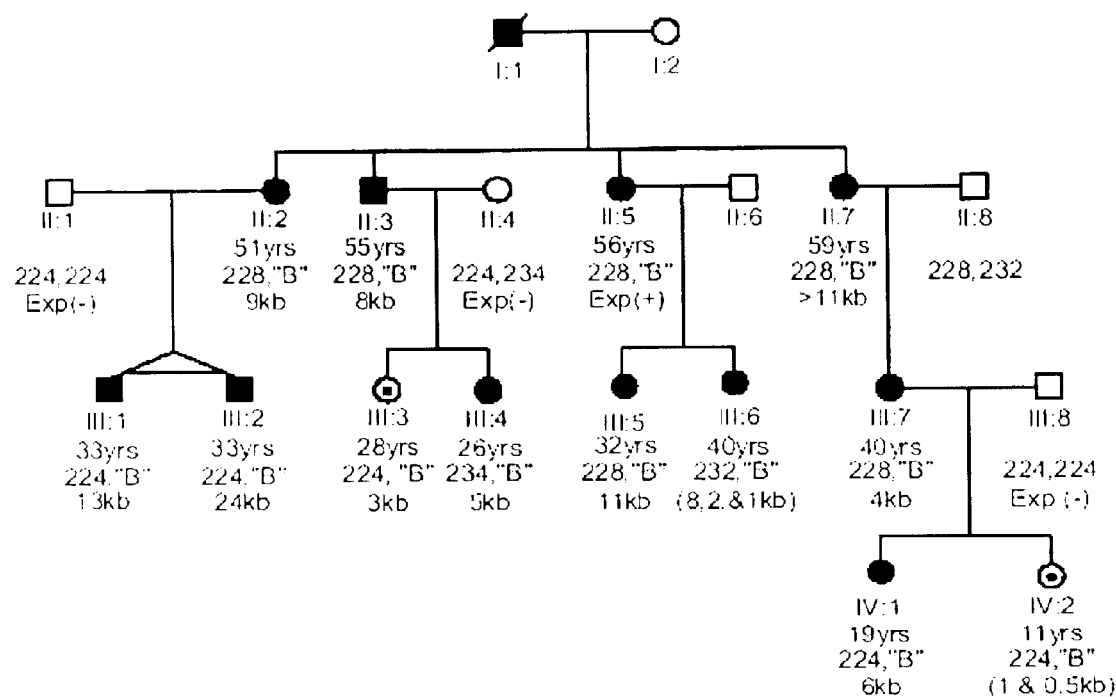

Diagnostic Methods and Instability. The unprecedented size and somatic instability of the DM2 expansion complicate molecular testing and interpretation of genetic test results (FIG. 6). The DM2 locus contains a complex repeat motif $(TG)_n(TCTG)_n (CCTG)_n$, with the CCTG portion expanding on affected alleles. The expanded alleles are too large to amplify by PCR, causing all affected individuals to appear homozygous (FIG. 6B, lanes 2 and 3) and thus indistinguishable from the 15% of unaffected controls who are truly homozygous. Family studies can distinguish true homozygotes from expansion carriers, (FIG. 6B lanes 1–3), because affected children often do not appear to inherit an allele from their affected parent. We refer to this apparent non-Mendellian inheritance pattern, which is caused by the failure of the expanded allele to amplify, as the presence of a "blank allele." Demonstration of a blank allele provides strong evidence that a family carries a DM2 expansion, but can also occur due to non-paternity.

In other expansion disorders, Southern analysis (FIG. 6C) can reliably confirm the presence of expansions too large to amplify by PCR. Because of the unprecedented size (>11,000 CCTG repeats) and somatic instability of the DM2 repeat, genomic Southerns fail to detect 26% of expansions in known carriers. Expanded alleles when detected can appear as single discrete bands, multiple bands, or smears (FIG. 6B). Compared to other expansion disorders, such as SCA8 (FIG. 6D, lane 8), in which the expanded and normal alleles are equally intense, detectable DM2 expansions are almost always less intense than the normal alleles. This intensity difference indicates that even when a proportion of the expanded alleles create a discrete visible band, the rest of the expanded alleles vary markedly in size resulting in a diffuse undetectable smear.

To detect the presence of DM2 expansions in individuals with inconclusive Southern blots, the repeat assay (RA) described in Example 2 was used. By using a PCR primer that hybridizes and primes from multiple sites within the elongated CCTG repeat tract, this assay reliably identified the presence or absence of DM2 expansions. To insure specificity, the PCR products were transferred to a nylon membrane and probed with an internal oligonucleotide probe. When the probe was used there were no false positives in 320 control chromosomes. In contrast there was a 5% false positive rate when the PCR products were visualized directly without use of an internal probe. As detailed in Table 3, the DM2 repeat assay is a sensitive and specific method to identify DM2 expansions, increasing the detection rate from 74% by genomic Southern analysis alone to 99% using both methods. Among all of the samples tested, 352 individuals have been identified from 133 families who were genetically confirmed by Southern and/or RA analyses.

TABLE 3

| Confirmed DM2 Cases* | Expansion Detected by Southern | Expansion Detected by Repeat Assay | Expansion Detected by either Southern or Repeat Assay |
|---|---|---|---|
| 174 | 128 | 166 | 172 |
|  | 74% | 95% | 99% |

*Individuals independently confirmed to have DM2 expansions by presence of "blank allele" or linkage analysis.

The correlation of the repeat size with various measures of disease onset for individuals with single bands on Southern analysis is shown in FIG. 8. For repeat size versus age at onset of initial symptom (n=91) there was a positive correlation r=0.28 (p=4.2×10⁻³, $r^2$=0.08). For repeat size versus age at onset of weakness (n=59) a positive correlation coefficient of r=0.53 was obtained (p=8.7×10⁻⁶, $r^2$=0.28). No significant correlation was observed between repeat size and age of cataract extraction (n=29). The positive correlations between repeat length and age of onset, as well as repeat length and onset of weakness, were surprising because in all other microsatellite expansion disorders larger expansions are associated with earlier ages of onset. To determine if these positive correlations could be explained by the increase in CCTG repeat tracts with age, multivariate analysis was performed and indicated that the effect of age on repeat length explained more than 98% of the apparent of effect of repeat length on onset of symptoms.

Although complicated by somatic instability and increases in repeat length with age, we compared repeat lengths of 19 affected parent-child pairs from a subset of individuals in which both the parent and child had single bands on Southern analysis (FIG. 9A). Surprisingly, we observed apparent reductions of repeat length in 16 of 19 transmissions, with a mean change of −13 Kb (−3250 CCTG repeats). In one instance the repeat size was 38 Kb smaller in the affected child (−9500 CCTG repeats). There were apparent size increases in 2 transmissions (+8 and +13 Kb). No differences in degree or direction of intergenerational changes were seen in male vs. female transmissions. These apparent intergenerational changes in repeat length are much greater for DM2 than for any other microsatellite disorder (FIG. 9B).

Pedigree Examples of Instability

The pedigree shown in FIG. 6E illustrates the diagnostic challenges and types of repeat instability that are typical in a DM2 family. Intergenerational repeat sizes can vary dramatically. For example individual III-7 has a smaller expansion than her affected parent, which is larger in one of her children and smaller in the other. Somatic instability is strikingly illustrated by monozygotic twins III-1 and III-2, with expansion sizes that differ in size by 11 kb (2750 CCTGs). Some family members have single discrete expansions, multiple expansions and diffuse bands. An example of the utility of the repeat assay is demonstrated by individual II-5, who was RA positive but negative by Southern analysis.

Discussion

Clinical Features

This study details the broad idiosyncratic features common to DM1 and DM2, demonstrating the multisystemic effects of CUG and CCUG RNA expansions in disease pathogenesis. DM2 closely resembles adult-onset DM1, with a long list of common features including progressive weakness, myotonia, disease specific muscle histology, cardiac arrhythmias, iridescent cataracts, male hypogonadism, early-onset balding, insulin insensitivity, and hypogammaglobulinemia. The presence of these seemingly unrelated features in both DM1 and DM2 indicates that a common pathogenic mechanism is likely responsible for both disorders.

Despite the striking similarities of DM2 and adult-onset DM1, there are differences. One clear distinction is the lack of a congenital form of DM2. Other differences of DM2 include an apparent lack of mental retardation, and less evident central hypersomnia, severe distal weakness, and marked muscle atrophy. DM 1 individuals often come to medical attention because of the mental retardation or disabling distal weakness and myotonia, but DM2 patients typically first seek medical evaluation when they develop proximal lower extremity weakness. Although many DM2 features are milder than in DM1 (clinical myotonia, distal and facial weakness), some appear to be equally significant (cataracts, hypogonadism, and insulin insensitivity), and others may be more severe in DM2 (cardiomyopathy). It remains to be determined whether the generally milder phenotype of DM2, despite the presence of a much larger genetic repeat expansion, indicates that the pathophysiological effects of CCTG expansions are simply less severe than CTG expansions, or whether secondary processes augment the pathophysiological mechanisms in DM1.

We have identified 389 DM2-positive individuals from 133 families. Our ability to identify a large number of DM2 families in both Minnesota and Germany indicates that initial estimates that 98% of DM families have the DM1 expansion are too high, at least in Northern European populations. DM1 families often come to medical attention when a child is severely affected. In contrast the lack of congenital DM2 may explain its apparent underdiagnosis. DM2 patients often seek medical attention for isolated disease features, without being aware of their complex underlying disease. A genetic diagnosis of DM2 will improve patient care by facilitating better monitoring of the diverse clinical features known to be part of the disease, including early onset cataracts, diabetes, testicular failure and cardiac arrhythmias.

Genetics

Unique genetic features of the DM2 expansion include the following: i) it is the first pathogenic tetranucleotide expansion; ii) expansions are larger than reported in any other disease (more than 44 Kb in DM2 versus 12 Kb in DM1); iii) there is an unprecedented degree of somatic instability. The somatic instability is so dramatic that ~¼ of the expansions are not detectable by Southern analysis, which results in a diagnostic challenge not previously reported, even among disorders with large expansions such as DM1, SCA8, and SCA10. Although the somatic instability complicates the molecular diagnosis of DM2, combining it with the RA improves detection to >99%.

In other reported microsatellite expansion disorders larger repeat tracts are associated with earlier onset and increased disease severity. Although anticipation has been reported in DM2/PROMM families based on clinical criteria, the expected trend of longer repeats being associated with earlier ages of onset was not observed. The somatic heterogeneity, and the fact that the size of the repeat dramatically increases in size with age, complicate this analysis and may mask meaningful biological effects of repeat size on disease onset. It is also possible that expansions over the pathogenic size threshold exert similar effects regardless of how large they become, or even that smaller repeats are more pathogenic than larger repeats. In adult-onset DM1, the tightest correlations between repeat length and disease onset are for repeats less than 150 CTGs, which may indicate that correlations at larger repeat sizes for DM1 are also difficult to measure either because of increased somatic mosaicism or a ceiling effect in which repeat sizes over a certain length cause similar degrees of pathology. Determination of DM2 somatic mosaicism in tissues other than blood may help clarify the pathogenic effects of the expansion, although somatic mosaicism observed in other tissues (such as skeletal muscle) may continue to obscure length-dependent pathological effects. The intergenerational differences in repeat length in DM2, with surprisingly shorter repeat tracts seen after both maternal and paternal transmission, may also be affected by the marked range of repeat size in each affected individual and the increase in repeat length over time.

The complete disclosure of all patents, patent applications, and publications, and electronically available material (including, for instance, nucleotide sequence submissions in, e.g., GenBank, dbSTS, and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. A method for detecting a polynucleotide comprising a repeat tract within an intron 1 of a zinc finger protein 9 (ZNF9) genomic sequence, the method comprising:
   amplifying nucleotides of an intron 1 region of a ZNF9 genomic sequence to form amplified polynucleotides, wherein the amplified polynucleotides comprise repeat tracts; and detecting the amplified polynucleotides.

2. A method for detecting a polynucleotide comprising a repeat tract within an intron 1 of a ZNF9 genomic sequence, the method comprising:
   digesting genomic DNA with a restriction endonuclease to obtain polynucleotides;
   probing the polynucleotides under hybridizing conditions with a detectably labeled probe which hybridizes to a polynucleotide containing a repeat tract within an intron 1 of a ZNF9 genomic sequence; and
   detecting the probe which has hybridized to the polynucleotides.

3. A method for identifying an individual not at risk for developing myotonic dystrophy type 2 (DM2), the method comprising:
   analyzing intron 1 regions of ZNF9 genomic sequences of an individual for two not at risk alleles comprising repeat tracts of no greater than about 176 nucleotides, wherein an individual comprising two alleles comprising repeat tracts of no greater than about 176 nucleotides is not at risk for developing DM2.

4. A method for identifying an individual not at risk for developing DM2, the method comprising:
   amplifying nucleotides of intron 1 regions of ZNF9 genomic sequences of an individual to form amplified polynucleotides, wherein the amplified polynucleotides comprise repeat tracts;
   comparing the size of the amplified polynucleotides; and
   analyzing the amplified polynucleotides for two not at risk alleles wherein an individual comprising two not at risk alleles is not at risk for developing DM2.

5. The method of claim 4 wherein amplifying comprises:
   performing a polymerase chain reaction (PCR) with a primer pair comprising a first primer and a second primer, wherein the first primer and the second primer flank the repeat tracts located within the intron 1 regions, wherein the first primer comprises at least about 15 nucleotides selected from nucleotides 15701–17701 of SEQ ID NO: 1, and the second primer comprises at least about 15 nucleotides selected from nucleotides 17858–18661 of SEQ ID NO:1.

6. A method for identifying an individual not at risk for developing DM2, the method comprising:
   amplifying nucleotides of intron 1 regions within ZNF9 genomic sequences of an individual to form amplified polynucleotides, wherein the amplified polynucleotides comprise repeat tracts; and
   analyzing the repeat tracts of the amplified polynucleotides for two not at risk alleles comprising repeat tracts of no greater than about 176 nucleotides, wherein an individual comprising two alleles comprising repeat tracts of no greater than about 176 nucleotides is not at risk for developing DM2.

7. A method for identifying an individual that has DM2 or is at risk for developing DM2, the method comprising:
   analyzing an intron 1 region of a ZNF9 genomic sequence of an individual for one at risk allele comprising a repeat tract comprising at least about 75 CCTG repeats wherein an individual comprising one allele comnrising a repeat tract of at least about 75 CCTG repeats has DM2 or is at risk for developing DM2.

8. A method for identifying an individual that has DM2 or is at risk for developing DM2, the method comprising:
   digesting genomic DNA of an individual with a restriction endonuclease to obtain polynucleotides;
   probing the polynucleotides under hybridizing conditions with a detectably labeled probe that hybridizes to a polynucleotide containing a repeat tract within an intron 1 of a ZNF9 genomic sequence;
   detecting the probe that has hybridized to the polynucleotide; and
   analyzing the intron 1 region of the hybridized polynucleotide for one at risk allele comprising a repeat tract comprising at least about 75 CCTG repeats, wherein an individual comprising one allele comprising a repeat tract of at least about 75 CCTG repeats has DM2 or is at risk for developing DM2.

9. The method of claim 8 wherein the probe comprises at least about 200 consecutive nucleotides from SEQ ID NO: 1, or the complement of the at least 200 concecutive nucleotides from SEQ ID NO:1.

10. A method for identifying an individual that has or is at risk for developing DM2, the method comprising:
    amplifying nucleotides of an intron 1 region of a ZNF9 genomic sequence of an individual to form amplified polynucleotides, wherein the amplified polynucleotides comprise a repeat tract; and
    analyzing the repeat tracts of the amplified polynucleotides for one at risk allele comprising a repeat tract comprising at least about 75 CCTG repeats, wherein an individual comprising one at risk allele comnrising a repeat tract of at least about 75 CCTG reoeats has or is at risk for develoDing DM2.

11. The method of claim 10 wherein amplifying comprises:
    performing a PCR with a primer pair comprising a first primer and a second primer, wherein the first primer flanks the CCTG repeat tract located within the intron 1 region, the first primer comprising at least about 15 nucleotides selected from nucleotides 4469 15701–17701 of SEQ ID NQ:1 or nucleotides 17858–18661 of SEQ ID NO:1, and the second primer comprising a nucleotide sequence that hybridizes to the CCTG repeat tract.

12. The method of claim 1 wherein detecting comprises detecting amplified polynucleotides comprising a repeat tract of no greater than about 176 nucleotides.

13. The method of claim 1 wherein detecting comprises detecting amplified polynucleotides comprising a repeat tract comprising at least about 75 CCTG repeats.

14. The method of claim 1 wherein amplifying comprises:
    performing a PCR with a primer pair comprising a first primer and a second primer, wherein the first primer and the second primer flank the repeat tracts located within the intron 1 regions, wherein the first primer comprises at least about 15 nucleotides selected from nucleotides 15701–17701 of SEQ ID NO:1, and the second primer comprises at least about 15 nucleotides selected from nucleotides 17858–19858 of SEQ ID NO: 1.

15. The method of claim 14 wherein the first primer comprises GGCCTTATAACCATGCAAATG (SEQ ID NO:11) and the second primer comprises GCCTAGGGGACAAAGTGAGA (SEQ ID NO:10).

16. The method of claim 1 wherein amplifying comprises:
performing a PCR with a primer pair comprising a first primer and a second primer, wherein the first primer flanks a CCTG repeat tract located within the intron 1 region, the first primer comprising at least about 15 nucleotides selected from nucleotides 15701–17701 of SEQ ID NO:1 or nucleotides 17858–18661 of SEQ ID NO:1, and the second primer comprising a nucleotide sequence that hybridizes to the CCTG repeat tract.

17. The method of claim 1 wherein amplifying comprises:
performing a PCR with a first primer comprising GGC-CTTTATAACCATGCAAATG (SEQ ID NO:11), a second primer comprising TACGCATC-CGAGTTTGAGACGCAGGCAGGCAGGCAGGCAGG (SEQ ID NO:36), and a third primer comprising TACGCATCCGAGTTTGAGACG (SEQ ID NO:37).

18. The method of claim 1 wherein amplifying comprises:
performing a PCR with a primer pair comprising a first primer and a second primer, wherein the first primer flanks a CCTG repeat tract located within the intron 1 region, the first primer comprising at least about 15 nucleotides selected from nucleotides 15701–17701 of SEQ ID NO:1 or nucleotides 17858–19858 of SEQ ID NO:1, and the second primer comprising a nucleotide sequence that hybridizes to the CCTG repeat tract.

19. The method of claim 2 wherein the probe comprises at least about 200 consecutive nucleotides from SEQ ID NO: 1, or the complement of the at least 200 consective nucleotides from SEQ ID NO: 1.

20. The method of claim 2 wherein the probe comprises TTGGACTTGQAATGAGTGAATG (SEQ ID NO:38) or nucleotides 16507–16992 of SEQ ID NO:1.

21. The method of claim 4 wherein amplifying comprises:
performing a PCR with a primer pair comprising a first primer and a second primer, wherein the first primer and the second primer flank the repeat tracts located within the intron 1 regions, wherein the first primer comprises at least about 15 nucleotides selected from nucleotides 15701–17701 of SEQ ID NO:1, and the second primer comprises at least about 15 nucleotides selected from nucleotides 17858–19858 of SEQ ID NO:1.

22. The method of claim 21 wherein the first primer comprises GGCCTTATAACCATGCAAATG (SEQ ID NO: 11) and the second primer comprises GCCTAGGGGA-CAAAGTGAGA (SEQ ID NO:10).

23. The method of claim 6 wherein amplifying comprises:
performing a PCR with a primer pair comprising a first primer and a second primer, wherein the first primer and the second primer flank the repeat tracts located within the intron 1 regions, wherein the first primer comprises at least about 15 nucleotides selected from nucleotides 15701–17701 of SEQ ID NO:1, and the second primer comprises at least about 15 nucleotides selected from nucleotides 17858–19858 of SEQ ID NO:1.

24. The method of claim 23 wherein the first primer comprises GGCCTTATAACCATGCAAATG (SEQ ID NO:11) and the second primer comprises GCCTAGGGGA-CAAAGTGAGA (SEQ ID NO:10).

25. The method of claim 6 wherein amplifying comprises:
performing a polymerase chain reaction (PCR) with a primer pair comprising a first primer and a second primer, wherein the first primer and the second primer flank the repeat tracts located within the intron 1 regions, wherein the first primer comprises at least about 15 nucleotides selected from nucleotides 15701–17701 of SEQ ID NO:1, and the second primer comprises at least about 15 nucleotides selected from nucleotides 17858–18661 of SEQ ID NO: 1.

26. The method of claim 8 wherein the probe comprises TTGGACTTGGAATGAGTGAATG (SEQ ID NO:38) or nucleotides 16507–16992 of SEQ ID NO:1.

27. The method of claim 10 wherein amplifying comprises:
performing a PCR with a primer pair comprising a first primer and a second primer, wherein the first primer flanks the CCTG repeat tract located within the intron 1 region, the first primer comprising at least about 15 nucleotides selected from nucleotides 15701–17701 of SEQ ID NO:1 ornucleotides 17858–19858 of SEQ ID NO:1, and the second primer comprising a nucleotide sequence that hybridizes to the CCTG repeat tract.

28. The method of claim 10 wherein amplifying comprises:
performing a PCR with a first primer comprising GGC-CTTATAACCATGCAAATG (SEQ ID NO:11), a second primer comprises TACGCATC-CGAGTTTGAGACGCAGGCAGGCAGGCAGGCAGG (SEQ ID NO:36), and a third primer comprising TACGCATCCGAGTTTGAGACG (SEQ ID NO:37).

29. A method for identifying an individual not at risk for developing DM2, the method comprising:
amplifying nucleotides of intron 1 regions of ZNF9 genomic sequences of an individual to form amplified polynucleotides, wherein the amplified polynucleotides comprise repeat tracts; and
comparing the size of the amplified polynucleotides, wherein the presence of two amplified polynucleotides indicates the individual is not at risk for developing DM2.

30. A method for identifying an individual that has DM2 or is at risk for developing DM2, the method comprising:
providing a tissue sample from an individual;
probing the tissue sample under hybridizing conditions with a detectably labeled probe which hybridizes to a polynucleotide containing a repeat tract within an intron 1 of a ZNF9 genomic sequence;
detecting the probe which has hybridized to polynucleotides present in the tissue sample; and
observing nuclei of cells present in the tissue sample, wherein the presence of the detectably labeled probe in nuclei of the cells indicates the individual has or is at risk for developing DM2.

31. The method of claim 30 wherein the probe comprises $(CAGG)_n$, where n is at least 4.

32. A method for identifying an individual that is not at risk for developing DM2, the method comprising:
providing a tissue sample from an individual;
probing the tissue sample under hybridizing conditions with a detectably labeled probe which hybridizes to a polynucleotide containing a repeat tract within an intron 1 of a ZNF9 genomic sequence;
detecting the probe which has hybridized to polynucleotides present in the tissue sample; and
observing nuclei of cells present in the tissue sample, wherein the absence of the detectably labeled probe in nuclei of the cells indicates the individual is not at risk for developing DM2.

33. The method of claim 32 wherein the probe comprises $(CAGG)_n$, where n is at least 4.

* * * * *

UNITED STATES PATENT AND TRADEMARK OFFICE
CERTIFICATE OF CORRECTION

PATENT NO. : 6,902,896 B2
DATED : June 7, 2005
INVENTOR(S) : Ranum et al.

It is certified that error appears in the above-identified patent and that said Letters Patent is hereby corrected as shown below:

Column 4,
Lines 10 and 11, delete "≦" and insert -- ≤ --

Column 14,
Line 33, delete "≦" and insert -- ≤ --

Column 16,
Line 23, delete "≦" and insert -- ≤ --
Line 23, delete "(13 y/o)" and insert -- (31 y/o) --

Column 19,
Line 7, delete "≦" and insert -- ≤ --

Column 58,
Line 36, delete "develoDing" and insert -- developing --
Line 43, delete "4469"

Column 59,
Line 31, delete "TTGGACTTGQAATGAGTGAATG" and insert
-- TTGGACTTGGAATGAGTGAATG --

Signed and Sealed this

Ninth Day of August, 2005

JON W. DUDAS
*Director of the United States Patent and Trademark Office*

SEQUENCE LISTING

```
<160> NUMBER OF SEQ ID NOS: 39

<210> SEQ ID NO 1
<211> LENGTH: 22400
<212> TYPE: DNA
<213> ORGANISM: homo sapiens
<220> FEATURE:
<221> NAME/KEY: misc_feature
<222> LOCATION: (14469)..(14473)
<223> OTHER INFORMATION: any nucleotide

<400> SEQUENCE: 1
actaatgaaa tgttcattaa atgatttgtc agtgtttcaa agtttcttta tcatcagtta      60
gcattcccta caccatcact ttagggagtc aatagaattt tataggagta ggcttcagta     120
agtactggga ggccagtagc actgttcaag cacatgggct gtctgtgttt gaagcctgac     180
ctgtcatttg ttcactttct gacttgagca gattacttaa actctctcga cctgtttctt     240
catggggata atacaagtac ttctaggggg tttgtgaaaa ctcataaaga ggttaaaaac     300
attgcctggc atacagtaag cacccaataa gaataagaaa taatatttgt atagtaatta     360
```

```
tgccagaaac tgttataaga gctgtatata tattaacaat tagctattac tagtattact      420
aattcctagt tcaggattta gcttagtaaa ctttctgctt cagaagcaaa tacgagaggt      480
gaaaacatca atttattctc ctcagtctta gttacatact ttccaagtca agtcacagag      540
cacaatttcc ttgctggcag ggacaagaca tgggtttaca tgatatcacc tatcccctca      600
atttaacagc atgtactatg cagttgggca tttaagcaga aattaagagt tggcaggtat      660
tgctcaactg gtacccattt taggaataat gctgaatcat agcatttat  ctggtcttct      720 ctcaggatac ttaatgctaa ttttttgtat ttttagtaga gacgggattt caccttgtta      780
gccaggatgg tctcgatctc ctgacctcat gacccatctg cctcggcccc caaagtgct      840 gggattatag gcgtgatcca ccgtgcccgg acttttttt  tttttttttt tttgagacag      900
agtctccctc tgttgtgcag gctggagtgc agtggcccaa tctcttgctc caggtgcaa      960 gcgattctcc tgcctcagct tcccaagtag ctgggattac aggtgcccac caccacactc     1020
ggctaatttt tgtgttatta gtagagacaa gttttcacta tgttgcccag gctgctctca     1080
aactcctgac ctcaggtgat ccacctacct cggcctccca gtgctggga  agttgttttt     1140 ttttctttt  cttttttga  gactgagtct tgctccgtca cccaggctgg agtgcagtgg     1200
cgtgatctcg gctcactgca agctctgcct tcaggttca  aacgattctc ctgcctcaac     1260
ctctcgagta gcttggacta taggtccccg ccaccacgac cagctaattt tttgtatttt     1320
tagtagacag gatttcaccg tgttagccag gatggtcttg atcagctgac ctcgtgatcc     1380
gcccgcctcg gcctcccaaa gtgctggatt acaggcgtga ccaccgaac  ccagccgaca     1440 cttaatactt tcttatggcc cttgttatcc tgcaagttct tcaagggcaa actctgtgtc     1500
ttaagtagtc acctttgtaa cccttgcaat gctgagcatg agactgaaca ctggaggaga     1560 ggagggaat  aaaacatctc cagggaagag gaatgtaatg ggagcctctt caagtcccac     1620
tggcagctta tcttttgagt gagcttttc  ctattttcaa acatttctag taaaataggc     1680
ataccaaagg gtatatccag gcaatacaag ccattgtagt taaattccac catacacctt     1740
ttctggcgcc tcacgatcag cctggctcta ttaataatag tcgttacagg aagctgcatg     1800 ccagtagaa  agagccatta gctgttacca ctccactgcc aagaagtaaa gacattgttt     1860
ccatttcttc tacttaagtc ttttaaaacc tatagaacat tatgtccagt atctctatct     1920
cacactcact ttcattttct atagctgttg aaattttgt  tttaatatta ggaatattcc     1980
attcctgggt ctataatgaa tagcaaacat tttatacagt actatggttg gaatggtaaa     2040
caaaaataag tcagaaaata ttaattttg  gccatatggt aattttaact tgtcctcttg     2100
gtgtggtgtg gacgcaccca ggttggactt catacatagc ctcttgcatt atattgactc     2160
attgtcagag ctcacgaagt cactacctaa gtgtctgatt gctacactat acattacttc     2220
aagatactat gaaggttaat cagattacaa aggggaaatc ataaagctga gtaagcttct     2280
tggtaataaa actatataaa tacaaaatac tgttttttat tggcagataa tatatcgtgt     2340
tttagcacaa cacataagct gctaggcatt tattcaatct gattgggaat gggttaaatt     2400
tggttaaaaa attttacctt aggttgcttt aattaaaaaa atgtttaagg ctgagtgcag     2460
tggctcacac ctgtaatcct agcactttgg gggcactggg tgcagtggct cacacctgta     2520
atcctagcac tttggcctag caccgcttga ggccaggagt tcaagcccag cctggccaac     2580
atgatgaaac cccatctcta ctaaaaatac aaaaattagc caggcgtggt ggtgggcgcc     2640
tgcagtccca gctactcagg aggctgaggc agaattggtc aaacatggga agcggaggtt     2700
```

```
gcagtgagct gagacagcac tccagcttgg gcaacagagg gagaccctgt ctcaaaaaat      2760
agtaataaat aaatttaaaa agttcggcca ggcgcggtgg ctcatgcctg taatcccagt      2820
gctttgggag gacgatcacc actttgggtg ggcggatcac ctgaggtcgg gagtttgaga      2880
ccagcctgac caacatggag aaaccccgcc tatactaaaa atacaaaatt agccgggcgt      2940
ggtggcgcat gcctataatc ccagctactg gggaggctga ggcaggagaa tcacttgaat      3000
ccaggaggcg gaggttgcag tgagctgaga tcgtgccatt gcactccagc ctgggcaacg      3060
gagtgagact ccgttctcaa aaaaaaaaaa aagtttaaaa tatcattggt ctttaaagtt      3120
atacattcat tctttgataa ttgctatgtt gaacgcaacc tcctaactgc tttacaatga      3180
ttaagcacta atgatttgaa cccaggttta agtctgact ctcaacacat gtgctctgcc       3240
ttctcacgaa catgatttca aaatcatag ccccggatt tgggattggt ggcttatgcc        3300
tgtaaaccca gcgacagagc aagaccctac tcttaaaaaa aaaaaaatt aaagaaaaaa       3360 agaaaaataa atcatagtgt tgaactggca ggtttcactg agacgaaact tgggactctt      3420 ccttttttt tgtttcgaat aaagccattc tagaatgaga caaaattcta aaatatttta      3480
tagttaacag tttaaattgg gtttaatctt gacaagacta tctagggcta tatacacaaa      3540
tctcttttgg agaaaatacc acaactaaac tgaagtctat tcctgaatat gacagaccag      3600
gtcaaatggt tatccttgcc ctcccggggg atgtcactca taaacgtgcc aaaagtcaca      3660
gtctaggccc cattaccttta catgctcatg accttcccag ggaggcccct cgcccttacc     3720
aggcactttc atcttgggaa gacacatcag tcctggcgga gaaagcagca aggcctttcc      3780
ccggctcaca aaaattaata caaatctcag aggctgcatc ccacagccgt gaccaccgtg      3840
acttggcatc cccttttctg caaacttaaa tgttatctag aaatcgggcc tggctctgaa      3900
agccaagggc ctggcaggag cccgagaaag gggagaaact ttctgcggcc ccaagctaat      3960
ggcagtcact gcaccgagac ccgtcccctg gcatcccttt gctccagctg gccaagacag      4020
accaccaagg tcagccagat ttccacccag tctggccggg cccggaccca gctgggaatg      4080
aaccgagaag caccgggacc cggatcccgg cgtgaaaggc cgcgcgcggg gcacggcggg      4140
aaaagacgct gcgcgcagaa acacccgccc cgcgccgcgc tctagtgggc ggccctgccg      4200
cgggcggctc tgattggact gccgaacccc gcgcgctgat tggccgcgtg ggcgaggcgg      4260
aggagagccg tgcgcagcgg cgtatgtggg gccgtgtgca gacccgcgtg tggcgcaggc      4320
aaggaccctc aaaataaaca gcctctacct tgcgagccgt cttccccagg cctgcgtccg      4380
agtctccgcc gctgcgggcc cgctccgacg cggaaggtga gggctggggg aggggcccgg      4440
cgctgacgga gccgcagtgc gggtcgggtc tgtggcggac agagagggta gggagcggcg      4500
aggtggcgat ggcggccgca ctttggcctg cgcctctgct gcgtcaggcg ggaagctcgg      4560
ctgctgccgc cgcctcggac ccgggtttct ggcgcaccgc tgtcggacga cacttctgtc      4620
cttctctcgt cctggaaagc tgggtcgccg agcatgcggt tctttcggcg ccacggccgc      4680
accccaggcc gcaggcttag ggcagaggag gcccgcccgt gcgcccttgg ggccgaggcc      4740
ctgacgcttc gagggtcgcg gaatgaggga ccgaggtgg atttggcggg aactcactgg       4800
aaggagtccg tgtggtgggg aaaggctccc ggctgcggat gaagggggga tgggtgggt      4860 atagtcgtgc aggccatgtg ctgggtcgt gcgcctggcg ggccatgtgc caagggtttt       4920
gggggcctta gaaaagggtt cttaggccgg gcgcggtggc tcacgcctgt aatcccagca      4980
ctttgagagt cccaggcggg cggatcacga ggtcaggagt cgagaccag cctgaccaat        5040 atggtgaaag ttggtctgta ctaaaaataa aaaattagcc gggcatggtg gcgggcgcat      5100
```

```
gtagtcccag cagctcggga ggctggacag gagaatcgcg tgaacccgg aggccgaggt   5160
tgtggtgagc cgagatcgcg ccactacact ccagcatggg caacagagag agactccgtc   5220
ttaaaaaaac aaacaaacaa acaaacaaac aacaacaaag ggttcctgaa gaagcctttg   5280
tgtttggagt ggcgagactg ctggaagact tgggagcttt tagagtttat actccctatc   5340
cttgatagtt ttccgattct tgaattttta tcgtcattta aatactaagt tgcttgtgtt   5400
acattaccat tccaaaaggg gctgatgggg ctcacattcc aagagttaac actatttaag   5460
ttgctgggat cctttaaaag cgccattacc agaaaaaaca cgaatttgtc aaacctccaa   5520
aaccacagca gcgggcggta gtctgcatca tttcttggat taatgaaaca gatgtaatta   5580
caaacgagac acgaaattca actagctccc ctccatctag attttccat atcgtgagaa   5640
cctgttttag aatggcataa tggtccacat ttgggtttag gtgttgattt tattatgggt   5700
aaggcttgtg cttgttccca catgttaacc atatggcctc agccacaggg cacttccaaa   5760
ggaagtgact gtttctggtc ttgggggtct tgtaaaaaga gaacattgct cagtaatcgt   5820
ctgtgatttt agctagtgtg tttcaggcat tattcagaag gactcaggtg agataagcca   5880
aaactgaatt tgttttttgt ctttctcaaa gtgaaggagg tctaatgaat atccccatct   5940
tgcttttaaa ttacattttt aaaagtagat ttttcccct ttcctattgt ttgacccaat   6000
tttggagtga aacgtaacca gttactattt ccattcgaat ttaaattagc aattttatgt   6060
tatttgtttg ttcaagcagt ataactggag tgtagagctt tgagggtttc aaaaagataa   6120
gagatatagt acttatctcc tgggcttccc cctccccct cctaaatagt tttaaatgct   6180
tctaatgagt tactctggtt aaggataatc aaacacctgt aaactgccag gatcctaggt   6240
acatgctgtt tttagtttgt tgagcctgat tcttgtctac aagagttctt tgtgtattgg   6300
aatataaaag gaataattta ttacattccc aagggcagaa ttaaagactt aagttttttcc   6360
gatttcatct cttgataagt ttttctttaa aaaaataaca gtttgtgttt ttctgaggaa   6420
ccaaaggtcc tcttttttt catattggta acaggagagg taatgtattt cagatggtgc   6480
agtctgtaaa atattttgaa ccaaatcagt ggaagaccag gggttttttct ttttttttt   6540
ctgagacgga gtctcactct gtcgcccaag ctggagtgca gtggcgcgat ctcggctcac   6600
tgcgacctcc gcctcccgga ttaagcgatt ctcctgcctc agcctccgaa gtagctggga   6660
ttacaggcgc ccgccgccac acccagctag ttttttgtatt ttagtacaga cggggtttca   6720
ccatgttggc caggctggtc tcgaactcct gaccttgtga tccgactccc tcggcctctc   6780
aaagtgctag gaaaacaggc aggagccacc gcgcctggcc aggttttttct taaactggca   6840
tttgaacatc tggaacaggc agggagatgt ctttttttaaa gtataaatgt gttttgttac   6900
atgatttatg acaattctac ttgtcttttt tttttttttt tttttttgag acagagtctt   6960
tctctgtcgg ccaggctgga atgcagtggc acagtctcgg ctcacagcag cctccatctc   7020
ccgggctcaa gcaattctcc tgcctcagcc tcccaagtag ctgggattac agggcgtgtg   7080
ccaccacgcc cggctaattt ttgtatttttt tgtaaagacg gggtttcacc atgttggcca   7140
ggctggtctt gatctcctga cctcaggtaa ttcacccgcc tcggcctccc aaagtgctgg   7200
gattacaggc ctgagccacc gtgccttgcc acaattccta cttgtctttt aaagttcaat   7260
aaaaatatgt ggcacgtata tgggatagta ccaaactggt gcctaaaagc agtgaaacca   7320
ccattggact aattgaaatg atttgtctat tggctgaaga tttgaccaca gagagattct   7380
gcttttttttt ccttgcaggg atgaaaaatt aaaaaaaaaa aaaagattg gttccttttt   7440
```

-continued

```
ctcttcctag cctcctgaca gtaagtagag agccagaaga atgatgccaa ggcatcctgg    7500
cctgctatgt ggagaacgct ctttccttac tgtctcactt aatagaactc ctgttctggc    7560
agtgtcagat gctgcagcag caagggaatg ccattgagtg attgcagtaa gctatgcagc    7620
attttcatgt ttaaaactac tgagataata aagtgagaac ttgaggccac caaattttaa    7680
gttgtaatta aaggatttt gttaattagg aatatgagag tgctacagtg atcacctgga    7740
atggctccat aaatacaaat gaggtgttaa ctagtgaagc aagttgccag tgtttgtgtg    7800
tttggtgaga ctcctaagtt ctgccatgaa gttaaagaaa atattttta agattcaaga    7860 aagctgtgtg aatgaattca aaattattat gactgtagat cttttaaaaa gctatcagta    7920
ttagttttac tttgattttt atctaaagag aaatacagaa tgaatactta cagcattaca    7980
attcaaatgt gcgtggcttt ttttttttct agttactaga tatatagtag taatacccttt    8040 atgtaatatt ttgaagtaga gattgaattg gtataattcc ctaccttaaa aatattacac    8100
aatagcattt ttgtcatata ttacgatagc atttttgtgt acttaccac ttaacttttt     8160 ttttccttt ctttttttt tggagacaaa gtcttgctct gtcgcccagg cgggagtgca      8220
atggcaggat ctcagctcac tgcaacctct gcctcctggg tttaagccat tctcctgcct    8280
cagcctcctg agtagctggg actataggcg tgtgccacca cgcccggcta attttttgttt   8340 ttttagttt ttttggagac ggagtctcgc tttgtcaccc acactggagt gcaaatggca     8400
tgatctcggc tcactgcagc ctccacctcc tgggttcaag cgattctctt gcctcatgca    8460
ccaccacgcc cagttaattt ttgtatattt agtagagatg gggtgtcact atgttggcca    8520
ggctgccgac ctcaagtgat cttccctcct cagcctccca aagtgctggg attacaggca    8580
tgagccactg cccctggcca gtgtcagatg tttagtttgt cattaaaatg gagcaagaat    8640
acataactcg tgaggttgta agattataga tatgtttact aatgactgac tcatagatat    8700
ccagctgtta aaactcttca agaagtaatc agggcaggcg gaaatggatg taattaacca    8760
aggtcaagca gtaagttcag gaaccaggat aaaaatacag aattgctccc gagtaagtac    8820 tctgtttcc attattctgg ctggaatgca ggtaatacag aaagtatatt gcttcctttc     8880 attgctttt ttttcttctt ttttttccttt gaggtggagt tcgctcttg ttgcccaggc     8940 tggagtgcga tggcatgatc tcggctcacc gcaacctctg cctcctgggt tcaagcaatt    9000
cttgtgcgtc agcctcctga gtagctggga ttacaggcat gcaccaccat gtccagctaa    9060
tttttgtatt tttagtagag acagggtttc accatgttgg ctagctggtc tcgaactcct    9120
gacctcaggt gatgcatctg cctcggcctc ccaaaatgct gggattagag gtgtgggcca    9180
ccccgcccgg cccagacctt atcttgacta tcttagtcat ttcttctctt gcctgacatg    9240
ccctgtgctc ctaccaccct ttaaagtggt ttgtgtcata acatttgat acacaaaaat     9300 ggaaacttag gacaaatatc ttgatgtctg gtggttgaaa atgtgaactg atttggaaat    9360
caccggtgtt tctcctctta atctcttctc cattccattc aggaaataga ctgtaaggtg    9420
ggaaacaagt ataagcagtt agcctcactc taaacctgct atgtaataga cattggactg    9480
agttctgtct actctctgta agcaatccaa ggtaattggc gaaagtggaa ggaatatgta    9540
ctcagaagac caaaactttg gttttttaaat tgaatatcta ttaagcacaa ggtaacaatt   9600
cttaccacac acatcagttt tattatttcc cttttacaaa taagacacag atgggtagtc    9660
agatgtcttt gaggtaacac agcaagtagt taaactgggt taagtgatta acccaggttg    9720
agtatggttc caaaatctct tacagtgtca ggcaggctac atcagtgcag tatacgtaca    9780
tcaggtttca cgaaaaattt tttccagaga aaacacaaac ccaaggaacc ttcagtaagt    9840
```

```
ggtgccttat attagtggtt tttagcaaaa ggaagaaact taagtgtttt cctgctgcct   9900
gacaaaagtg aaaaacagta ttttggtttt tattgaagtt agcatgtatg tttgtagctt   9960
gcataaaata gtactgaaat ccaattgatt atgaattctt ggactaacag aacctggatg  10020
acaaattaga ggttctggcc tggttgctgg cttttttagt tgtcttgggt gtaaatttct  10080
cagccacacg tggggattgt gttagataat ctgaaatcta attttcatgg ttttatgatt  10140
cagcagcttt cttcctttga tattttctag tatttgcttt attatagatt ggaatcctca  10200
aaataacatt gacaagtaga agatacttct gttagtggaa ttaaaaaaaa attacattgg  10260
gaatgtcctt tgagtggttg gccctaatcc ctgtcagaag ctgaaagttg tggatcctaa  10320
attcatctgg gcagaatctc acctatgatt tcagaaagct gagagtttca gagagtgact  10380
gtagtcagtc cttagtgagt acaaaattga gaatacatca ttactttaaa ttaatggtgc  10440
agtaactctt tgtgactgata gcaataattt aggtgctttg ttgttagtac ttgattagat  10500
tggattgggt cagttagttt caccaaattg ctaaagacac ctgtccccct agaattaaaa  10560
tactgagtta cataatggct actaaaagga taactatatg gggtgttcga tgattcaaag  10620
gtgaattact tggtctctac cttcaaggaa tatgatacaa ggcaatatgg tactgccatt  10680
agacagatat taacaaagtg tcttgggact taataggggag ggtagttcca ggctgggaga  10740
tgtagtcaga ttcttttata gagttggcat ttgagttggc ccgtgaaggt tggaaaaagt  10800
tgtgacaggt ggaaaaggag caggggagac caggacagtg cagtgaaatt ccagccagga  10860
gcagtcatag gcaatgagac agactcatgg agccatgatt ctcagctgtc ttaccttacc  10920
ttagttttcc taaggaatat catggaattc tgtaaagacc tttaaactaa ataatgttca  10980
tatgagatga gtgctaggat ggggacctgc tgcctaatat aagtagtgtg agtctaaaac  11040
attgtggaaa gtggttagtt taataatgtt attaaagaga caagtctatc acaagggacc  11100
agttaccagt gaaactgtag accacctgat tcactgcgat agggttagcc aaagggagga  11160
gagggcagat tgcatacata gtacctaagg ccactcaaag acctctttta aaatcacgtg  11220
tcatgttgat gacatttgga ggctattaat gttttttcttc cctttttaaga cttagtgttt  11280
tcttttattag cattaatttta ctctagtaaa caaaattatg tgtgactaaa aatggcaaaa  11340
caggctgggc gcagtggctc acgcctgtaa tcctaacact tgggaggcc aaggcgggtg  11400
gatcactagg tcaggagatc gagaccatcc tggccaacat ggtgaaaccc cgtctctact  11460
aaaatacaaa aaattacctg gcgtggtgg tgcacgcctg tagtcccagc tatgtgggag  11520
gctgaggcag gggaatcgct tgaacccagg aggtgaaggt tgcagtgagc caagattggg  11580
ccaccgcact ccagcctggg acagagcgag actccatctc aaaaacaaaa aaagatcca  11640
aattagaaga acatggtggc atgcgcctgt agtcccagct acttgggagg ctgaggcagg  11700
agaattactt gaacccggga ggcagaggtt gcagtgagcc gagattgcac aactacactc  11760
cagcctgcgc aacagagcaa gactccatct caaaaaaaaa aaagaaaga aagaaagaaa  11820
gaaactggag ggaacaatgc cctaatgtat taacaatcat cacatatgag gtgtgaaaat  11880
gtgagtggtt ttttctgat tttctgtatt ttataacttt ttttgtttg agatggagtc  11940
ctgctctgct gcccaggctg gagcgcagtg ggacgatctc ggctcactgc aacctctgcc  12000
tcccaggttc aagtgattct cctgcctcag cctcctgagt agctgggatt acaggtgcct  12060
gccatatgcc cagctaattt ttttttgtatt tttagtagag acagggtttc accatgttgg  12120
ccaggctggt ctcgaactcc tgaccttgtg attctcccgc ctcaggctcc caaagtgctg  12180
```

```
ggattacagg catgagccac tgcgcctggc tataactcct ctgtagtaaa aaatatattc    12240
cttcataatt aatggcacaa tatttaaact ctgaattatt tttaagggat ggtagtggcc    12300
tatgcaaaac tagctgtgga ataatgaatt ttaaaataag cagcatttaa taaaaataga    12360
actatatttt ttttaaaata gaaaagccaa ctagaaggag atataacaaa atgctaataa    12420
tggtgaaaat actggcatca ttcttctctg cctctcatac ttttttcctat gaagtgttga    12480 ctacctttct aaaacacaaa atcaaaaccg actaaaactc cagactaaca gtttcaaatt    12540
atattcagga ggtttggctg aaagaaggag gaaaggtggg tgtgccctat ttggattcac    12600
acaaaagtag ctccactttt ctcctttttt tttttgaga tggagttcg ctcttgctgt       12660 ccaggctgga gtgcaatggc acgatctcgg ctcaccgcaa cctccacccc tcagattcaa    12720
gcaattctcc tgtctcagtc tcctgagtag ctgggagtac aggcatgcac caccatgccc    12780
agctaatttt gtatgtttag tggagacggg gtttctccat gttggtcaag ctggtctcta    12840
actccctacc tcaggtgatc cgccacctc agcctcccaa agtgctggga ttacaggcat     12900
gagccacagt gctgggcctc acttttctcc attttttacat ttagggtttg cccaagatt    12960 gtatttgttc tttggttatc atttgttcaa ctaataagta actgaaacat gacctgattc    13020
aatgaacttc agagcctgcc ccaatcgttc tgggaaactt caaataggga aactccttgt    13080
ccagactgac agattagcac ctgccaaagg cagaatcctg caccagccaa tcctgggcac    13140
actttccagc cccaattgta tggcatgggc ctatgattct atcccagttc ttaagaattc    13200
tcagttaaaa tctgggaaca ataattccta cactataagg ctgttatgca actaagaaaa    13260
aaaagtaaga gcagttagca tatagcatat ctactcttat gattattacc aatgaaaggc    13320
taaaactgtc acaaacttac ttacgttctt tttcaaacag ctctctaaca ccaggcaaat    13380
cttttgctgc tccaaagtac ttgtaacctc ggtttcctgg gacttctttt ccttcatgat    13440
ccagcatttt agggccaact ttcttattgg gaagaaaaaa agagaaaatg gatctgttag    13500
ttagttagtt agttattatt tatttattta tttgaggcgg agtctcgctc tgttgcccat    13560
ttatttattt gaggtggagt ctcgctctgt tgcccaggct ggagtgcagt agcacaatct    13620
cactgcaacc tccacctcct gggttcaagt gattctcctg cctcagcctc ctgagtagct    13680
gggattacag gtgcgtgcca ccacgcctgg ctaattttg tattttagt agagacgggg      13740 tttcaccatg ttggtcagga tggtcttgaa ctcctgacct catgatccac ccacctcgac    13800
ctcccaaagt gctgggatta caggcgtgag ccaccgcgcc cggcattgtg ggttttttt     13860 ttaatgctgt tgttttttgt ttgtgtgttt gtttttcttt tataataacc ctcaggccat    13920
tctatcatag gtctgctgaa gtttgctggg ggtctggtcc agatcccagt tgccttgttt    13980
ttttcccata cctggactta tcaccagtga agcctttaaa acagcaaaga tagtagcaag    14040
ctccttcctg tggaagttcc atcccggggc ggttctgacc tgttgccaac ccacatgcat    14100
caggaggttg ctggagaccc ccattgggag ggcttaccca gtcaggagga acagaatcag    14160
tgacttaccc aaagaagcag tctgactgct ttttggtaga gcagttgtgc tgcactctgg    14220
gagacccttc cttgtccaga cagcctgtat tctccacagt ctgcatgctg gagcagctga    14280
atcaacagga ccacagagat ggtggcagcc cttcccccag gaactccatc ccagggagag    14340
atcagagttt tatctgtaga accctggctg gagtggctga agccctgca aggagatcct    14400 gcccagtgag gaggaatgga tcgggatccc acgaacgggc tgatgaacta ctgtccatcg    14460
ataggcgcnn nnnatagatt tcatgatgaa gttgacgcta gtggtaacaa gttatataga    14520
acatgatcgt cctcatatgg cggagtttag tgagcattgt gttccttttg tgagagtaaa    14580
```

```
gcttttatt aatgatagag tgttattttg gtgaggtttt ttagggtgtg gcgagtgtgc    14640
gtatagccat gtcttgaaaa tgggggatgg gattagtatg atcagaaggg agttggggag    14700
gaatcactgg tttgtaaatt gagggggaag ggcctatcta atgcaggaaa caaggtggcc    14760
atgcgggagc tgatcagcag gccaaaattg tggggtgaat ggagttaatt catagcaggg    14820
tttaaagagc ttatgtgggg acagatgaag atttatcatg gtctagaatc atttcggagc    14880
tttgtttgcg tgtcaggccc cgtgatatgt gcaagagcgc catcagtacg cgtcatggga    14940
gcatactgtt ttcgggatgg gtttcgagcg aagatgtgag cagatactgc tgtcaatggt    15000
gaagccttga ttagaggcac catatgcagt tcttcatgat gctttacatc cataaaagcc    15060
tcggcagcgc ccagcaagag aattcagtgg tgctattcct tttgaggtgg ggagtggagt    15120
atctctcgat cagcgcgtgt ttaccatgcc ccagtcttag ttatcttcat gttcaaggtt    15180 ccggggcaa agtgattctc ctacctcatc ctctagagta gttatgacta cagagcatgt    15240
tatcaccacg accgggtaat gaaagtatta tagtagattg ggggtttaca ccatgttgga    15300
caggatggta ttaatttcct gacctcatga tccgcctgcc tcccaaagtg ctgagattac    15360
aggcgtgagc caccacgcct gccctaattt tgtgttttta gtagagatgg agtttcactg    15420
tgttggtcag gctgatgtcc aactcctgac ctcaggtgat cctcctgcct tggcgtccca    15480
aagtgctggg attacaggtg tgagccactg tgcccatcct tgttttgtat tttctaaaag    15540
agatgtatct tgtttaaata ttaaattata agatattcag gccttgcaaa ttgtctggat    15600
tacactgtaa aagtaatcat ttatgtgcaa ataattcctt gagatcaata gttaaatgag    15660
ctcaagctga tctgactaaa ttggagaaga tacaaaatga agatggggag gaagtggtgc    15720
cataagcagc ctttttctt tgaccatttt atatgccttt tttttttttt ttttgagatg    15780
gagtttcact cttgtaaccc acgttggagt gcaattgctt ggcttgcaac aacctccacc    15840
tcccgggttc aagagattat cctgcctccg cctcctgagt agctgggatt ataggcatga    15900
gccaccaagc ctggctaatt ttgcatttt agtagagacg gggtttctcc ttcttggtga    15960
ggctggtctc gaactcccaa cctcaggtga accatcctcg tcggcctccc aaagtgctgg    16020
gattacaggt gtgagccacc gtgccctgcc cgccattcgt tttttttttt tttttttttt    16080
ttttaattct gactcttctg tggtggaaac cagcaaatac ttcacataat ttaggatgct    16140
aatactagta cagttaaaag aatgattaca aagcagatac tatttcaaat tctgtaaaaa    16200
tctgttttta atatccttca ctggctgttt gttctgacta gaaatgtttt gtatatctga    16260
aagcaccagt aactcatagc catataattt ttttggtaat atgttcatag gcaagtggca    16320
agagttagta gaaagatttc tctaagaatt tatcctaaat cagattacac agagttgggg    16380
taagtgagta ttgtgttatt ttcttttgta tatttgacaa tgggaacttt ttgaaactca    16440
acttcagtgt aattttaagt cactaaattt gtccacaagt taatgattaa acagttactg    16500
aaagtggaga accttgccat ttttcggact gcgttttggg tctttggcac tgtggttagg    16560
ttagctaatt cgattatcca ctcaagtttt actcagttgg aaatatgttt ttctagatga    16620
tggtgcctgt gcttaggttt gagaggatat ttaaaatacg actttgtgtg ccattgtttg    16680
acagtggaat taagggtaaa aatatttaga tatggaagtg tgaaaatgta gttgcattgt    16740
tttcattatg ttctattcca tttcattcta ttttaagaat agcctcaatt tatttttaga    16800
ttgttacata agtacaaaat ccatttgctt tagtgggagt tttatttta ttttaaaatg    16860 ataaccaatt aaaggagttt attatgaaat tctaagtagc attgtttaaa atgtaaaatt    16920
```

-continued

| | | | | | |
|---|---|---|---|---|---|
| acattacaga | aacatttgga | aaggggagaa | taaaagaaaa | caaaacacaa | atgttgccag | 16980 |
| tgctgtaggt | gctattatta | gcgctttggt | gtaactcatg | gtcgttttcc | tactattttt | 17040 |
| attatacagt | catctcttgg | tatctgtgaa | gtggttccac | aaactccctc | aaataccaaa | 17100 |
| atcctcctat | gctcaagttc | ccaatataaa | atagtgtagt | acttgcatta | caacctttgc | 17160 |
| acatcttccc | atatacttta | aaatcatctt | tagattactt | ataataccta | acacaatgta | 17220 |
| aatgctgaat | aagtagttgt | taacattgta | ttgtttaggg | aataatggca | agaaaagtct | 17280 |
| gcatgttcaa | tacagatgca | acttttccac | tgaatatttt | tattccaagg | ttggttgaag | 17340 |
| ccatggatgc | agaacccatg | gatatagagg | gcctactgta | cttgtaccat | ctagagataa | 17400 |
| gatttgtatc | ttgcatttgt | tttaacatat | ctgttctaag | gaatatctca | gtcaccaggc | 17460 |
| aagtgctgca | gtataactag | gtactacgtc | aggtgctaag | gttaagagag | tattttcctt | 17520 |
| cactgactcc | tcactccgag | aatccatttt | acagcttcat | tggtttgggt | tattccaatt | 17580 |
| ttttgatgtg | agtaaataaa | tgacttctat | ttgcccaaaa | taaagcttat | ataggcctta | 17640 |
| taaccatgca | aatgtgtcca | ttaagttgga | cttggaatga | gtgaatgagt | attactgcca | 17700 |
| gtgtgtgtgt | gtgtgtgtgt | gtgtgtgtgt | gtgtgtgtct | gtctgtctgt | ctgtctgtct | 17760 |
| gtctgtctgt | ctgtctgcct | gcctgcctgc | ctgcctgcct | gcctgcctgg | ctgcctgtct | 17820 |
| gcctgtctgc | ctgcctgcct | gcctgcctgc | ctgcctgtct | gtctcacttt | gtcccctagg | 17880 |
| ctggagtgca | gtggtatgat | ctcggctcac | tgcaacctcc | acccccgggg | ttcaagcgat | 17940 |
| tcttctgcct | cagcctcctg | agtagctggg | attacaggcg | catgccgcca | tgcccggctg | 18000 |
| tttttttgtat | ttttagtaga | gacggggttt | cgccatgttg | gccagactgg | tctcaaactc | 18060 |
| ctgacctcag | atggtccacc | cgcttcagcc | tcccaaagtg | ctaggattac | aggcatgagc | 18120 |
| caccgtgccc | agccactacc | aattatttct | cttaatggat | tttcattgac | cctaaccctg | 18180 |
| taaattccat | cacttttatc | aaggtgtata | ttataataag | tctataatac | ccaatcatgt | 18240 |
| agttgtgtga | ttattttatt | tttttgagac | agagtctcaa | tgttgcccag | gctggagtac | 18300 |
| agtggcacca | tctcagctca | ctgtaagctc | cgcctcctgg | gttcacacca | ttctcctgcc | 18360 |
| tcagcctccc | aagtagctgg | gattacaggc | gcctgccact | tcaccgggct | aattttttgt | 18420 |
| attttttcgta | gagacggggt | ttcaccatgt | tagccaagat | ggtctcgatc | tcatgatcca | 18480 |
| cccacctcgg | cctcccaaag | tgatgggatt | actggcgtga | gccaccatgc | ccagctattt | 18540 |
| ttttaaccaa | tatattagct | agcttttttc | cccagaataa | ttttccaaaa | atacatttaa | 18600 |
| tagagaataa | aagttaaaag | aactttcagt | ggtttaatgc | tgttactttt | aatatttcaa | 18660 |
| agatctgact | gcagccatga | gcagcaatga | gtgcttcaag | tgtggacgat | ctggccactg | 18720 |
| ggcccgggaa | tgtcctactg | gtggaggccg | tggtcgtgga | atgagaagcc | gtggcagagg | 18780 |
| tggttttacc | tcggatagag | gtattttgtc | gaatagaaaa | atttgaagta | cttcagtatt | 18840 |
| tgttagtatc | aagactggtc | tgactagccg | aattctttgt | ttttgctcaa | acaggtttc | 18900 |
| cagtttgttt | cctcgtctct | tccagacatt | tgttatcgct | gtggtgagtc | tggtcatctt | 18960 |
| gccaaggatt | gtgatcttca | ggaggatggt | aagtatttaa | cacttccttt | tcataccct | 19020 |
| ctagagcttg | gagaggtgag | cacatgcaac | tgtgtatagc | atttccacct | ttgaggtttt | 19080 |
| gtattgtata | atttaaaacg | taacactttg | taaaggtttt | atagtcttgg | cctgtttctt | 19140 |
| ttccttattg | ttgaagcctg | ctataactgc | ggtagaggtg | gccacattgc | caaggactgc | 19200 |
| aaggagccca | agagagagcg | agagcaatgc | tgctacaact | gtggcaaacc | aggccatctg | 19260 |
| gctcgtgact | gcgaccatgc | agatgagcag | aaatgctatt | cttgtggaga | attcggacac | 19320 |

```
attcaaaaag actgcaccaa agtgaagtgc tataggtaag gtgtcagaat gttgttagaa    19380
gaaaactcat tgcagagatt cttccagaga tgaattagct ataaatggaa gggccttagt    19440
aaattcagtg aaacttagct gtgaccagat aagaccaatt ttcagcatat gtaactggca    19500
gtctatctgt atataattct gtattctgcc ctgatatcct gtggcttatg gtacctgggc    19560
agttttcaca actggacttt tttaatatat aaaagtaaga gtgttataat ttgaaacttc    19620
cagagacttc atagaaagct ctgtaatata cataaatctt ttatcatgta accagaaatc    19680
tttgcctgtt tgtgacatgt aagtgtataa tttgataaat gttgttgtgt acatatctgt    19740
gaaaccttag gggttaattg catgaaaaca aagatcaggc gttttgttct gcatggtgac    19800
tgttgctttg gtagacagtt ttttctgag gcccattgtg aaaactttta atttcttttt    19860
taggtgtggt gaaactggtc atgtagccat caactgcagc aagacaagtg aagtcaactg    19920
ttaccgctgt ggcgagtcag ggcaccttgc acgggaatgc acaattgagg ctacagccta    19980 attatttttcc tttgtcgccc ctccttttc tgattgatgg ttgtattatt ttctctgaat    20040
cctcttcact ggccaaaggt tggcagatag aggcaactcc caggccagtg agctttactt    20100
gccgtgtaaa aggaggaaag gggtggaaaa aaaccgactt tctgcattta actacaaaaa    20160
aagtttatgt ttagtttggt agaggtgtta tgtataatgc tttgttaaag aacccccttt    20220
ccgtgccact ggtgaatagg gattgatgaa tgggaagagt tgagtcagac cagtaagccc    20280
gtcctgggtt ccttgaacat gttcccatgt aggaggtaaa accaattctg gaagtgtcta    20340
tgaacttcca taaataactt taattttagt ataatgatgg tcttggattg tctgacctca    20400
gtagctatta aataacatca agtaacatct gtatcaggcc ctacatagaa catacagttg    20460
agtgggagta acaaaaaga taaacatgcg tgttaatggc tgttcgagag aaatcggaat    20520
aaaagcctaa acaggaacaa cttcatcaca gtgttgatgt tggacacata gatggtgatg    20580 gcaaggttt agaacacatt attttcaaag actaaatcta aaacccagag taaacatcaa    20640
tgctcagagt tagcataatt tggagctatt caggaattgc agagaaatgc attttcacag    20700
aaatcaagat gttattttg tatactatat cacttagaca actgtgtttc atttgctgta    20760
atcagttttt aaaagtcaga tggaaagagc aactgaagtc ctagaaaata gaaatgtaat    20820
tttaaactat tccaataaag ctggaggagg aagggagtt tgactaaagt tctttttgtt    20880
tgtttcaaat tttcattaat gtatatagtg caaaatacca tattaaagag gggaatgtgg    20940
aggactgaaa gctgacagtt tggacttttc tttttgtact taagtcatgt cttcaataat    21000
gaaaattgct gttaaaagga tgtatgggat ttagatactt ttgcaaagct atagaaaatt    21060
cactttgtaa tctgttataa taatgcccctt gagttctgtg ttcagtctga acaggtttt    21120 tggtggtggt ggttttgttt tgttttggag acggagtctc actcttgtcg cccaggctgg    21180
agtgcaggct tggctcactg caacctccac ctcccgggtt caagcaattc tcctgcctca    21240
gcctcctgag tagctgggat tacaggcacc cgccaccacc ccccgctaat tttttgtatt    21300
tttattttta ttttttttt ttatttttt ttgagacaga gtgtcgctct gttgcccagg    21360
ctggagtgta gtggtgcgat ctcggctcac tgcaagctcc gcctcctggg ttcgcgccat    21420
tctcctgcct cagcctcctg agtagctggg gctacaggta cccgccaccg cgcccagcta    21480
attttttttt tttgtatttt tagtaaagac gggtttcac ggtgttagcc aggatggtct    21540
caatctcctg acctcgtgat ccgcccgcct tggcctccca aagtgctggg atcacaggcg    21600
tgagccaccg cgcccggcct atttttttgta ttttttagtag agactgggtt tcatcatgtt    21660
```

```
ggtcgggctg gtctccaact cctgacctca ggtgatccac ctgccccgcc ccccaaagtg      21720
ctagtgttac aggtgcgagc caccgtgtcc ggccgattct gaacagtttt aataccattg      21780 ctattttgt gttttccctg ggcctttttt cttttttttt tttttttttg agacagtctc       21840
gctctgttgc ccaggctaga gtgcaatggt gcaatctcag ctcactggaa ccttcacccc      21900
ccacccccac accctgttca gtaattctc ctgcctcagc ctcccaaata gctgggatta       21960
caggtgtccg ccaccacacc cagctaattt ttgttatttt tagtagagat ggggtttcac      22020
tgtgttggtc aggctggtct ccaactgttg ccctcaggtg agccactgtg ccccacccttt     22080 tcctgggttt cataaggatc tgaagtggtg gattccttgt ttttgctagt atctcattta      22140
gagttgagat ggaccttaaa actcatctgt tttaactcac tttttaatag atgagttaaa      22200
cttaatttac ttaaggatgt acagttagag cctggaactt caaccattat tcactcccca     22260
tgccctgttt ccccccactt cgaaattaaa tgcggttagc atcatatagt tcattttccc      22320
cctccatgct gctgtgtgat tcttgacttt gggtatgagt ttttcatcct tcatgcaggg     22380
ttctgtcagt tcatggtata                                                  22400

<210> SEQ ID NO 2
<211> LENGTH: 26
<212> TYPE: DNA
<213> ORGANISM: homo sapiens

<400> SEQUENCE: 2
tgtctgcctg gctgcctgtc tgcctg                                           26

<210> SEQ ID NO 3
<211> LENGTH: 26
<212> TYPE: DNA
<213> ORGANISM: homo sapiens

<400> SEQUENCE: 3
tgtctgcctg tctgcctgtc tgcctg                                           26

<210> SEQ ID NO 4
<211> LENGTH: 18
<212> TYPE: DNA
<213> ORGANISM: homo sapiens

<400> SEQUENCE: 4
tgtctgcctg tctgcctg                                                    18

<210> SEQ ID NO 5
<211> LENGTH: 10
<212> TYPE: DNA
<213> ORGANISM: homo sapiens

<400> SEQUENCE: 5
tgtctgcctg                                                             10

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gtgtgtgtgc atttgtgtgc                                                  20
```

```
<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gaggttgcag tgagctgaat c                                           21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
agctgaccct tgtcttccag                                             20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
caaacaaacc cagtcctcgt                                             20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcctagggga caaagtgaga                                             20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ggccttataa ccatgcaaat g                                           21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gctggcacct tttacaggaa                                             20

<210> SEQ ID NO 13
<211> LENGTH: 20
<212> TYPE: DNA
<213> ORGANISM: Artificial Sequence
<220> FEATURE:
<223> OTHER INFORMATION: primer
```

```
<400> SEQUENCE: 13
atttgccaca tcttcccatc                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtgtgtaagg gggagactgg                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aagcccaagt ggcattctta                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tcattcccag acgtcctttc                                              20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aatcgcttga acctggaaga                                              20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
ctgccggtgg gttttaagt                                               19

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tgcaagacgg tttgaagaga                                              20

<210> SEQ ID NO 20
<211> LENGTH: 20
```

```
-continued

<212> TYPE: DNA
<213> ORGANISM: Artificial Sequence
<220> FEATURE:
<223> OTHER INFORMATION: primer

<400> SEQUENCE: 20
agacactcaa ccgctgacct                                               20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
gatctggaag tggagccaac                                               20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gagaaccttg ccatttttcg                                               20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cacctacagc actggcaaca                                               20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tgagccggaa tcataccagt                                               20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cctgaccttg tgatccgact                                               20

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
```
tgctttatta tagattggaa tcctca       26

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
aagacacctg tccccctaga a       21

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
gggtgacaga gcaagactcc       20

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
ttttaaacaa tgctacttag aatttca       27

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gccgaattct ttgtttttgc       20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ttgctgcagt tgatggctac       20

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
tgaatttact aaggcccttc ca       22

<210> SEQ ID NO 33
<211> LENGTH: 20
<212> TYPE: DNA
<213> ORGANISM: Artificial Sequence

```
-continued

<220> FEATURE:
<223> OTHER INFORMATION: primer

<400> SEQUENCE: 33
gtgctcacct ctccaagctc                                                  20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
gtagccatca actgcagcaa                                                  20

<210> SEQ ID NO 35
<211> LENGTH: 44
<212> TYPE: DNA
<213> ORGANISM: Artificial Sequence
<220> FEATURE:
<223> OTHER INFORMATION: primer

<400> SEQUENCE: 35
taatacgact cactataggg aggacgggct tactggtctg actc                       44

<210> SEQ ID NO 36
<211> LENGTH: 41
<212> TYPE: DNA
<213> ORGANISM: Artificial Sequence
<220> FEATURE:
<223> OTHER INFORMATION: primer

<400> SEQUENCE: 36
tacgcatccg agtttgagac gcaggcaggc aggcaggcag g                          41

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
tacgcatccg agtttgagac g                                                21

<210> SEQ ID NO 38
<211> LENGTH: 22
<212> TYPE: DNA
<213> ORGANISM: Artificial Sequence
<220> FEATURE:
<223> OTHER INFORMATION: probe

<400> SEQUENCE: 38
ttggacttgg aatgagtgaa tg                                               22

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
gccgcagtgc gggtcgggtc tgtggcggac                                       30
```